(12) United States Patent
Arndt et al.

(10) Patent No.: US 7,879,563 B2
(45) Date of Patent: Feb. 1, 2011

(54) METHOD OF SCREENING FOR A CARNITINE TRANSPORTER AGONIST OR ANTAGONIST AND ITS USES

(75) Inventors: Petra Arndt, Bickenbach (DE); Daniel Margerie, Frankfurt (DE); Bodo Brunner, Wiesbaden (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/573,744

(22) PCT Filed: Aug. 13, 2005

(86) PCT No.: PCT/EP2005/008834

§ 371 (c)(1), (2), (4) Date: Sep. 12, 2007

(87) PCT Pub. No.: WO2006/018259

PCT Pub. Date: Feb. 23, 2006

(65) Prior Publication Data

US 2008/0132447 A1 Jun. 5, 2008

(30) Foreign Application Priority Data

Aug. 18, 2004 (EP) ................... 04019543

(51) Int. Cl.
*G01N 33/53* (2006.01)
(52) U.S. Cl. ........................................ 435/7.2
(58) Field of Classification Search ........................ None
See application file for complete search history.

(56) References Cited

U.S. PATENT DOCUMENTS 5,670,113 A * 9/1997 Akong et al. .................. 422/63
7,244,556 B2 * 7/2007 Endou et al. .................. 435/4
2003/0211499 A1 * 11/2003 Reddy et al. .................. 435/6

FOREIGN PATENT DOCUMENTS

CN 1287170 3/2001
WO WO 02/062999 8/2002
WO WO 02/097031 * 12/2002
WO WO 2004/048598 11/2003
WO WO 2004/035732 4/2004

OTHER PUBLICATIONS

Accession No. AK014544, Mus musculus 0 day neonate skin cDNA, RIKEN full-length enriched library, clone:4632401C08 product, from http://www.ncbi.nlm.nih.gov, from Sep. 19, 2008, accessed Jul. 26, 2010.*
Accession No. AK028784, Mus musculus 10 days neonate skin cDNA, RIKEN full-length enriched library, clone:4732456G02 product, from http://www.ncbi.nlm.nih.gov, from Sep. 19, 2008, accessed Jul. 26, 2010.*
Accession No. AJ276207, Homo sapiens mRNA for orphan transporter XT3 (XT3 gene), from http://www.ncbi.nlm.nih.gov, from Oct. 21, 2008, accessed Jul. 26, 2010.*
Accession No. AAG64193, human nerve mass-transferring protein, from http://www.ebi.ac.uk/cgi-bin/epo/epofetch?AAG64193, accessed Mar. 23, 2005, from CN1287170-A, Mar. 14, 2001.*
Accession No. ADP29090, Human secreted protein encoding sequence SEQ ID #1088, from http://www.ebi.ac.uk/cgi-bin/epo/epofetch?ADP29090, from WO 2004/035,732, Apr. 29, 2004.*
Broer et al., Journal of Biological Chemistry, 279(23):24467-76, Jun. 4, 2004.*
Branden et al., A peptide nucleic acid-nuclearl ocalization signal fusion that mediates nuclear transport of DNA, Nature Biotechnology, vol. 17, pp. 784-787, 1999.
Rodrigues et al., Cardiomyopathy associated with carnitine loss in kidneys and small intestine, Eur. J. Pediatrics vol. 148, 1988, pp. 193-197, 1988.

* cited by examiner

*Primary Examiner*—Marianne P Allen

(57) ABSTRACT

The present invention is directed to a method of screening for a carnitine transporter agonist or for a carnitine transporter antagonist, to a kit for carrying out the method of screening for a carnitine transporter agonist or for a carnitine transporter antagonist, to a method for the manufacture of a medicament for the treatment of a carnitine transporter deficiency, to methods of diagnosis of a carnitine transporter deficiency, to the use of a protein for the manufacture of an antibody reacting with a carnitine transporter, to an oligonucleotide and to methods of treatment of a carnitine transporter deficiency.

8 Claims, 39 Drawing Sheets

Fig. 3

```
Mouse (SEQ ID NO:2), Rat  (SEQ ID NO:3) Human (human) (SEQ ID NO:1)

Mouse         MVRLVLPNPG LEERIPSLDE LEVIEKEEAG SRPKWDNKAQ YMLTCVGFCV
Rat           MVRLVLPNPG LEDRIPSLDE LEVIEKEEAS SKPKWDNKAQ YMLTCVGFCV
human         MVRLVLPNPG LDARIPSLAE LETIEQEEAS SRPKWDNKAQ YMLTCLGFCV Mouse         GLGNVWRFPY LCQSHGGGAF MIPFLILLVF EGIPLLYLEF AIGQRLRKGS
Rat           GLGNVWRFPY LCQSHGGGAF MIPFLILLVL EGIPLLHLEF AIGQRLRKGS
human         GLGNVWRFPY LCQSHGGGAF MIPFLILLVL EGIPLLYLEF AIGQRLRRGS Mouse         MGVWSSIHPA LKGIGIASMF VSFMVGLYYN TIIAWVMWYF FNSFQEPLPW
Rat           VGVWSSIHPA LKGVGIASMF VSFMVGLYYN TIIAWVMWYF FNSFQEPLPW
human         LGVWSSIHPA LKGLGLASML TSFMVGLYYN TIISWIMWYL FNSFQEPLPW Mouse         SECPLNQNQT GYVEECAKSS SVDYFWYRET LNISTSISDS GSIQWWILLC
Rat           SECPLNQNQT GYVEECAKSS SVDYFWYRET LNISTPISDS GSIQWWILLC
human         SDCPLNENQT GYVDECARSS PVDYFWYRET LNISTSISDS GSIQWWMLLC Mouse         LTCAWSVLYV CIIRGIETTG KAVYITSTLP YVVLTIFLIR GLTLKGATNG
Rat           LTCAWSVLYV CTIRGIETTG KAVYITSTLP YVVLTIFLIR GLTLKGATNG
human         LACAWSVLYM CTIRGIETTG KAVYITSTLP YVVLTIFLIR GLTLKGATNG Mouse         IVFLFTPNIT ELSNPNTWLD AGAQVFYSFS LAFGGLISFS SYNSVHNNCE
Rat           IVFLFTPNIT ELSNPNTWLD AGAQVYYSFS LAFGGLISFS SYNSVHNNCE
human         IVFLFTPNVT ELAQPDTWLD AGAQVFFSFS LAFGGLISFS SYNSVHNNCE Mouse         MDSVIVSVIN GFTSVYAATV VYSIIGFRAT ERFDDCVNTN ILTLINGFDL
Rat           MDSVIVSIIN GFTSVYAATV VYSIIGFRAT ERFDDCVNTN ILTLINGFDL
human         KDSVIVSIIN GFTSVYVAIV VYSVIGFRAT QRYDDCFSTN ILTLINGFDL Mouse         PEGNVTSENF EAYQQWCNAT NPQAYAQLKF QTCDINSFLS EGVEGTGLAF
Rat           PEGNVTAENF EAYQHWCNAT NPEAYAQLTF QTCDINTFLS EGVEGTGLAF
human         PEGNVTQENF VDMQQRCNAS DPAAYAQLVF QTCDINAFLS EAVEGTGLAF Mouse         IVFTEAITKM PVSPLWSVLF FIMLFCLGLS SMFGNMEGVV VPLQDLNITP
Rat           IVFTEAITKM PVSPLWSVLF FIMLFCLGLS SMFGNMEGVV VPLQDLNITP
human         IVFTEAITKM PLSPLWSVLF FIMLFCLGLS SMFGNMEGVV VPLQDLRVIP Mouse         KKWPKELLTG LICLGTYLIA FIFTLNSGQY WLSLLDSFAG SIPLLIIAFC
Rat           KKWPKELLTG LICLGTYLIA FIFTLNSGQY WLSLLDSYAG SIPLLIIAFC
human         PKWPKEVLTG LICLGTFLIG FIFTLNSGQY WLSLLDSYAG SIPLLIIAFC Mouse         EMFAVVYVYG VDRFNKDIEF MIGHKPNIFW QVTWRVVSPL IMLVIFLFFF
Rat           EMFAVVYVYG VDRFNKDIEF MIGHKPNIFW QVTWRVVSPL IMLVIFLFFF
human         EMFSVVYVYG VDRFNKDIEF MIGHKPNIFW QVTWRVVSPL LMLIIFLFFF Mouse         VIEVNKTLMY SIWDPNYEEF PKSQKIPYPN WVYAVVVTVA GVPCLSIPCF
Rat           VIEVNKQLMY SVWDPDYEEF PKSQKVPYPD WVYAVVVIVA GVPCLTIPCF
human         VVEVSQELTY SIWDPGYEEF PKSQKISYPN WVYVVVVIVA GVPSLTIPGY Mouse         AIYKFIRNCC QKSDDHHGLV NTLSTASVNG DLKN
Rat           AIYKLIRNYC QKSGDQHGLV NALSTASVNG DLKN
human         AIYKLIRNHC QKPGDHQGLV STLSTASMNG DLKY
```

Fig. 4A

```
SEQ ID NR: 1 x SEQ ID NR: 2
86,9 % identity
90,5 % similarity

1 MVRLVLPNPGLDARIPSLAELETIEQEEASSRPKWDNKAQYMLTCLGFCV 50
    |||||||||||:||||| ||| ||.||| ||||||||||||||||.||||
  1 MVRLVLPNPGLEERIPSLDELEVIEKEEAGSRPKWDNKAQYMLTCVGFCV 50

51 GLGNVWRFPYLCQSHGGGAFMIPFLILLVLEGIPLLYLEFAIGQRLRRGS 100
    ||||||||||||||||||||||||||||| ||||||||||||||||:||
 51 GLGNVWRFPYLCQSHGGGAFMIPFLILLVFEGIPLLYLEFAIGQRLRKGS 100

101 LGVWSSIHPALKGLGLASMLTSFMVGLYYNTIISWIMWYLFNSFQEPLPW 150
    :||||||||||:|:||| |||||||||||.|:||| ||||||||||||
101 MGVWSSIHPALKGIGIASMFVSFMVGLYYNTIIAWVMWYFFNSFQEPLPW 150

151 SDCPLNENQTGYVDECARSSPVDYFWYRETLNISTSISDSGSIQWWMLLC 200
    |:||||:|||||:|||:|||:|| ||||||||||||||||||||||.|||
151 SECPLNQNQTGYVEECAKSSSVDYFWYRETLNISTSISDSGSIQWWILLC 200

201 LACAWSVLYMCTIRGIETTGKAVYITSTLPYVVLTIFLIRGLTLKGATNG 250
    | |||||||.| ||||||||||||||||||||||||||||||||||||||
201 LTCAWSVLYVCIIRGIETTGKAVYITSTLPYVVLTIFLIRGLTLKGATNG 250

251 IVFLFTPNVTELAQPDTWLDAGAQVFFSFSLAFGGLISFSSYNSVHNNCE 300
    ||||||||:|||. |.||||||||||:||||||||||||||||||||||
251 IVFLFTPNITELSNPNTWLDAGAQVFYSFSLAFGGLISFSSYNSVHNNCE 300

301 KDSVIVSIINGFTSVYVAIVVYSVIGFRATQRYDDCFSTNILTLINGFDL 350
    ||||||:||||||| | ||||:|||||:|:||| .|||||||||||||
301 MDSVIVSVINGFTSVYAATVVYSIIGFRATERFDDCVNTNILTLINGFDL 350

351 PEGNVTQENFVDMQQRCNASDPAAYAQLVFQTCDINAFLSEAVEGTGLAF 400
    |||||| ||| || |||..| ||||| |||||||.|||| ||||||||
351 PEGNVTSENFEAYQQWCNATNPQAYAQLKFQTCDINSFLSEGVEGTGLAF 400

401 IVFTEAITKMPLSPLWSVLFFIMLFCLGLSSMFGNMEGVVVPLQDLRVIP 450
    ||||||||||.|||||||||||||||||||||||||||||||||||: |
401 IVFTEAITKMPVSPLWSVLFFIMLFCLGLSSMFGNMEGVVVPLQDLNITP 450

451 PKWPKEVLTGLICLGTFLIGFIFTLNSGQYWLSLLDSYAGSIPLLIIAFC 500
    |||||.|||||||||:|| |||||||||||||||||:||||||||||||
451 KKWPKELLTGLICLGTYLIAFIFTLNSGQYWLSLLDSFAGSIPLLIIAFC 500
```

Fig. 4B

```
501 ■M■SVVYVYGVDR■NKD■■■M■GHKPN■■WQV■WRVVSPLLML■■■L■■■ 550
    ■■■.■■■■■■■■■■■■■■■■■■■■■■■■■■■■■■■■■■■■■:■■:■■■■■■
501 ■M■AVVYVYGVDR■NKD■■■M■GHKPN■■WQV■WRVVSPL■MLV■■L■■■ 550

551 VV■VSQ■L■YS■WDPGY■■■PKSQK■SYPNWVYVVVV■VAGVPSL■■PGY 600
    ■:■■.. ■ ■■■■■■■ ■■■■■■■■■■ ■■■■■■ ■■■ ■■■■■ ■.■■ :
551 V■■VNK■LMYS■WDPNY■■■PKSQK■PYPNWVYAVVV■VAGVPCLS■PC■ 600

601 A■YKL■RNHCQKPGDHQGLVS■LS■ASMNGDLKY 634
    ■■■■ ■■■ ■■■    ■■ ■■■.■■■■■■.■■■■■
601 A■YK■■RNCCQKSDDHHGLVN■LS■ASVNGDLKN 634
```

Fig. 5A

```
SEQ ID NO: 1 x SEQ ID NO: 3
86,7 % identity
90,8 % similarity

1 MVRLVLPNPGLDARIPSLAELETIEQEEASSRPKWDNKAQYMLTCLGFCV  50
    ||||||||||:  ||||| ||| ||.|||||:|||||||||||||.||||
  1 MVRLVLPNPGLEDRIPSLDELEVIEKEEASSKPKWDNKAQYMLTCVGFCV  50

51 GLGNVWRFPYLCQSHGGGAFMIPFLILLVLEGIPLLYLEFAIGQRLRRGS 100
    |||||||||||||||||||||||||||||||||||:||||||||||:||
 51 GLGNVWRFPYLCQSHGGGAFMIPFLILLVLEGIPLLHLEFAIGQRLRKGS 100

101 LGVWSSIHPALKGLGLASMLTSFMVGLYYNTIISWIMWYLFNSFQEPLPW 150
    .||||||||||.|:||| ||||||||||||||.|:||| ||||||||||
101 VGVWSSIHPALKGVGIASMFVSFMVGLYYNTIIAWVMWYFFNSFQEPLPW 150

151 SDCPLNENQTGYVDECARSSPVDYFWYRETLNISTSISDSGSIQWWMLLC 200
    |:||||:|||||||:|||:|| |||||||||||||  |||||||||.||
151 SECPLNQNQTGYVEECAKSSSVDYFWYRETLNISTPISDSGSIQWWILLC 200

201 LACAWSVLYMCTIRGIETTGKAVYITSTLPYVVLTIFLIRGLTLKGATNG 250
    | |||||||.|||||||||||||||||||||||||||||||||||||||
201 LTCAWSVLYVCTIRGIETTGKAVYITSTLPYVVLTIFLIRGLTLKGATNG 250

251 IVFLFTPNVTELAQPDTWLDAGAQVFFSFSLAFGGLISFSSYNSVHNNCE 300
    ||||||||:|||. |.|||||||||::||||||||||||||||||||||
251 IVFLFTPNITELSNPNTWLDAGAQVYYSFSLAFGGLISFSSYNSVHNNCE 300

301 KDSVIVSIINGFTSVYVAIVVYSVIGFRATQRYDDCFSTNILTLINGFDL 350
    |||||||||||||| |  ||:|||||:|||||:|:|||  .||||||||
301 MDSVIVSIINGFTSVYAATVVYSIIGFRATERFDDCVNTNILTLINGFDL 350

351 PEGNVTQENFVDMQQRCNASDPAAYAQLVFQTCDINAFLSEAVEGTGLAF 400
    |||||| |||   |   |||..| ||||.||||||| |||.||||||||
351 PEGNVTAENFEAYQHWCNATNPEAYAQLTFQTCDINTFLSEGVEGTGLAF 400

401 IVFTEAITKMPLSPLWSVLFFIMLFCLGLSSMFGNMEGVVVPLQDLRVIP 450
    ||||||||||| |||||||||||||||||||||||||||||||||| :| 
401 IVFTEAITKMPVSPLWSVLFFIMLFCLGLSSMFGNMEGVVVPLQDLNITP 450

451 PKWPKEVLTGLICLGTFLIGFIFTLNSGQYWLSLLDSYAGSIPLLIIAFC 500
    ||||||.||||||||::|| |||||||||||||||||||||||||||||
451 KKWPKELLTGLICLGTYLIAFIFTLNSGQYWLSLLDSYAGSIPLLIIAFC 500
```

Fig. 5B

```
501 IMISVVYVYGVDRINKDIIIMIGHKPNIIWQVIWRVVSPLLMLIIILIII 550
    III.IIIIIIIIIIIIIIIIIIIIIIIIIIIIIIIIIII:II:IIIIII
501 IMIAVVYVYGVDRINKDIIIMIGHKPNIIWQVIWRVVSPLIMLVIILIII 550

551 VVIVSQILIYSIWDPGYIIIPKSQKISYPNWVYVVVVIVAGVPSLIIPGY 600
    I:II..:I  II:III  IIIIIIIII: II.III IIIIIIIII IIII :
551 VIIVNKQLMYSVWDPDYIIIPKSQKVPYPDWVYAVVVIVAGVPCLIIPCI 600

601 AIYKLIRNHCQKPGDHQGLVSILSIASMNGDLKY 634
    IIIIIIII:III II   III. IIIII.IIIII
601 AIYKLIRNYCQKSGDQHGLVNALSIASVNGDLKN 634
```

Fig. 6A

```
SEQ ID NO: 2 x SEQ ID NO: 3
95,4 % identity
97 % similarity

1 MVRLVLPNPGLEERIPSLDELEVIEKEEAGSRPKWDNKAQYMLTCVGFCV 50
    ||||||||||||:||||||||||||||| |:|||||||||||||||||||
  1 MVRLVLPNPGLEDRIPSLDELEVIEKEEASSKPKWDNKAQYMLTCVGFCV 50

51 GLGNVWRFPYLCQSHGGGAFMIPFLILLVFEGIPLLYLEFAIGQRLRKGS 100
    |||||||||||||||||||||||||||||:||||||:|||||||||||||
 51 GLGNVWRFPYLCQSHGGGAFMIPFLILLVLEGIPLLHLEFAIGQRLRKGS 100

101 MGVWSSIHPALKGIGIASMFVSFMVGLYYNTIIAWVMWYFFNSFQEPLPW 150
    .||||||||||||:||||||||||||||||||||||||||||||||||||
101 VGVWSSIHPALKGVGIASMFVSFMVGLYYNTIIAWVMWYFFNSFQEPLPW 150

151 SECPLNQNQTGYVEECAKSSSVDYFWYRETLNISTSISDSGSIQWWILLC 200
    ||||||||||||||||||||||||||||||||||| ||||||||||||||
151 SECPLNQNQTGYVEECAKSSSVDYFWYRETLNISTPISDSGSIQWWILLC 200

201 LTCAWSVLYVCIIRGIETTGKAVYITSTLPYVVLTIFLIRGLTLKGATNG 250
    |||||||||| |||||||||||||||||||||||||||||||||||||||
201 LTCAWSVLYVCTIRGIETTGKAVYITSTLPYVVLTIFLIRGLTLKGATNG 250

251 IVFLFTPNITELSNPNTWLDAGAQVFYSFSLAFGGLISFSSYNSVHNNCE 300
    |||||||||||||||||||||||||:||||||||||||||||||||||||
251 IVFLFTPNITELSNPNTWLDAGAQVYYSFSLAFGGLISFSSYNSVHNNCE 300

301 MDSVIVSVINGFTSVYAATVVYSIIGFRATERFDDCVNTNILTLINGFDL 350
    |||||||:||||||||||||||||||||||||||||||||||||||||||
301 MDSVIVSIINGFTSVYAATVVYSIIGFRATERFDDCVNTNILTLINGFDL 350

351 PEGNVTSENFEAYQQWCNATNPQAYAQLKFQTCDINSFLSEGVEGTGLAF 400
    ||||||.||||||| |||||||:||||| |||||||.|||||||||||||
351 PEGNVTAENFEAYQHWCNATNPEAYAQLTFQTCDINTFLSEGVEGTGLAF 400

401 IVFTEAITKMPVSPLWSVLFFIMLFCLGLSSMFGNMEGVVVPLQDLNITP 450
    ||||||||||||||||||||||||||||||||||||||||||||||||||
401 IVFTEAITKMPVSPLWSVLFFIMLFCLGLSSMFGNMEGVVVPLQDLNITP 450
```

Fig. 6B

```
451 KKWPK LL GL CLG YL A   LNSGQYWLSLLDS AGS PLL  A C 500
    ||||||||||||||||||||||||||||||||||||:|||||||||||
451 KKWPK LL GL CLG YL A   LNSGQYWLSLLDSYAGS PLL  A C 500

501  M AVVYVYGVDR NKD   M GHKPN  WQV WRVVS L MLV L   550
    |||||||||||||||||||||||||||||||||||||||||||||||||
501  M AVVYVYGVDR NKD   M GHKPN  WQV WRVVS L MLV L   550

551 V  VNK LMYS WDPNY   PKSQK  YPNWVYAVVV VAGV CLS  C  600
    ||||| ||||:|||.|||||||||||:|||.||||||| ||||||.||||
551 V  VNKQLMYSVWD DY   PKSQKV YP DWVYAVVV VAGV CL  C  600

601 A YK   RNCCQKSDDHHGLVN LS ASVNGDLKN 634
    |||| ||| |||| | ||||| ||||||||||||
601 A YKL RNYCQKSGDQHGLVNALS ASVNGDLKN 634
```

Fig. 7A

SEQ ID NO: 1 x SEQ ID NO: 10

```
  1 MVRLVLPNPGLDARIPSLAELETIEQEEASSRPKWDNKAQYMLTCLGFCVGLGNVWRFPY
    |||||||||||||||||||||||||||||||||||||||||||||||||||||||||||
  1 MVRLVLPNPGLDARIPSLAELETIEQEEASSRPKWDNKAQYMLTCLGFCVGLGNVWRFPY

61 LCQSHGGGAFMIPFLILLVLEGIPLLYLEFAIGQRLRRGSLGVWSSIHPALKGLGLASML
    |||||||||||||||||||||||||||||||||||||||||||||||||||||||||||
 61 LCQSHGGGAFMIPFLILLVLEGIPLLYLEFAIGQRLRRGSLGVWSSIHPALKGLGLASML

121 TSFMVGLYYNTIISWIMWYLFNSFQEPLPWSDCPLNENQTGYVDECARSSPVDYFWYRET
    |||||||||||||||||||||||||||||||||||||||||||||||||||||||||||
121 TSFMVGLYYNTIISWIMWYLFNSFQEPLPWSDCPLNENQTGYVDECARSSPVDYFWYRET

181 LNISTSISDSGSIQWWMLLCLACAWSVLYMCTIRGIETTGKAVYITSTLPYVVLTIFLIR
    |||||||||||||||||||||||||||||||||||||||||||||||||||||||||||
181 LNISTSISDSGSIQWWMLLCLACAWSVLYMCTIRGIETTGKAVYITSTLPYVVLTIFLIR

241 GLTLKGATNGIVFLFTPNVTELAQPDTWLDAGAQVFFSFSLAFGGLISFSSYNSVH----
    ||||||||||||||||||||||||||||||||||||||||||||||||||||||||
241 GLTLKGATNGIVFLFTPNVTELAQPDTWLDAGAQVFFSFSLAFGGLISFSSYNSVHGSAS

297 ------------------------------------NNCEKDSVIVSIINGFTSVYVAIVV
                                        ||||||||||||||||||||||||
301 HSWGWRSGRDADAALGCVLTWDLIASRHDTGLVCSNNCEKDSVIVSIINGFTSVYVAIVV

322 YSVIGFRATQRYDDCFSTNILTLINGFDLPEGNVTQENFVDMQQRCNASDPAAYAQLVFQ
    |||||||||||||||||||||||||||||||||||||||||||||||||||||||||||
361 YSVIGFRATQRYDDCFSTNILTLINGFDLPEGNVTQENFVDMQQRCNASDPAAYAQLVFQ

382 TCDINAFLSEAVEGTGLAFIVFTEAITKMPLSPLWSVLFFIMLFCLGLSSMFGNMEGVVV
    |||||||||||||||||||||||||||||||||||||||||||||||||||||||||||
421 TCDINAFLSEAVEGTGLAFIVFTEAITKMPLSPLWSVLFFIMLFCLGLSSMFGNMEGVVV
```

Fig. 7B

```
442 PLQDLRVIPPKWPKEVLTGLICLGTFLIGFIFTLNSGQYWLSLLDSYAGSIPLLIIAFCE
    ||||||||||||||||||||||||||||||||||||||||||||||||||||||||||||
481 PLQDLRVIPPKWPKEVLTGLICLGTFLIGFIFTLNSGQYWLSLLDSYAGSIPLLIIAFCE

502 MFSVVYVYGVDRFNKDIEFMIGHKPNIFWQVTWRVVSPLLMLIIFLFFFVVEVSQELTYS
    ||||||||||||||||||||||||||||||||||||||||||||||||||||||||||||
541 MFSVVYVYGVDRFNKDIEFMIGHKPNIFWQVTWRVVSPLLMLIIFLFFFVVEVSQELTYS

562 IWDPGYEEFPKSQKISYPNWVYVVVVIVAGVPSLTIPGYAIYKLIRNHCQKPGDHQGLVS
    ||||||||||||||||||||||||||||||||||||||||||||||||||||||||||||
601 IWDPGYEEFPKSQKISYPNWVYVVVVIVAGVPSLTIPGYAIYKLIRNHCQKPGDHQGLVS

622 TLSTASMNGDLKY* 635
    |||||||||||||
661 TLSTASMNGDLKY- 673
```

Fig. 8A

SEQ ID NO: 4 x SEQ ID NO: 9

```
  1 ATGGTGAGGCTCGTGCTGCCCAACCCCGGCCTAGACGCCCGGATCCCGTC  50
    ||||||||||||||||||||||||||||||||||||||||||||||||||
  1 atggtgaggctcgtgctgcccaaccccggcctagacgcccggatcccgtc  50

51 CCTGGCTGAGCTGGAGACCATCGAGCAGGAGGAGGCCAGCTCCCGGCCGA 100
    ||||||||||||||||||||||||||||||||||||||||||||||||||
 51 cctggctgagctggagaccatcgagcaggaggaggccagctcccggccga 100

101 AGTGGGACAACAAGGCGCAGTACATGCTCACCTGCCTGGGCTTCTGCGTG 150
    ||||||||||||||||||||||||||||||||||||||||||||||||||
101 agtgggacaacaaggcgcagtacatgctcacctgcctgggcttctgcgtg 150

151 GGCCTCGGCAACGTGTGGCGCTTCCCCTACCTGTGTCAGAGCCACGGAGG 200
    ||||||||||||||||||||||||||||||||||||||||||||||||||
151 ggcctcggcaacgtgtggcgcttcccctacctgtgtcagagccacggagg 200

201 AGGAGCCTTCATGATCCCGTTCCTCATCCTGCTGGTCCTGGAGGGCATCC 250
    ||||||||||||||||||||||||||||||||||||||||||||||||||
201 aggagccttcatgatcccgttcctcatcctgctggtcctggagggcatcc 250

251 CCCTGCTGTACCTGGAGTTCGCCATCGGGCAGCGGCTGCGGCGGGGCAGC 300
    ||||||||||||||||||||||||||||||||||||||||||||||||||
251 ccctgctgtacctggagttcgccatcgggcagcggctgcggcggggcagc 300

301 CTGGGTGTGTGGAGCTCCATCCACCCGGCCCTGAAGGGCCTAGGCCTGGC 350
    ||||||||||||||||||||||||||||||||||||||||||||||||||
301 ctgggtgtgtggagctccatccacccggccctgaagggcctaggcctggc 350

351 CTCCATGCTCACGTCCTTCATGGTGGGACTGTATTACAACACCATCATCT 400
    ||||||||||||||||||||||||||||||||||||||||||||||||||
351 ctccatgctcacgtccttcatggtgggactgtattacaacaccatcatct 400

401 CCTGGATCATGTGGTACTTATTCAACTCCTTCCAGGAGCCTCTGCCCTGG 450
    ||||||||||||||||||||||||||||||||||||||||||||||||||
401 cctggatcatgtggtacttattcaactccttccaggagcctctgccctgg 450

451 AGCGACTGCCCGCTCAACGAGAACCAGACAGGGTATGTGGACGAGTGCGC 500
    ||||||||||||||||||||||||||||||||||||||||||||||||||
```

Fig. 8B

```
 451 agcgactgcccgctcaacgagaaccagacagggtatgtggacgagtgcgc  500
             .         .         .         .         .
 501 CAGGAGCTCCCCTGTGGACTACTTCTGGTACCGAGAGACGCTCAACATCT  550
     |||||||||||||||||||||||||||||||||||||||||||||||||
 501 caggagctcccctgtggactacttctggtaccgagagacgctcaacatct  550
             .         .         .         .         .
 551 CCACGTCCATCAGCGACTCGGGCTCCATCCAGTGGTGGATGCTGCTGTGC  600
     |||||||||||||||||||||||||||||||||||||||||||||||||
 551 ccacgtccatcagcgactcgggctccatccagtggtggatgctgctgtgc  600
             .         .         .         .         .
 601 CTGGCCTGCGCATGGAGCGTCCTGTACATGTGCACCATCCGCGGCATCGA  650
     |||||||||||||||||||||||||||||||||||||||||||||||||
 601 ctggcctgcgcatggagcgtcctgtacatgtgcaccatccgcggcatcga  650
             .         .         .         .         .
 651 GACCACCGGGAAGGCCGTGTACATCACCTCCACGCTGCCCTATGTCGTCC  700
     |||||||||||||||||||||||||||||||||||||||||||||||||
 651 gaccaccgggaaggccgtgtacatcacctccacgctgccctatgtcgtcc  700
             .         .         .         .         .
 701 TGACCATCTTCCTCATCCGAGGCCTGACGCTGAAGGGCGCCACCAATGGC  750
     |||||||||||||||||||||||||||||||||||||||||||||||||
 701 tgaccatcttcctcatccgaggcctgacgctgaagggcgccaccaatggc  750
             .         .         .         .         .
 751 ATCGTCTTCCTCTTCACGCCCAACGTCACGGAGCTGGCCCAGCCGGACAC  800
     |||||||||||||||||||||||||||||||||||||||||||||||||
 751 atcgtcttcctcttcacgcccaacgtcacggagctggcccagccggacac  800
             .         .         .         .         .
 801 CTGGCTGGACGCGGGCGCACAGGTCTTCTTCTCCTTCTCCCTGGCCTTCG  850
     |||||||||||||||||||||||||||||||||||||||||||||||||
 801 ctggctggacgcgggcgcacaggtcttcttctccttctccctggccttcg  850
             .         .         .         .         .
 851 GGGGCCTCATCTCCTTCTCCAGCTACAACTCTGTGCA.............  887
     ||||||||||||||||||||||||||||||||||||
 851 ggggcctcatctccttctccagctacaactctgtgcatggctcagcctct  900
                                                  .
                                                  .
                                                  .
 888 ....CAACAACTGCGAGAAGGACTCGGTGATTGTGTCCATCATCAACGGC  933
         |||||||||||||||||||||||||||||||||||||||||||||
1001 gcagcaacaactgcgagaaggactcggtgattgtgtccatcatcaacggc 1050
             .         .         .         .         .
 934 TTCACATCGGTGTATGTGGCCATCGTGGTCTACTCCGTCATTGGGTTCCG  983
     |||||||||||||||||||||||||||||||||||||||||||||||||
1051 ttcacatcggtgtatgtggccatcgtggtctactccgtcattgggttccg 1100
```

Fig. 8C

```
 984 CGCCACGCAGCGCTACGACGACTGCTTCAGCACGAACATCCTGACCCTCA 1033
     ||||||  |||||||||||||||||||||||||||||||||||||||||
1101 cgccacacagcgctacgacgactgcttcagcacgaacatcctgaccctca 1150

1034 TCAACGGGTTCGACCTGCCTGAAGGCAACGTGACCCAGGAGAACTTTGTG 1083
     ||||||||||||||||||||||||||||||||||||||||||||||||||
1151 tcaacgggttcgacctgcctgaaggcaacgtgacccaggagaactttgtg 1200

1084 GACATGCAGCAGCGGTGCAACGCCTCCGACCCCGCGGCCTACGCGCAGCT 1133
     ||||||||||||||||||||||||||||||||||||||||||||||||||
1201 gacatgcagcagcggtgcaacgcctccgaccccgcggcctacgcgcagct 1250

1134 GGTGTTCCAGACCTGCGACATCAACGCCTTCCTCTCAGAGGCCGTGGAGG 1183
     ||||||||||||||||||||||||||||||||||||||||||||||||||
1251 ggtgttccagacctgcgacatcaacgccttcctctcagaggccgtggagg 1300

1184 GCACAGGCCTGGCCTTCATCGTCTTCACCGAGGCCATCACCAAGATGCCG 1233
     ||||||||||||||||||||||||||||||||||||||||||||||||||
1301 gcacaggcctggccttcatcgtcttcaccgaggccatcaccaagatgccg 1350

1234 TTGTCCCCACTGTGGTCTGTGCTCTTCTTCATTATGCTCTTCTGCCTGGG 1283
     ||||||||||||||||||||||||||||||||||||||||||||||||||
1351 ttgtccccactgtggtctgtgctcttcttcattatgctcttctgcctggg 1400

1284 GCTGTCATCTATGTTTGGGAACATGGAGGGCGTCGTTGTGCCCCTGCAGG 1333
     ||||||||||||||||||||||||||||||||||||||||||||||||||
1401 gctgtcatctatgtttgggaacatggagggcgtcgttgtgcccctgcagg 1450

1334 ACCTCAGAGTCATCCCCCCGAAGTGGCCCAAGGAGGTGCTCACAGGCCTC 1383
     ||||||||||||||||||||||||||||||||||||||||||||||||||
1451 acctcagagtcatccccccgaagtggcccaaggaggtgctcacaggcctc 1500

1384 ATCTGCCTGGGGACATTCCTCATTGGCTTCATCTTCACGCTGAACTCCGG 1433
     ||||||||||||||||||||||||||||||||||||||||||||||||||
1501 atctgcctggggacattcctcattggcttcatcttcacgctgaactccgg 1550

1434 CCAGTACTGGCTCTCCCTGCTGGACAGCTATGCCGGCTCCATTCCCCTGC 1483
     ||||||||||||||||||||||||||||||||||||||||||||||||||
1551 ccagtactggctctccctgctggacagctatgccggctccattcccctgc 1600

1484 TCATCATCGCCTTCTGCGAGATGTTCTCTGTGGTCTACGTGTACGGTGTG 1533
     ||||||||||||||||||||||||||||||||||||||||||||||||||
1601 tcatcatcgccttctgcgagatgttctctgtggtctacgtgtacggtgtg 1650
```

Fig. 8D

```
1534 GACAGGTTCAATAAGGACATCGAGTTCATGATCGGCCACAAGCCCAACAT 1583
     ||||||||||||||||||||||||||||||||||||||||||||||||||
1651 gacaggttcaataaggacatcgagttcatgatcggccacaagcccaacat 1700

1584 CTTCTGGCAAGTCACGTGGCGCGTGGTCAGCCCCCTGCTCATGCTGAtca 1633
     ||||||||||||||||||||||||||||||||||||||||||||||||||
1701 cttctggcaagtcacgtggcgcgtggtcagcccctgctcatgctgatca 1750

1634 tcttcctcttcttcttcgtGGTAGAGGTCAGTCAGGAGCTGACCTACAGC 1683
     ||||||||||||||||||||||||||||||||||||||||||||||||||
1751 tcttcctcttcttcttcgtggtagaggtcagtcaggagctgacctacagc 1800

1684 ATCTGGGACCCTGGCTACGAGGAATTTCCCAAATCCCAGAAGATCTCCTA 1733
     ||||||||||||||||||||||||||||||||||||||||||||||||||
1801 atctgggaccctggctacgaggaatttcccaaatcccagaagatctccta 1850

1734 CCCGAACTGGGTGTATGTGGTGGTGGTGATTGTGGCTGGAGTGCCCTCCC 1783
     ||||||||||||||||||||||||||||||||||||||||||||||||||
1851 cccgaactgggtgtatgtggtggtggtgattgtggctggagtgccctccc 1900

1784 TCACCATCCCTGGCTATGCCATCTACAAGCTCATCAGGAACCACTGCCAG 1833
     ||||||||||||||||||||||||||||||||||||||||||||||||||
1901 tcaccatccctggctatgccatctacaagctcatcaggaaccactgccag 1950

1834 AAGCCAGGGGACCATCAGGGGCTGGTGAGCACACTGTCCACAGCCTCCAT 1883
     ||||||||||||||||||||||||||||||||||||||||||||||||||
1951 aagccaggggaccatcaggggctggtgagcacactgtccacagcctccat 2000

1884 GAACGGGGACCTGAAGTACTGA 1905
     ||||||||||||||||||||||
2001 gaacggggacctgaagtactga 2022
```

Figure 9A

```
atggtgaggc ttgtgctgcc caaccctggc ctagaggagc ggattccatc tctggatgag    60
ttagaggtca ttgaaaagga agaggccggc tccaggccca aatgggacaa caaggcccag   120
tacatgctca cctgtgtggg cttttgtgtg gggctgggca acgtgtggcg cttcccctac   180
ctatgccaga gccatggagg aggggccttc atgatcccat cctcatcct tctggtgttc    240 gagggaattc ctttgctgta cctggagttt gccatcggtc agaggctacg caagggcagc   300
atgggtgtgt ggagctccat ccaccctgct ctgaagggta taggcatcgc ctccatgttc   360
gtgtccttca tggtgggcct gtactacaac accatcatcg cctgggtcat gtggtacttc   420
ttcaactcct ttcaggaacc tctgccatgg agtgaatgtc cactcaacca gaaccagaca   480
ggctatgtgg aagagtgtgc caagagctct tccgtggact acttctggta ccgagagact   540
cttaatatct ccacttccat cagtgactca ggctccatcc agtggtggat cctgctctgc   600
ctgacatgtg cctggagtgt gctgtatgtg tgtattatcc gtggcatcga gaccactggg   660
aaggctgtgt acatcacctc caccctgccc tatgttgtac tgaccatctt tctcatccgt   720
ggcttgactc tgaagggtgc caccaacggc attgtcttcc ttttcacacc caatatcaca   780
gagctgagca ccccaacac gtggctggat gcaggtgctc aggtcttcta ctccttctca   840
ctggccttcg ggggcctcat ctccttctcc agctacaact ctgtgcacaa taattgtgag   900
atggattctg tgatcgtgtc tgtcatcaat ggcttcacat ctgtgtatgc ggccaccgtg   960
gtctactcca tcattggctt ccgagccact gagcgctttg atgactgtgt caacacgaac  1020
atcctgaccc tcatcaatgg gttcgacctg ccggagggca atgtgacttc agagaacttt  1080
gaggcctacc aacagtggtg caatgccact aatccccagg cctatgcaca actgaagttt  1140
cagacctgtg acattaacag cttcctttct gagggtgtgg agggcacagg cctggccttc  1200
attgtcttca cggaagccat cacgaagatg ccagtgtccc cactgtggtc ggtgctcttt  1260
tttataatgc tcttctgcct gggactctcc tccatgtttg gaacatgga gggtgtggtc  1320
```

Fig. 9B

```
gtaccccttc aggacctcaa tatcacccct aagaagtggc ccaaagaatt gttgacaggc    1380
ctcatctgct tggggacata tctcatcgcc ttcattttca cactgaattc gggccagtac    1440
tggctctctc tcctggacag ctttgctggc tccattcctc tgctaatcat cgccttttgt    1500
gagatgtttg ccgtcgtcta cgtgtatgga gttgacaggt tcaacaagga catcgagttc    1560
atgatcggcc ataagcccaa catcttctgg caagtcacgt ggagagtggt cagtccactg    1620
atcatgctgg tcatcttcct cttcttttt gtgattgagg tcaacaaaac gctcatgtat    1680
agcatctggg accctaacta tgaggagttc ccgaaatctc agaagattcc ataccccaac    1740
tgggtgtatg cagttgtggt cactgtggct ggagtaccct gcctctccat cccctgcttt    1800
gccatctaca agttcatcag aaattgttgt cagaagtctg atgaccacca tgggctggtc    1860
aatacactgt ccacagcctc tgtgaatggg gaccttaaga actga                    1905
```

(SEQ Id NO 5)

Figure 10

5'-accatggtga ggctcgtg-3'          (SEQ ID NO: 6)

5'-gtgtcaggga aggaggaacc ag-3'     (SEQ ID NO: 7)

Figure 11A

| | | | | | |
|---|---|---|---|---|---|
| atggtgaggc | ttgtgctacc | caaccctggc | ctagaggacc | ggattccgtc | tctggatgaa | 60 |
| ttagaggtca | ttgaaaagga | agaggccagc | tccaagccca | aatgggacaa | caaggcccag | 120 |
| tacatgctca | cctgtgtggg | cttctgtgtg | gggctgggca | atgtctggcg | cttcccttac | 180 |
| ctgtgccaga | gccatggagg | aggggccttc | atgatcccct | tcctcatcct | tctggtcctg | 240 |
| gagggcattc | ccttgctgca | cctggagttt | gccatcggac | agaggctacg | caagggcagt | 300 |
| gtgggcgtct | ggagctccat | ccaccctgct | ctgaagggtg | taggcatcgc | ctccatgttc | 360 |
| gtgtccttca | tggtgggcct | gtactacaac | accatcatcg | cctgggtcat | gtggtatttc | 420 |
| ttcaactcct | ttcaggaacc | tctgccatgg | agcgaatgcc | cactcaacca | gaaccagaca | 480 |
| ggctatgtgg | aagagtgtgc | caagagctct | tctgtggact | acttctggta | ccgagagact | 540 |
| ctcaacatct | ccactcctat | cagtgactca | ggctccatcc | agtggtggat | cctgctctgc | 600 |
| ctgacatgtg | cctggagtgt | tctgtatgtg | tgtactatcc | gtggcatcga | gaccactggg | 660 |
| aaggctgttt | acatcacctc | caccctgccc | tatgtcgtac | tgaccatctt | tctcatccgt | 720 |
| ggcttgactc | tgaagggtgc | caccaacggc | attgtcttcc | ttttcacacc | caatatcaca | 780 |
| gagctgagca | accccaacac | gtggctggat | gcaggtgctc | aggtttacta | ctccttctca | 840 |
| ctggccttcg | ggggcctcat | ctccttctcc | agctacaact | ctgtacacaa | taattgtgag | 900 |
| atggattccg | tgatcgtgtc | catcatcaat | ggcttcacat | ctgtgtatgc | ggccaccgtg | 960 |
| gtctactcta | tcattggctt | cagggccacc | gagcgctttg | atgactgtgt | gaacacgaac | 1020 |
| atcctgaccc | tcatcaatgg | gttcgacctg | cccagggca | atgtgactgc | ggagaacttc | 1080 |
| gaggcctatc | aacattggtg | caatgccact | aatcccgagg | cctatgccca | gctgacgttt | 1140 |
| cagacctgtg | acattaacac | cttcctctct | gagggtgtag | agggcacagg | cctggccttc | 1200 |
| attgtcttca | ctgaagccat | cacgaagatg | ccagtgtccc | cactgtggtc | ggtgctcttc | 1260 |
| tttatcatgc | tcttctgcct | gggcctctcc | tctatgtttg | ggaacatgga | gggtgtggtc | 1320 |

Fig. 11B

```
gtacccttc aggatctcaa tatcacccct aagaagtggc ccaaagaact gctcacaggt    1380
ctcatctgct tggggacata tctcatcgcc ttcattttca cactgaattc gggccagtac    1440
tggctctccc tgctggacag ctatgctggc tccatccctc tgctaatcat cgccttttgt    1500
gagatgtttg ctgtcgtcta cgtgtatgga gttgacaggt tcaacaagga catcgagttc    1560
atgatcggcc ataagcccaa catcttctgg caagtcacgt ggagagtggt cagtccgctg    1620
atcatgctgg tcatcttcct cttctttttc gtgattgaag tcaacaaaca gctcatgtat    1680
agcgtatggg accctgacta tgaggagttc ccgaaatctc agaaggttcc atacccccgac   1740 tgggtgtacg cagttgtggt cattgtggct ggagtaccct gccttaccat cccctgcttt    1800
gccatctaca aactcatcag aaactattgc cagaagtctg gggaccaaca tgggctggtc    1860
aatgcgctgt ccacagcctc tgtgaatggg gaccttaaga actga                    1905
```

(SEQ ID NO: 8)

Figure 12A

| | | | | | | |
|---|---|---|---|---|---|---|
| gcggcccagg | cccgcaacct | tccctggtcg | tgcgccctat | gtaaggccag | ccgcggcagg | 60 |
| accaaggcgg | cggtgtcagc | tcgcgagcct | accctccgcg | gacggtcttg | ggtcgcctgc | 120 |
| tgcctggctt | gcctggtcgg | cggcgggtgc | ccgcgcgca | cgcgcaaagc | ccgccgcgtt | 180 |
| ccccgacccc | aggccgcgct | ctgtgggcct | ctgagggcgg | catgcgggac | tacgacgagg | 240 |
| tgaccgcctt | cctgggcgag | tgggggccct | tccagcgcct | catcttcttc | ctgctcagcg | 300 |
| ccagcatcat | ccccaatggc | ttcaccggcc | tgtcctccgt | gttcctgata | gcgaccccgg | 360 |
| agcaccgctg | ccgggtgccg | gacgccgcga | acctgagcag | cgcctggcgc | aaccacactg | 420 |
| tcccactgcg | gctgcgggac | ggccgcgagg | tgccccacag | ctgccgccgc | taccggctcg | 480 |
| ccaccatcgc | caacttctcg | gcgcttgggc | tggagccggg | gcgcgacgtg | gacctggggc | 540 |
| agctggagca | ggagagctgt | ctggatggct | gggagttcag | tcaggacgtc | tacctgtcca | 600 |
| ccattgtgac | cgagtggaac | ctggtgtgtg | aggacgactg | gaaggcccca | ctcacaatct | 660 |
| ccttgttctt | cgtgggtgtg | ctgttgggct | ccttcatttc | agggcagctg | tcagacaggt | 720 |
| ttggccggaa | gaatgtgctg | ttcgtgacca | tgggcatgca | gacaggcttc | agcttcctgc | 780 |
| agatcttctc | gaagaatttt | gagatgtttg | tcgtgctgtt | tgtccttgta | ggcatgggcc | 840 |
| agatctccaa | ctatgtggca | gcatttgtcc | tggggacaga | aattcttggc | aagtcagttc | 900 |
| gtataatatt | ctctacgtta | ggagtgtgca | tattttatgc | atttggctac | atggtgctgc | 960 |
| cactgtttgc | ttacttcatc | cgagactggc | ggatgctgct | ggtggcgctg | acgatgccgg | 1020 |
| gggtgctatg | cgtggcactc | tggtggttca | tccctgagtc | ccccgatgg | ctcatctctc | 1080 |
| agggacgatt | tgaagaggca | gaggtgatca | tccgcaaggc | tgccaaagcc | aatgggattg | 1140 |
| ttgtgccttc | cactatcttt | gacccgagtg | agttacaaga | cctaagttcc | aagaagcagc | 1200 |
| agtcccacaa | cattctggat | ctgcttcgaa | cctggaatat | ccggatggtc | accatcatgt | 1260 |
| ccataatgct | gtggatgacc | atatcagtgg | gctattttgg | gctttcgctt | gatactccta | 1320 |

Fig. 12B

```
acttgcatgg ggacatcttt gtgaactgct tcctttcagc gatggttgaa gtcccagcat    1380
atgtgttggc ctggctgctg ctgcaatatt tgccccggcg ctattccatg gccactgccc    1440
tcttcctggg tggcagtgtc cttctcttca tgcagctggt accccagac ttgtattatt     1500 tggctacagt cctggtgatg gtgggcaagt ttggagtcac ggctgccttt tccatggtct    1560
acgtgtacac agccgagctg tatcccacag tggtgagaaa catgggtgtg ggagtcagct    1620
ccacagcatc ccgcctgggc agcatcctgt ctccctactt cgtttacctt ggtgcctacg    1680
accgcttcct gccctacatt ctcatgggaa gtctgaccat cctgacagcc atcctcacct    1740
tgtttctccc agagagcttc ggtaccccac tcccagacac cattgaccag atgctaagag    1800
tcaaaggaat gaaacacaga aaaactccaa gtcacacaag gatgttaaaa gatggtcaag    1860
aaaggcccac aatccttaaa agcacagcct tctaacatcg cttccagtaa gggagaaact    1920
gaagaggaaa gactgtcttg ccagaaatgg ccagcttgtg cagactccga gtccttcagt    1980
gacaaaggcc tttgctgttt gtcctcttga cctgtgtctg acttgctcct ggatgggcac    2040
ccacactcag aggctacata tggccctaga gcaccacctt cctctaggga cactggggct    2100
acctacagac aacttcatct aagtcctaac tattacaatg atggactcag cacctccaaa    2160
gcagttaatt tttcactaga accagtgaga tctggaggaa tgtgagaagc atatgctaaa    2220
tgtacatttt aattttagac tacttgaaaa ggccctaat aaggctagag gtctaagtcc      2280
cccaccccct tccccactcc cctctagtgg tgaactttag aggaaaagga agtaattgca    2340
caaggagttt gattcttacc ttttctcagt tacagaggac attaactgga tcattgcttc    2400
cccagggcag gagagcgcag agctagggaa agtgaaaggt aatgaagatg agcagaatg     2460 agcagatgca gatcaccagc aaagtgcact gatgtgtgag ctcttaagac cactcagcat    2520
gacgactgag tagacttgtt tacatctgat caaagcactg ggcttgtcca ggctcataat    2580
aaatgctcca ttgaatctac tattcttgtt ttccactgct gtggaaacct ccttgctact    2640
```

Fig. 12C

```
atagcgtctt atgtatggtt taaaggaaat ttatcaggtg agagagatga gcaacgttgt    2700
cttttctctc aaagctgtaa tgtgggtttt gttttattgt ttatttgttt gttgttgtat    2760 cctttctcc ttgttatttg cccttcagaa tgcacttggg aaaggctggt tccttagcct     2820
```
(cctttttctcc  ttgttatttg  cccttcagaa  tgcacttggg  aaaggctggt  tccttagcct   2820)
```
cctggtttgt gtctttttt tttttttttt aaacacagaa tcactctggc aattgtctgc    2880
agctgccact ggtgcaaggc cttaccagcc ctagcctcta gcacttctct aagtgccaaa    2940
aacagtgtca ttgtgtgtgt tcctttcttg atacttagtc atgggaggat attacaaaaa    3000
agaaatttaa attgtgttca tagtctttca gagtagctca ctttagtcct gtaactttat    3060
tgggtgatat tttgtgttca gtgtaattgt cttctctttg ctgattatgt taccatggta   3120
ctcctaaagc atatgcctca cctggttaaa aaagaacaaa catgttttg tgaaagctac    3180 tgaagtgcct tgggaaatga gaaagtttta ataagtaaaa tgattttta aatatcaaaa    3240 aaaaaaaaaa aa                                                         3252
```

(SEQ ID NO 11)

Figure 13A

```
Met Arg Asp Tyr Asp Glu Val Thr Ala Phe Leu Gly Glu Trp Gly Pro
1               5                   10                  15

Phe Gln Arg Leu Ile Phe Phe Leu Leu Ser Ala Ser Ile Ile Pro Asn
            20              25              30

Gly Phe Thr Gly Leu Ser Ser Val Phe Leu Ile Ala Thr Pro Glu His
            35              40              45

Arg Cys Arg Val Pro Asp Ala Ala Asn Leu Ser Ser Ala Trp Arg Asn
50                      55                  60

His Thr Val Pro Leu Arg Leu Arg Asp Gly Arg Glu Val Pro His Ser
65                  70              75                      80

Cys Arg Arg Tyr Arg Leu Ala Thr Ile Ala Asn Phe Ser Ala Leu Gly
                85              90              95

Leu Glu Pro Gly Arg Asp Val Asp Leu Gly Gln Leu Glu Gln Glu Ser
            100             105             110

Cys Leu Asp Gly Trp Glu Phe Ser Gln Asp Val Tyr Leu Ser Thr Ile
            115             120             125

Val Thr Glu Trp Asn Leu Val Cys Glu Asp Asp Trp Lys Ala Pro Leu
            130             135             140

Thr Ile Ser Leu Phe Phe Val Gly Val Leu Leu Gly Ser Phe Ile Ser
145             150             155                     160

Gly Gln Leu Ser Asp Arg Phe Gly Arg Lys Asn Val Leu Phe Val Thr
                165             170             175
```

Fig. 13B

```
Met Gly Met Gln Thr Gly Phe Ser Phe Leu Gln Ile Phe Ser Lys Asn
            180                 185                 190

Phe Glu Met Phe Val Val Leu Phe Val Leu Val Gly Met Gly Gln Ile
        195                 200                 205

Ser Asn Tyr Val Ala Ala Phe Val Leu Gly Thr Glu Ile Leu Gly Lys
        210                 215                 220

Ser Val Arg Ile Ile Phe Ser Thr Leu Gly Val Cys Ile Phe Tyr Ala
225                 230                 235                 240

Phe Gly Tyr Met Val Leu Pro Leu Phe Ala Tyr Phe Ile Arg Asp Trp
                245                 250                 255

Arg Met Leu Leu Val Ala Leu Thr Met Pro Gly Val Leu Cys Val Ala
                260                 265                 270

Leu Trp Trp Phe Ile Pro Glu Ser Pro Arg Trp Leu Ile Ser Gln Gly
            275                 280                 285

Arg Phe Glu Glu Ala Glu Val Ile Ile Arg Lys Ala Ala Lys Ala Asn
            290                 295                 300

Gly Ile Val Val Pro Ser Thr Ile Phe Asp Pro Ser Glu Leu Gln Asp
305                 310                 315                 320

Leu Ser Ser Lys Lys Gln Gln Ser His Asn Ile Leu Asp Leu Leu Arg
                325                 330                 335

Thr Trp Asn Ile Arg Met Val Thr Ile Met Ser Ile Met Leu Trp Met
                340                 345                 350
```

Fig. 13C

```
Thr Ile Ser Val Gly Tyr Phe Gly Leu Ser Leu Asp Thr Pro Asn Leu
        355                 360                 365

His Gly Asp Ile Phe Val Asn Cys Phe Leu Ser Ala Met Val Glu Val
        370                 375                 380

Pro Ala Tyr Val Leu Ala Trp Leu Leu Leu Gln Tyr Leu Pro Arg Arg
385                 390                 395                 400

Tyr Ser Met Ala Thr Ala Leu Phe Leu Gly Gly Ser Val Leu Leu Phe
                405                 410                 415

Met Gln Leu Val Pro Pro Asp Leu Tyr Tyr Leu Ala Thr Val Leu Val
                420                 425                 430

Met Val Gly Lys Phe Gly Val Thr Ala Ala Phe Ser Met Val Tyr Val
                435                 440                 445

Tyr Thr Ala Glu Leu Tyr Pro Thr Val Val Arg Asn Met Gly Val Gly
                450                 455                 460

Val Ser Ser Thr Ala Ser Arg Leu Gly Ser Ile Leu Ser Pro Tyr Phe
465                 470                 475                 480

Val Tyr Leu Gly Ala Tyr Asp Arg Phe Leu Pro Tyr Ile Leu Met Gly
                485                 490                 495

Ser Leu Thr Ile Leu Thr Ala Ile Leu Thr Leu Phe Leu Pro Glu Ser
                500                 505                 510

Phe Gly Thr Pro Leu Pro Asp Thr Ile Asp Gln Met Leu Arg Val Lys
                515                 520                 525
```

Fig. 13D

```
Gly Met Lys His Arg Lys Thr Pro Ser His Thr Arg Met Leu Lys Asp
    530                 535                 540

Gly Gln Glu Arg Pro Thr Ile Leu Lys Ser Thr Ala Phe
545             550                 555

(SEQ ID NO 12)
```

Figure 14A

| | | | | | | |
|---|---|---|---|---|---|---|
| ggggcggggc | gcgctacccg | cagccccggg | agctcggcta | actcggcgcc | cagtgcacgg | 60 |
| ccgcaccatg | gggtcccgcc | acttcgaggg | gatttatgac | cacgtggggc | acttcggcag | 120 |
| attccagaga | gtcctctatt | tcatatgtgc | cttccagaac | atctcttgtg | gtattcacta | 180 |
| cttggcttct | gtgttcatgg | gagtcacccc | tcatcatgtc | tgcaggcccc | caggcaatgt | 240 |
| gagtcaggtt | gttttccata | atcactctaa | ttggagtttg | gaggacaccg | gggccctgtt | 300 |
| gtcttcaggc | cagaaagatt | atgttacggt | gcagttgcag | aatggtgaga | tctgggagct | 360 |
| ctcaaggtgt | agcaggaata | agagggagaa | cacatcgagt | ttgggctatg | aatacactgg | 420 |
| cagtaagaaa | gagtttcctt | gtgtggatgg | ctacatatat | gaccagaaca | catggaaaag | 480 |
| cactgcggtg | acccagtgga | acctggtctg | tgaccgaaaa | tggcttgcaa | tgctgatcca | 540 |
| gccctatttt | atgtttggag | tcctactggg | atcggtgact | tttggctact | tttctgacag | 600 |
| gctaggacgc | cgggtggtct | tgtgggccac | aagcagtagc | atgtttttgt | ttggaatagc | 660 |
| agcggcgttt | gcagttgatt | attcaccctt | catggctgct | cgcttttttc | ttgccatggt | 720 |
| tgcaagtggc | tatcttgtgg | tggggtttgt | ctatgtgatg | gaattcattg | gcatgaagtc | 780 |
| tcggacatgg | gcgtctgtcc | atttgcattc | cttttttgca | gttggaaccc | tgctggtggc | 840 |
| tttgacagga | tacttggtca | ggacctggtg | gctttaccag | atgatcctct | ccacagtgac | 900 |
| tgtccccttt | atcctgtgct | gttgggtgct | cccagagaca | ccttttttggc | ttctctcaga | 960 |
| gggacgatat | gaagaagcac | aaaaaatagt | tgacatcatg | gccaagtgga | acagggcaag | 1020 |
| ctcctgtaaa | ctgtcagaac | ttttatcact | ggacctacaa | ggtcctgtta | gtaatagccc | 1080 |
| cactgaagtt | cagaagcaca | acctatcata | tctgtttttat | aactggagca | ttacgaaaag | 1140 |
| gacacttacc | gtttggctaa | tctggttcac | tggaagtttg | ggattctact | cgttttcctt | 1200 |
| gaattctgtt | aacttaggag | gcaatgaata | cttaaacctc | ttcctcctgg | gtgtagtgga | 1260 |

Fig. 14B

```
aattcccgcc tacaccttcg tgtgcatcgc catggacaag gtcgggagga gaacagtcct  1320
ggcctactct cttttctgca gtgcactggc ctgtggtgtc gttatggtga tcccccagaa  1380
acattatatt ttgggtgtgg tgacagctat ggttggaaaa tttgccatcg gggcagcatt  1440
tggcctcatt tatctttata cagctgagct gtatccaacc attgtaagat cgctggctgt  1500
gggaagcggc agcatggtgt gtcgcctggc cagcatcctg gcgccgttct ctgtggacct  1560
cagcagcatt tggatcttca taccacagtt gtttgttggg actatggccc tcctgagtgg  1620
agtgttaaca ctaaagcttc cagaaaccct tgggaacgg ctagcaacta cttgggagga  1680
ggctgcaaaa ctggagtcag agaatgaaag caagtcaagc aaattacttc tcacaactaa  1740
taatagtggg ctggaaaaaa cggaagcgat taccccagg gattctggtc ttggtgaata  1800
aatgtgccat gcctgctgtc tagcacctga aatattattt accctaatgc ctttgtatta  1860
gaggaatctt attctcatct cccatatgtt gtttgtatgt cttttaata aattttgtaa  1920 gaaaatttta aagcaaatat gttataaaag aaataaaaac taagatgaaa aaaaaaaaa  1980 aaa                                                                 1983
```

(SEQ ID NO 13)

Figure 15A

```
Met Gly Ser Arg His Phe Glu Gly Ile Tyr Asp His Val Gly His Phe
1               5                   10                  15

Gly Arg Phe Gln Arg Val Leu Tyr Phe Ile Cys Ala Phe Gln Asn Ile
            20                  25                  30

Ser Cys Gly Ile His Tyr Leu Ala Ser Val Phe Met Gly Val Thr Pro
            35                  40                  45

His His Val Cys Arg Pro Pro Gly Asn Val Ser Gln Val Val Phe His
            50                  55                  60

Asn His Ser Asn Trp Ser Leu Glu Asp Thr Gly Ala Leu Leu Ser Ser
65                  70                  75                  80

Gly Gln Lys Asp Tyr Val Thr Val Gln Leu Gln Asn Gly Glu Ile Trp
                85                  90                  95

Glu Leu Ser Arg Cys Ser Arg Asn Lys Arg Glu Asn Thr Ser Ser Leu
            100                 105                 110

Gly Tyr Glu Tyr Thr Gly Ser Lys Lys Glu Phe Pro Cys Val Asp Gly
            115                 120                 125

Tyr Ile Tyr Asp Gln Asn Thr Trp Lys Ser Thr Ala Val Thr Gln Trp
            130                 135                 140

Asn Leu Val Cys Asp Arg Lys Trp Leu Ala Met Leu Ile Gln Pro Leu
145                 150                 155                 160

Phe Met Phe Gly Val Leu Leu Gly Ser Val Thr Phe Gly Tyr Phe Ser
                165                 170                 175
```

Fig. 15B

```
Asp Arg Leu Gly Arg Arg Val Val Leu Trp Ala Thr Ser Ser Met
            180             185             190

Phe Leu Phe Gly Ile Ala Ala Ala Phe Ala Val Asp Tyr Tyr Thr Phe
            195             200             205

Met Ala Ala Arg Phe Phe Leu Ala Met Val Ala Ser Gly Tyr Leu Val
210             215             220

Val Gly Phe Val Tyr Val Met Glu Phe Ile Gly Met Lys Ser Arg Thr
225             230             235             240

Trp Ala Ser Val His Leu His Ser Phe Phe Ala Val Gly Thr Leu Leu
            245             250             255

Val Ala Leu Thr Gly Tyr Leu Val Arg Thr Trp Trp Leu Tyr Gln Met
            260             265             270

Ile Leu Ser Thr Val Thr Val Pro Phe Ile Leu Cys Cys Trp Val Leu
            275             280             285

Pro Glu Thr Pro Phe Trp Leu Leu Ser Glu Gly Arg Tyr Glu Glu Ala
            290             295             300

Gln Lys Ile Val Asp Ile Met Ala Lys Trp Asn Arg Ala Ser Ser Cys
305             310             315             320

Lys Leu Ser Glu Leu Leu Ser Leu Asp Leu Gln Gly Pro Val Ser Asn
            325             330             335

Ser Pro Thr Glu Val Gln Lys His Asn Leu Ser Tyr Leu Phe Tyr Asn
            340             345             350
```

Fig. 15C

| | | | | | | | | | | | | |
|---|---|---|---|---|---|---|---|---|---|---|---|---|
|Trp|Ser|Ile|Thr|Lys|Arg|Thr|Leu|Thr|Val|Trp|Leu|Ile|Trp|Phe|Thr|
| |355| | | |360| | | | |365| | |

Ser Ile Thr Lys Arg Thr Leu Thr Val Trp Leu Ile Trp Phe Thr — writing as plain lines:

Trp Ser Ile Thr Lys Arg Thr Leu Thr Val Trp Leu Ile Trp Phe Thr
        355            360              365

Gly Ser Leu Gly Phe Tyr Ser Phe Ser Leu Asn Ser Val Asn Leu Gly
        370            375              380

Gly Asn Glu Tyr Leu Asn Leu Phe Leu Leu Gly Val Val Glu Ile Pro
385                 390              395              400

Ala Tyr Thr Phe Val Cys Ile Ala Met Asp Lys Val Gly Arg Arg Thr
                405              410              415

Val Leu Ala Tyr Ser Leu Phe Cys Ser Ala Leu Ala Cys Gly Val Val
                420              425              430

Met Val Ile Pro Gln Lys His Tyr Ile Leu Gly Val Val Thr Ala Met
                435              440              445

Val Gly Lys Phe Ala Ile Gly Ala Ala Phe Gly Leu Ile Tyr Leu Tyr
                450              455              460

Thr Ala Glu Leu Tyr Pro Thr Ile Val Arg Ser Leu Ala Val Gly Ser
465              470              475              480

Gly Ser Met Val Cys Arg Leu Ala Ser Ile Leu Ala Pro Phe Ser Val
                485              490              495

Asp Leu Ser Ser Ile Trp Ile Phe Ile Pro Gln Leu Phe Val Gly Thr
                500              505              510

Met Ala Leu Leu Ser Gly Val Leu Thr Leu Lys Leu Pro Glu Thr Leu
                515              520              525

Fig. 15D

```
Gly Lys Arg Leu Ala Thr Thr Trp Glu Glu Ala Ala Lys Leu Glu Ser
    530             535             540

Glu Asn Glu Ser Lys Ser Ser Lys Leu Leu Leu Thr Thr Asn Asn Ser
545             550             555             560

Gly Leu Glu Lys Thr Glu Ala Ile Thr Pro Arg Asp Ser Gly Leu Gly
            565             570             575

Glu (SEQ ID NO 14)
```

Figure 16A

| | | | | | |
|---|---|---|---|---|---|
| agcttctgcc | ctgcctgctg | tgtgcggagc | cgtccagcga | ccaccatggt | gaggctcgtg | 60 |
| ctgcccaacc | ccggcctaga | cgcccggatc | ccgtccctgg | ctgagctgga | gaccatcgag | 120 |
| caggaggagg | ccagctcccg | gccgaagtgg | gacaacaagg | cgcagtacat | gctcacctgc | 180 |
| ctgggcttct | gcgtgggcct | cggcaacgtg | tggcgcttcc | cctacctgtg | tcagagccac | 240 |
| ggaggaggag | ccttcatgat | cccgttcctc | atcctgctgg | tcctggaggg | catcccctg | 300 |
| ctgtacctgg | agttcgccat | cgggcagcgg | ctgcggcggg | gcagcctggg | tgtgtggagc | 360 |
| tccatccacc | cggccctgaa | gggcctaggc | ctggcctcca | tgctcacgtc | cttcatggtg | 420 |
| ggactgtatt | acaacaccat | catctcctgg | atcatgtggt | acttattcaa | ctccttccag | 480 |
| gagcctctgc | cctggagcga | ctgcccgctc | aacgagaacc | agacagggta | tgtggacgag | 540 |
| tgcgccagga | gctcccctgt | ggactacttc | tggtaccgag | agacgctcaa | catctccacg | 600 |
| tccatcagcg | actcgggctc | catccagtgg | tggatgctgc | tgtgcctggc | ctgcgcatgg | 660 |
| agcgtcctgt | acatgtgcac | catccgcggc | atcgagacca | ccgggaaggc | cgtgtacatc | 720 |
| acctccacgc | tgcctatgt | cgtcctgacc | atcttcctca | tccgaggcct | gacgctgaag | 780 |
| ggcgccacca | atggcatcgt | cttcctcttc | acgcccaacg | tcacggagct | ggcccagccg | 840 |
| gacacctggc | tggacgcggg | cgcacaggtc | ttcttctcct | tctccctggc | cttcggggc | 900 |

Fig. 16B

```
ctcatctcct tctccagcta caactctgtg cacaacaact gcgagaagga ctcggtgatt      960
gtgtccatca tcaacggctt cacatcggtg tatgtggcca tcgtggtcta ctccgtcatt     1020
gggttccgcg ccacgcagcg ctacgacgac tgcttcagca cgaacatcct gaccctcatc     1080
aacgggttcg acctgcctga aggcaacgtg acccaggaga actttgtgga catgcagcag     1140
cggtgcaacg cctccgaccc cgcggcctac gcgcagctgg tgttccagac ctgcgacatc     1200
aacgccttcc tctcagaggc cgtggagggc acaggcctgg ccttcatcgt cttcaccgag     1260
gccatcacca agatgccgtt gtccccactg tggtctgtgc tcttcttcat tatgctcttc     1320
tgcctggggc tgtcatctat gtttgggaac atggagggcg tcgttgtgcc cctgcaggac     1380
ctcagagtca tccccccgaa gtggcccaag gaggtgctca caggcctcat ctgcctgggg     1440
acattcctca ttggcttcat cttcacgctg aactccggcc agtactggct ctccctgctg     1500
gacagctatg ccggctccat tcccctgctc atcatcgcct ctgcgagat gttctctgtg     1560 gtctacgtgt acggtgtgga caggttcaat aaggacatcg agttcatgat cggccacaag     1620
cccaacatct tctggcaagt cacgtggcgc gtggtcagcc ccctgctcat gctgatcatc     1680
ttcctcttct tcttcgtggt agaggtcagt caggagctga cctacagcat ctgggaccct     1740
```

Fig. 16C

```
ggctacgagg aatttcccaa atcccagaag atctcctacc cgaactgggt gtatgtggtg      1800
gtggtgattg tggctggagt gccctccctc accatccctg gctatgccat ctacaagctc      1860
atcaggaacc actgccagaa gccaggggac catcaggggc tggtgagcac actgtccaca      1920
gcctccatga acggggacct gaagtactga gaaggcccat cccacggcgt gccatacact      1980
ggtgtcaggg aaggaggaac cagcaagacc tgtggggtgg gggccgggct gcacctgcat      2040
gtgtgtaagc gtgagtgtat gctcgtgtgt gagtgtgtgt attgtacacg catgtgccat      2100
gtgtgcagat atgtatcgtg tgtgcatgta catgcatggg cactgtgagt gtgcacgtgt      2160
atgcacacat atacatgtgt gtgggtgtgt gtattgtatg tgcatgtgcc atgtgtgcag      2220
atgtgtcatg ttgtgtgtgt gcatgtacat gtatggacat tgtgtgagtg tgcaagtgtg      2280
catgcatata catgtgtgcg atatttgctg cccgtgtgtg tgcatgtata tatagacata      2340
catgcctatg ttgtgtgtgg tgtgcatatg tgtgaacaca cacgtgtata catgcatgca      2400
catgtgctcg tacaatgggt gtccacatgc acgtgtatat gtatatctgt gagtgtatat      2460
acatgcatgc aattgtgtgt atgtgtgttc tgtgtgtgcg tttgcaagta tatatgcaca      2520
tgtgtatatg tacatgtatg cctgtgtgac gtgtgtatat gtgagcatgt gtacgtgtgt      2580
gtatacgtgt gttgtgtata tgtgtgtgtc tgtacctgtt tgtgtatatg tgtgtgatgt      2640
```

Fig. 16D

| | | | | | |
|---|---|---|---|---|---|
| gtgctcgtgt | gtgtgcatat | tcaggcaggt | gtgcatttgt | gcatcccagt | gtgtatgtat | 2700 |
| gtgcgcatat | ggacacgcat | ggacacgcat | atggacacat | atggacacac | atatggacac | 2760 |
| gtgtggatat | gtgtgcgtac | acgtcgctgg | gacacatgcc | tgccactcgg | ggcccagctg | 2820 |
| accctctgtg | tttgtccttg | ccacagtcac | ggggtgcatg | tgcagagggg | agcagaccac | 2880 |
| tggggacgtg | ctgtgccctg | cacgtgcccg | ggggaagcgg | aagctgcagc | tggggtgggg | 2940 |
| gcagcacctc | tatgcttcat | ctctgtgggt | ggcaggagac | aaaagcacag | ggtactatct | 3000 |
| tggctcctgg | gagcgactct | tgctacccac | ccccacccat | cccttcccc | ttggtgttga | 3060 |
| cctttgacct | ggggttccc | agagccctgt | agccctcgac | ccggagcagc | ctctcggaag | 3120 |
| ccggagtggg | cagttgctgg | cgattctgag | aaaacttggc | cgcatccacc | ggggccctgc | 3180 |
| ctccagtcgg | ccgctgccga | gtctctgcgt | tctggccgct | tcccggctta | atgaatgcca | 3240 |
| gccatttaat | cattgctcct | gccaccacaa | atagatgagc | agttaaataa | aactcaactt | 3300 |
| ggcataattc | aaggcaaata | ccactctgtg | cattttctta | agaggacatg | agctgtgtga | 3360 |
| attttagcc | agcctttgga | aaagatgggt | tacagggtaa | ctcaaccctg | gctgccatcc | 3420 |
| ttgggcactg | tgtgtgtcca | gggcaccttg | gaggaccgtg | cagcccccag | aagcttccag | 3480 |
| ctcccgcacc | actcagtgaa | gcccagcctg | gcgcctgccc | tgcccccgtc | acgggatggg | 3540 |

Fig. 16E

```
cccccattgg ggttcaacat tccatcgcag ccaaaggcag tcggcacttg ggacatctgc    3600
ttccacggac aggtcacctc cgctttgcac ggaagaatct ggatgcttac attaaactga    3660
tgttctgaga gttcctacgg acaggtcacc tccgctttgc atggaagaat ctggatgctt    3720
acattaaact ggtgttctga gagttcctac ggacaggtca cctccgcttt ccatagaaga    3780
atctggacgc ttacattaaa ctgatgttct gagaattcct acaggcagga ctgaaagcct    3840
ggtgtgtgcc agtatgatgt tccacccacg gaaacctggt cacaatcgtc ccttccagca    3900
ccccatccag cagtgactgc acacactgag cccctacca gccctttca cctgctgac      3960 tgtcactggg ccctgggatg tgcaagactc cacagcagca gaggtgggggg gacatatcac    4020 agcctctgcc cccggctgtg atgccaccga ggggctcgcc tgctgatggc ttcaacaggg    4080
tctcacctca tctttcctg ctctttggcc ctggatcgag aaaatttcca tcagtgcccc    4140
attaatatgc tgccctgtgg catctgccca ggaggccctg ccaggcgtgc acaggtgtgc    4200
attggtgtac cctggcatgc acaggtgtgc actgatgtgc cctggcatcc attggtgtac    4260
cctggtgtgc ctgccatagg accctgggcg ggagctccca tctcatctac atctcctgat    4320
tcatgcgttg tttcataggt ttcaatgtct ctgtaaatgt ggtagaaatg caggctttat    4380
gggcataaag tgtacatttc taaataaatc ccttctattt agtatgctca ccctagaagt    4440
```

Fig. 16F

```
tactgttgtc cagacgtaga gggatgagtg agccagtgac ctcagacggg atggtgggga      4500
cggcaggtcc agctcctgcc tcctcctggg gggtctggct ttgggggctt gctccgaaga      4560
ggccatggcc caggcctgtg gcctcacaat ggggaccaac cagctcttct catcttcttc      4620
cctcacactt cctctcactc aaataagaac cttccaaaaa tgtgtccacc tgggcccctg      4680
ccctgggact catggatttg gagttgtggc cacacggttg aggggtgcag tgtccagtgg      4740
aatggggcaa ttgcgggcct gggggcccct ggcctgtccg tggcgggagc atctgcaagg      4800
aggagcccca gagtccaggg agcactgtgg ggagctcctt agagctgaac tcacccggcg      4860
tcaactcatc aaccctccac ccatggacag gggtgccccc agcacaggag aggactcagc      4920
cctctgcccc cacgcacggt gggtgcctgt caccctgtcc tgcccagcgg cccgagggca      4980
gcagtgggtg tgagggcagc ccccggcctc ccaagagcag ctgagaggat ccctgcggga      5040
atccgggctt cgggtgcatg cgatctgatc tgagttgttt ctgacagtga cagagtgaca      5100
atctataagt atctcaagat caaatggtta aataaaacat aagaaattta aacgattaa       5160 aaaaaaaaaa aaaaa                                                       5175
```

(SEQ ID NO 15)

SEQUENCE LISTING

<160> NUMBER OF SEQ ID NOS: 15

<210> SEQ ID NO 1
<211> LENGTH: 634
<212> TYPE: PRT
<213> ORGANISM: Homo sapiens

<400> SEQUENCE: 1

```
Met Val Arg Leu Val Leu Pro Asn Pro Gly Leu Asp Ala Arg Ile Pro
 1               5                  10                  15

Ser Leu Ala Glu Leu Glu Thr Ile Glu Gln Glu Ala Ser Ser Arg
            20                  25                  30

Pro Lys Trp Asp Asn Lys Ala Gln Tyr Met Leu Thr Cys Leu Gly Phe
            35                  40                  45

Cys Val Gly Leu Gly Asn Val Trp Arg Phe Pro Tyr Leu Cys Gln Ser
        50                  55                  60

His Gly Gly Gly Ala Phe Met Ile Pro Phe Leu Ile Leu Leu Val Leu
65                  70                  75                  80

Glu Gly Ile Pro Leu Leu Tyr Leu Glu Phe Ala Ile Gly Gln Arg Leu
                85                  90                  95

Arg Arg Gly Ser Leu Gly Val Trp Ser Ser Ile His Pro Ala Leu Lys
            100                 105                 110

Gly Leu Gly Leu Ala Ser Met Leu Thr Ser Phe Met Val Gly Leu Tyr
        115                 120                 125

Tyr Asn Thr Ile Ile Ser Trp Ile Met Trp Tyr Leu Phe Asn Ser Phe
    130                 135                 140

Gln Glu Pro Leu Pro Trp Ser Asp Cys Pro Leu Asn Glu Asn Gln Thr
145                 150                 155                 160

Gly Tyr Val Asp Glu Cys Ala Arg Ser Ser Pro Val Asp Tyr Phe Trp
                165                 170                 175

Tyr Arg Glu Thr Leu Asn Ile Ser Thr Ser Ile Ser Asp Ser Gly Ser
            180                 185                 190

Ile Gln Trp Trp Met Leu Leu Cys Leu Ala Cys Ala Trp Ser Val Leu
        195                 200                 205

Tyr Met Cys Thr Ile Arg Gly Ile Glu Thr Thr Gly Lys Ala Val Tyr
    210                 215                 220

Ile Thr Ser Thr Leu Pro Tyr Val Val Leu Thr Ile Phe Leu Ile Arg
225                 230                 235                 240

Gly Leu Thr Leu Lys Gly Ala Thr Asn Gly Ile Val Phe Leu Phe Thr
                245                 250                 255

Pro Asn Val Thr Glu Leu Ala Gln Pro Asp Thr Trp Leu Asp Ala Gly
            260                 265                 270

Ala Gln Val Phe Phe Ser Phe Ser Leu Ala Phe Gly Gly Leu Ile Ser
        275                 280                 285

Phe Ser Ser Tyr Asn Ser Val His Asn Asn Cys Glu Lys Asp Ser Val
    290                 295                 300

Ile Val Ser Ile Ile Asn Gly Phe Thr Ser Val Tyr Val Ala Ile Val
305                 310                 315                 320

Val Tyr Ser Val Ile Gly Phe Arg Ala Thr Gln Arg Tyr Asp Asp Cys
                325                 330                 335

Phe Ser Thr Asn Ile Leu Thr Leu Ile Asn Gly Phe Asp Leu Pro Glu
            340                 345                 350

Gly Asn Val Thr Gln Glu Asn Phe Val Asp Met Gln Gln Arg Cys Asn
```

```
                 355                 360                 365

Ala Ser Asp Pro Ala Ala Tyr Ala Gln Leu Val Phe Gln Thr Cys Asp
            370                 375                 380

Ile Asn Ala Phe Leu Ser Glu Ala Val Glu Gly Thr Gly Leu Ala Phe
385                 390                 395                 400

Ile Val Phe Thr Glu Ala Ile Thr Lys Met Pro Leu Ser Pro Leu Trp
                405                 410                 415

Ser Val Leu Phe Phe Ile Met Leu Phe Cys Leu Gly Leu Ser Ser Met
                420                 425                 430

Phe Gly Asn Met Glu Gly Val Val Pro Leu Gln Asp Leu Arg Val
            435                 440                 445

Ile Pro Pro Lys Trp Pro Lys Glu Val Leu Thr Gly Leu Ile Cys Leu
450                 455                 460

Gly Thr Phe Leu Ile Gly Phe Ile Phe Thr Leu Asn Ser Gly Gln Tyr
465                 470                 475                 480

Trp Leu Ser Leu Leu Asp Ser Tyr Ala Gly Ser Ile Pro Leu Leu Ile
                485                 490                 495

Ile Ala Phe Cys Glu Met Phe Ser Val Val Tyr Val Tyr Gly Val Asp
            500                 505                 510

Arg Phe Asn Lys Asp Ile Glu Phe Met Ile Gly His Lys Pro Asn Ile
            515                 520                 525

Phe Trp Gln Val Thr Trp Arg Val Ser Pro Leu Leu Met Leu Ile
530                 535                 540

Ile Phe Leu Phe Phe Val Val Glu Val Ser Gln Glu Leu Thr Tyr
545                 550                 555                 560

Ser Ile Trp Asp Pro Gly Tyr Glu Glu Phe Pro Lys Ser Gln Lys Ile
                565                 570                 575

Ser Tyr Pro Asn Trp Val Tyr Val Val Val Ile Val Ala Gly Val
            580                 585                 590

Pro Ser Leu Thr Ile Pro Gly Tyr Ala Ile Tyr Lys Leu Ile Arg Asn
                595                 600                 605

His Cys Gln Lys Pro Gly Asp His Gln Gly Leu Val Ser Thr Leu Ser
            610                 615                 620

Thr Ala Ser Met Asn Gly Asp Leu Lys Tyr
625                 630

<210> SEQ ID NO 2
<211> LENGTH: 634
<212> TYPE: PRT
<213> ORGANISM: Mus musculus

<400> SEQUENCE: 2

Met Val Arg Leu Val Leu Pro Asn Pro Gly Leu Glu Glu Arg Ile Pro
1               5                   10                  15

Ser Leu Asp Glu Leu Glu Val Ile Glu Lys Glu Glu Ala Gly Ser Arg
            20                  25                  30

Pro Lys Trp Asp Asn Lys Ala Gln Tyr Met Leu Thr Cys Val Gly Phe
        35                  40                  45

Cys Val Gly Leu Gly Asn Val Trp Arg Phe Pro Tyr Leu Cys Gln Ser
    50                  55                  60

His Gly Gly Gly Ala Phe Met Ile Pro Phe Leu Ile Leu Leu Val Phe
65                  70                  75                  80

Glu Gly Ile Pro Leu Leu Tyr Leu Glu Phe Ala Ile Gly Gln Arg Leu
                85                  90                  95
```

```
Arg Lys Gly Ser Met Gly Val Trp Ser Ser Ile His Pro Ala Leu Lys
            100                 105                 110

Gly Ile Gly Ile Ala Ser Met Phe Val Ser Phe Met Val Gly Leu Tyr
        115                 120                 125

Tyr Asn Thr Ile Ile Ala Trp Val Met Trp Tyr Phe Phe Asn Ser Phe
    130                 135                 140

Gln Glu Pro Leu Pro Trp Ser Glu Cys Pro Leu Asn Gln Asn Gln Thr
145                 150                 155                 160

Gly Tyr Val Glu Glu Cys Ala Lys Ser Ser Val Asp Tyr Phe Trp
                165                 170                 175

Tyr Arg Glu Thr Leu Asn Ile Ser Thr Ser Ile Ser Asp Ser Gly Ser
            180                 185                 190

Ile Gln Trp Trp Ile Leu Leu Cys Leu Thr Cys Ala Trp Ser Val Leu
        195                 200                 205

Tyr Val Cys Ile Ile Arg Gly Ile Glu Thr Thr Gly Lys Ala Val Tyr
    210                 215                 220

Ile Thr Ser Thr Leu Pro Tyr Val Val Leu Thr Ile Phe Leu Ile Arg
225                 230                 235                 240

Gly Leu Thr Leu Lys Gly Ala Thr Asn Gly Ile Val Phe Leu Phe Thr
                245                 250                 255

Pro Asn Ile Thr Glu Leu Ser Asn Pro Asn Thr Trp Leu Asp Ala Gly
            260                 265                 270

Ala Gln Val Phe Tyr Ser Phe Ser Leu Ala Phe Gly Gly Leu Ile Ser
        275                 280                 285

Phe Ser Ser Tyr Asn Ser Val His Asn Asn Cys Glu Met Asp Ser Val
    290                 295                 300

Ile Val Ser Val Ile Asn Gly Phe Thr Ser Val Tyr Ala Ala Thr Val
305                 310                 315                 320

Val Tyr Ser Ile Ile Gly Phe Arg Ala Thr Glu Arg Phe Asp Asp Cys
                325                 330                 335

Val Asn Thr Asn Ile Leu Thr Leu Ile Asn Gly Phe Asp Leu Pro Glu
            340                 345                 350

Gly Asn Val Thr Ser Glu Asn Phe Glu Ala Tyr Gln Gln Trp Cys Asn
        355                 360                 365

Ala Thr Asn Pro Gln Ala Tyr Ala Gln Leu Lys Phe Gln Thr Cys Asp
    370                 375                 380

Ile Asn Ser Phe Leu Ser Glu Gly Val Glu Gly Thr Gly Leu Ala Phe
385                 390                 395                 400

Ile Val Phe Thr Glu Ala Ile Thr Lys Met Pro Val Ser Pro Leu Trp
                405                 410                 415

Ser Val Leu Phe Phe Ile Met Leu Phe Cys Leu Gly Leu Ser Ser Met
            420                 425                 430

Phe Gly Asn Met Glu Gly Val Val Pro Leu Gln Asp Leu Asn Ile
        435                 440                 445

Thr Pro Lys Lys Trp Pro Lys Glu Leu Leu Thr Gly Leu Ile Cys Leu
    450                 455                 460

Gly Thr Tyr Leu Ile Ala Phe Ile Phe Thr Leu Asn Ser Gly Gln Tyr
465                 470                 475                 480

Trp Leu Ser Leu Leu Asp Ser Phe Ala Gly Ser Ile Pro Leu Leu Ile
                485                 490                 495

Ile Ala Phe Cys Glu Met Phe Ala Val Val Tyr Val Tyr Gly Val Asp
            500                 505                 510

Arg Phe Asn Lys Asp Ile Glu Phe Met Ile Gly His Lys Pro Asn Ile
```

```
                515                 520                 525
Phe Trp Gln Val Thr Trp Arg Val Val Ser Pro Leu Ile Met Leu Val
    530                 535                 540

Ile Phe Leu Phe Phe Phe Val Ile Glu Val Asn Lys Thr Leu Met Tyr
545                 550                 555                 560

Ser Ile Trp Asp Pro Asn Tyr Glu Glu Phe Pro Lys Ser Gln Lys Ile
                565                 570                 575

Pro Tyr Pro Asn Trp Val Tyr Ala Val Val Thr Val Ala Gly Val
                580                 585                 590

Pro Cys Leu Ser Ile Pro Cys Phe Ala Ile Tyr Lys Phe Ile Arg Asn
        595                 600                 605

Cys Cys Gln Lys Ser Asp Asp His His Gly Leu Val Asn Thr Leu Ser
    610                 615                 620

Thr Ala Ser Val Asn Gly Asp Leu Lys Asn
625                 630

<210> SEQ ID NO 3
<211> LENGTH: 634
<212> TYPE: PRT
<213> ORGANISM: Rattus norvegicus

<400> SEQUENCE: 3

Met Val Arg Leu Val Leu Pro Asn Pro Gly Leu Glu Asp Arg Ile Pro
1               5                   10                  15

Ser Leu Asp Glu Leu Glu Val Ile Glu Lys Glu Glu Ala Ser Ser Lys
                20                  25                  30

Pro Lys Trp Asp Asn Lys Ala Gln Tyr Met Leu Thr Cys Val Gly Phe
            35                  40                  45

Cys Val Gly Leu Gly Asn Val Trp Arg Phe Pro Tyr Leu Cys Gln Ser
        50                  55                  60

His Gly Gly Gly Ala Phe Met Ile Pro Phe Leu Ile Leu Leu Val Leu
65                  70                  75                  80

Glu Gly Ile Pro Leu Leu His Leu Glu Phe Ala Ile Gly Gln Arg Leu
                85                  90                  95

Arg Lys Gly Ser Val Gly Val Trp Ser Ser Ile His Pro Ala Leu Lys
            100                 105                 110

Gly Val Gly Ile Ala Ser Met Phe Val Ser Phe Met Val Gly Leu Tyr
        115                 120                 125

Tyr Asn Thr Ile Ile Ala Trp Val Met Trp Tyr Phe Phe Asn Ser Phe
130                 135                 140

Gln Glu Pro Leu Pro Trp Ser Glu Cys Pro Leu Asn Gln Asn Gln Thr
145                 150                 155                 160

Gly Tyr Val Glu Glu Cys Ala Lys Ser Ser Val Asp Tyr Phe Trp
            165                 170                 175

Tyr Arg Glu Thr Leu Asn Ile Ser Thr Pro Ile Ser Asp Ser Gly Ser
            180                 185                 190

Ile Gln Trp Trp Ile Leu Leu Cys Leu Thr Cys Ala Trp Ser Val Leu
        195                 200                 205

Tyr Val Cys Thr Ile Arg Gly Ile Glu Thr Thr Gly Lys Ala Val Tyr
    210                 215                 220

Ile Thr Ser Thr Leu Pro Tyr Val Val Leu Thr Ile Phe Leu Ile Arg
225                 230                 235                 240

Gly Leu Thr Leu Lys Gly Ala Thr Asn Gly Ile Val Phe Leu Phe Thr
                245                 250                 255
```

```
Pro Asn Ile Thr Glu Leu Ser Asn Pro Asn Thr Trp Leu Asp Ala Gly
            260                 265                 270

Ala Gln Val Tyr Tyr Ser Phe Ser Leu Ala Phe Gly Gly Leu Ile Ser
        275                 280                 285

Phe Ser Ser Tyr Asn Ser Val His Asn Asn Cys Glu Met Asp Ser Val
    290                 295                 300

Ile Val Ser Ile Ile Asn Gly Phe Thr Ser Val Tyr Ala Ala Thr Val
305                 310                 315                 320

Val Tyr Ser Ile Ile Gly Phe Arg Ala Thr Glu Arg Phe Asp Asp Cys
                325                 330                 335

Val Asn Thr Asn Ile Leu Thr Leu Ile Asn Gly Phe Asp Leu Pro Glu
            340                 345                 350

Gly Asn Val Thr Ala Glu Asn Phe Glu Ala Tyr Gln His Trp Cys Asn
        355                 360                 365

Ala Thr Asn Pro Glu Ala Tyr Ala Gln Leu Thr Phe Gln Thr Cys Asp
    370                 375                 380

Ile Asn Thr Phe Leu Ser Glu Gly Val Glu Gly Thr Gly Leu Ala Phe
385                 390                 395                 400

Ile Val Phe Thr Glu Ala Ile Thr Lys Met Pro Val Ser Pro Leu Trp
                405                 410                 415

Ser Val Leu Phe Phe Ile Met Leu Phe Cys Leu Gly Leu Ser Ser Met
            420                 425                 430

Phe Gly Asn Met Glu Gly Val Val Pro Leu Gln Asp Leu Asn Ile
        435                 440                 445

Thr Pro Lys Lys Trp Pro Lys Glu Leu Leu Thr Gly Leu Ile Cys Leu
    450                 455                 460

Gly Thr Tyr Leu Ile Ala Phe Ile Phe Thr Leu Asn Ser Gly Gln Tyr
465                 470                 475                 480

Trp Leu Ser Leu Leu Asp Ser Tyr Ala Gly Ser Ile Pro Leu Leu Ile
                485                 490                 495

Ile Ala Phe Cys Glu Met Phe Ala Val Val Tyr Val Tyr Gly Val Asp
            500                 505                 510

Arg Phe Asn Lys Asp Ile Glu Phe Met Ile Gly His Lys Pro Asn Ile
        515                 520                 525

Phe Trp Gln Val Thr Trp Arg Val Val Ser Pro Leu Ile Met Leu Val
    530                 535                 540

Ile Phe Leu Phe Phe Phe Val Ile Glu Val Asn Lys Gln Leu Met Tyr
545                 550                 555                 560

Ser Val Trp Asp Pro Asp Tyr Glu Glu Phe Pro Lys Ser Gln Lys Val
                565                 570                 575

Pro Tyr Pro Asp Trp Val Tyr Ala Val Val Ile Val Ala Gly Val
            580                 585                 590

Pro Cys Leu Thr Ile Pro Cys Phe Ala Ile Tyr Lys Leu Ile Arg Asn
        595                 600                 605

Tyr Cys Gln Lys Ser Gly Asp Gln His Gly Leu Val Asn Ala Leu Ser
    610                 615                 620

Thr Ala Ser Val Asn Gly Asp Leu Lys Asn
625                 630

<210> SEQ ID NO 4
<211> LENGTH: 1905
<212> TYPE: DNA
<213> ORGANISM: Homo sapiens

<400> SEQUENCE: 4
```

```
atggtgaggc tcgtgctgcc caaccccggc ctagacgccc ggatcccgtc cctggctgag    60
ctggagacca tcgagcagga ggaggccagc tcccggccga agtgggacaa caaggcgcag   120
tacatgctca cctgcctggg cttctgcgtg ggcctcggca acgtgtggcg cttcccctac   180
ctgtgtcaga gccacggagg aggagccttc atgatcccgt tcctcatcct gctggtcctg   240
gagggcatcc ccctgctgta cctggagttc gccatcgggc agcggctgcg gcggggcagc   300
ctgggtgtgt ggagctccat ccacccggcc ctgaagggcc taggcctggc ctccatgctc   360
acgtccttca tggtgggact gtattacaac accatcatct cctggatcat gtggtactta   420
ttcaactcct tccaggagcc tctgccctgg agcgactgcc cgctcaacga gaaccagaca   480
gggtatgtgg acgagtgcgc caggagctcc cctgtggact acttctggta ccgagagacg   540
ctcaacatct ccacgtccat cagcgactcg ggctccatcc agtggtggat gctgctgtgc   600
ctggcctgcg catggagcgt cctgtacatg tgcaccatcc gcggcatcga gaccaccggg   660
aaggccgtgt acatcacctc cacgctgccc tatgtcgtcc tgaccatctt cctcatccga   720
ggcctgacgc tgaagggcgc caccaatggc atcgtcttcc tcttcacgcc caacgtcacg   780
gagctggccc agccggacac ctggctggac gcgggcgcac aggtcttctt ctccttctcc   840
ctggccttcg ggggcctcat ctccttctcc agctacaact ctgtgcacaa caactgcgag   900
aaggactcgg tgattgtgtc catcatcaac ggcttcacat cggtgtatgt ggccatcgtg   960
gtctactccg tcattgggtt ccgcgccacg cagcgctacg acgactgctt cagcacgaac  1020
atcctgaccc tcatcaacgg gttcgacctg cctgaaggca acgtgaccca ggagaacttt  1080
gtggacatgc agcagcggtg caacgcctcc gaccccgcgg cctacgcgca gctggtgttc  1140
cagacctgcg acatcaacgc cttcctctca gaggccgtgg agggcacagg cctggccttc  1200
atcgtcttca ccgaggccat caccaagatg ccgttgtccc cactgtggtc tgtgctcttc  1260
ttcattatgc tcttctgcct ggggctgtca tctatgtttg gaacatgga gggcgtcgtt  1320 gtgcccctgc aggacctcag agtcatcccc cgaagtggcc caaggaggt gctcacaggc  1380 ctcatctgcc tggggacatt cctcattggc ttcatcttca cgctgaactc cggccagtac  1440
tggctctccc tgctggacag ctatgccggc tccattcccc tgctcatcat cgccttctgc  1500
gagatgttct ctgtggtcta cgtgtacggg gtggacaggt tcaataagga catcgagttc  1560
atgatcggcc acaagcccaa catcttctgg caagtcacgt ggcgcgtggt cagcccctg  1620 ctcatgctga tcatcttcct cttcttcttc gtggtagagg tcagtcagga gctgacctac  1680
agcatctggg accctggcta cgaggaatt cccaaatccc agaagatctc ctacccgaac  1740
tgggtgtatg tggtggtggt gattgtggct ggagtgccct ccctcaccat ccctggctat  1800
gccatctaca gctcatcag gaaccactgc cagaagccag gggaccatca ggggctggtg  1860
agcacactgt ccacagcctc catgaacggg gacctgaagt actga                 1905
```

<210> SEQ ID NO 5
<211> LENGTH: 1905
<212> TYPE: DNA
<213> ORGANISM: Mus musculus

<400> SEQUENCE: 5

```
atggtgaggc ttgtgctgcc caaccctggc ctagaggagc ggattccatc tctggatgag    60
ttagaggtca ttgaaaagga agaggccggc tccaggccca atgggacaa caaggcccag   120 tacatgctca cctgtgtggg cttttgtgtg gggctgggca acgtgtggcg cttcccctac  180
```

```
ctatgccaga gccatggagg aggggccttc atgatcccat tcctcatcct tctggtgttc    240
gagggaattc ctttgctgta cctggagttt gccatcggtc agaggctacg caagggcagc    300
atgggtgtgt ggagctccat ccaccctgct ctgaagggta taggcatcgc ctccatgttc    360
gtgtccttca tggtgggcct gtactacaac accatcatcg cctgggtcat gtggtacttc    420
ttcaactcct ttcaggaacc tctgccatgg agtgaatgtc cactcaacca gaaccagaca    480
ggctatgtgg aagagtgtgc caagagctct tccgtgact acttctggta ccagagact    540 cttaatatct ccacttccat cagtgactca ggctccatcc agtggtggat cctgctctgc    600
ctgacatgtg cctggagtgt gctgtatgtg tgtattatcc gtggcatcga ccactgggg    660 aaggctgtgt acatcacctc caccctgccc tatgttgtac tgaccatctt tctcatccgt    720
ggcttgactc tgaagggtgc caccaacggc attgtcttcc ttttcacacc caatatcaca    780
gagctgagca accccaacac gtggctggat gcaggtgctc aggtcttcta ctccttctca    840
ctggccttcg gggcctcat ctccttctcc agctacaact ctgtgcacaa taattgtgag    900
atggattctg tgatcgtgtc tgtcatcaat ggcttcacat ctgtgtatgc ggccaccgtg    960
gtctactcca tcattggctt ccgagccact gagcgctttg atgactgtgt caacacgaac    1020
atcctgaccc tcatcaatgg gttcgacctg ccggagggca atgtgacttc agagaacttt    1080
gaggcctacc aacagtggtg caatgccact aatccccagg cctatgcaca actgaagttt    1140
cagacctgtg acattaacag cttcctttct gagggtgtgg agggcacagg cctggccttc    1200
attgtcttca cggaagccat cacgaagatg ccagtgtccc cactgtggtc ggtgctcttt    1260
tttataatgc tcttctgcct gggactctcc tccatgtttg gaacatgga gggtgtggtc    1320 gtaccccttc aggacctcaa tatcaccct aagaagtggc ccaaagaatt gttgacaggc    1380
ctcatctgct tggggacata tctcatcgcc ttcattttca cactgaattc gggccagtac    1440
tggctctctc tcctggacag cttttgctggc tccattcctc tgctaatcat cgccttttgt    1500
gagatgtttg ccgtcgtcta cgtgtatgga gttgacaggt tcaacaagga catcgagttc    1560
atgatcggcc ataagcccaa catcttctgg caagtcacgt ggagagtggt cagtccactg    1620
atcatgctgg tcatcttcct cttcttttt gtgattgagg tcaacaaaac gctcatgtat    1680
agcatctggg accctaacta tgaggagttc ccgaaatctc agaagattcc ataccccaac    1740
tgggtgtatg cagttgtggt cactgtggct ggagtaccct gcctctccat cccctgcttt    1800
gccatctaca gttcatcag aaattgttgt cagaagtctg atgaccacca tgggctggtc    1860
aatacactgt ccacagcctc tgtgaatggg gaccttaaga actga    1905
```

<210> SEQ ID NO 6
<211> LENGTH: 18
<212> TYPE: DNA
<213> ORGANISM: Homo sapiens

<400> SEQUENCE: 6
accatggtga ggctcgtg    18

<210> SEQ ID NO 7
<211> LENGTH: 22
<212> TYPE: DNA
<213> ORGANISM: Homo sapiens

<400> SEQUENCE: 7
gtgtcaggga aggaggaacc ag    22

<210> SEQ ID NO 8
<211> LENGTH: 1905
<212> TYPE: DNA
<213> ORGANISM: Rattus norvegicus

<400> SEQUENCE: 8

| | | | | | |
|---|---|---|---|---|---|
| atggtgaggc | ttgtgctacc | caaccctggc | ctagaggacc | ggattccgtc | tctggatgaa | 60 |
| ttagaggtca | ttgaaaagga | agaggccagc | tccaagccca | aatgggacaa | caaggcccag | 120 |
| tacatgctca | cctgtgtggg | cttctgtgtg | gggctgggca | atgtctggcg | cttcccttac | 180 |
| ctgtgccaga | gccatggagg | aggggccttc | atgatcccct | tcctcatcct | tctggtcctg | 240 |
| gagggcattc | ccttgctgca | cctggagttt | gccatcggac | agaggctacg | caagggcagt | 300 |
| gtgggcgtct | ggagctccat | ccaccctgct | ctgaagggtg | taggcatcgc | ctccatgttc | 360 |
| gtgtccttca | tggtgggcct | gtactacaac | accatcatcg | cctgggtcat | gtggtatttc | 420 |
| ttcaactcct | ttcaggaacc | tctgccatgg | agcgaatgcc | cactcaacca | gaaccagaca | 480 |
| ggctatgtgg | aagagtgtgc | caagagctct | tctgtggact | acttctggta | ccgagagact | 540 |
| ctcaacatct | ccactcctat | cagtgactca | ggctccatcc | agtggtggat | cctgctctgc | 600 |
| ctgacatgtg | cctggagtgt | tctgtatgtg | tgtactatcc | gtggcatcga | gaccactggg | 660 |
| aaggctgttt | acatcacctc | caccctgccc | tatgtcgtac | tgaccatctt | tctcatccgt | 720 |
| ggcttgactc | tgaagggtgc | caccaacggc | attgtcttcc | ttttcacacc | caatatcaca | 780 |
| gagctgagca | accccaacac | gtggctggat | gcaggtgctc | aggtttacta | ctccttctca | 840 |
| ctggccttcg | ggggcctcat | ctccttctcc | agctacaact | ctgtacacaa | taattgtgag | 900 |
| atggattccg | tgatcgtgtc | catcatcaat | ggcttcacat | ctgtgtatgc | ggccaccgtg | 960 |
| gtctactcta | tcattggctt | cagggccacc | gagcgctttg | atgactgtgt | gaacacgaac | 1020 |
| atcctgaccc | tcatcaatgg | gttcgacctg | cccgagggca | atgtgactgc | ggagaacttc | 1080 |
| gaggccatc | aacattggtg | caatgccact | aatcccgagg | cctatgccca | gctgacgttt | 1140 |
| cagacctgtg | acattaacac | cttcctctct | gagggtgtag | agggcacagg | cctggccttc | 1200 |
| attgtcttca | ctgaagccat | cacgaagatg | ccagtgtccc | cactgtggtc | ggtgctcttc | 1260 |
| tttatcatgc | tcttctgcct | gggcctctcc | tctatgtttg | ggaacatgga | gggtgtggtc | 1320 |
| gtaccccttc | aggatctcaa | tatcaccccct | aagaagtggc | ccaaagaact | gctcacaggt | 1380 |
| ctcatctgct | ggggacata | tctcatcgcc | ttcattttca | cactgaattc | gggccagtac | 1440 |
| tggctctccc | tgctggacag | ctatgctggc | tccatccctc | tgctaatcat | cgccttttgt | 1500 |
| gagatgtttg | ctgtcgtcta | cgtgtatgga | gttgacaggt | tcaacaagga | catcgagttc | 1560 |
| atgatcggcc | ataagcccaa | catcttctgg | caagtcacgt | ggagagtggt | cagtccgctg | 1620 |
| atcatgctgg | tcatcttcct | cttcttttc | gtgattgaag | tcaacaaaca | gctcatgtat | 1680 |
| agcgtatggg | accctgacta | tgaggagttc | ccgaaatctc | agaaggttcc | ataccccgac | 1740 |
| tgggtgtacg | cagttgtggt | cattgtggct | ggagtaccct | gccttaccat | ccctgctttt | 1800 |
| gccatctaca | aactcatcag | aaactattgc | cagaagtctg | ggaccaaca | tgggctggtc | 1860 |
| aatgcgctgt | ccacagcctc | tgtgaatggg | gaccttaaga | actga | | 1905 |

<210> SEQ ID NO 9
<211> LENGTH: 2022
<212> TYPE: DNA
<213> ORGANISM: Homo sapiens

<400> SEQUENCE: 9

```
atggtgaggc tcgtgctgcc caaccccggc ctagacgccc ggatcccgtc cctggctgag    60
ctggagacca tcgagcagga ggaggccagc tcccggccga agtgggacaa caaggcgcag   120
tacatgctca cctgcctggg cttctgcgtg ggcctcggca acgtgtggcg cttcccctac   180
ctgtgtcaga gccacggagg aggagccttc atgatcccgt tcctcatcct gctggtcctg   240
gagggcatcc ccctgctgta cctggagttc gccatcgggc agcggctgcg gcggggcagc   300
ctgggtgtgt ggagctccat ccacccggcc ctgaagggcc taggcctggc ctccatgctc   360
acgtccttca tggtgggact gtattacaac accatcatct cctggatcat gtggtactta   420
ttcaactcct tccaggagcc tctgccctgg agcgactgcc cgctcaacga gaaccagaca   480
gggtatgtgg acgagtgcgc caggagctcc cctgtggact acttctggta ccgagagacg   540
ctcaacatct ccacgtccat cagcgactcg ggctccatcc agtggtggat gctgctgtgc   600
ctggcctgcg catggagcgt cctgtacatg tgcaccatcc gcggcatcga gaccaccggg   660
aaggccgtgt acatcacctc cacgctgccc tatgtcgtcc tgaccatctt cctcatccga   720
ggcctgacgc tgaagggcgc caccaatggc atcgtcttcc tcttcacgcc aacgtcacg    780
gagctggccc agccggacac ctggctggac gcgggcgcac aggtcttctt ctccttctcc   840
ctggccttcg ggggcctcat ctccttctcc agctacaact ctgtgcatgg ctcagcctct   900
cactcctggg gctggcgctc tgggcgggat gcggatgctg ccctgggctg tgtcctgacc   960
tgggacctca tcgccagccg ccatgacact ggtctcgtct gcagcaacaa ctgcgagaag  1020
gactcggtga ttgtgtccat catcaacggc ttcacatcgg tgtatgtggc catcgtggtc  1080
tactccgtca ttgggttccg cgccacacag cgctacgacg actgcttcag cacgaacatc  1140
ctgacccctca tcaacgggtt cgacctgcct gaaggcaacg tgacccagga gaactttgtg  1200
gacatgcagc agcggtgcaa cgcctccgac cccgcggcct acgcgcagct ggtgttccag  1260
acctgcgaca tcaacgcctt cctctcagag gccgtggagg gcacaggcct ggccttcatc  1320
gtcttcaccg aggccatcac caagatgccg ttgtccccac tgtggtctgt gctcttcttc  1380
attatgctct tctgcctggg gctgtcatct atgtttggga acatggaggg cgtcgttgtg  1440
cccctgcagg acctcagagt catccccccg aagtggccca aggaggtgct cacaggcctc  1500
atctgcctgg ggacattcct cattggcttc atcttcacgc tgaactccgg ccagtactgg  1560
ctctcccttgc tggacagcta tgccggctcc attcccctgc tcatcatcgc cttctgcgag  1620
atgttctctg tggtctacgt gtacggtgtg acaggttca ataaggacat cgagttcatg  1680
atcggccaca gcccaacat cttctggcaa gtcacgtggc gcgtggtcag ccccctgctc  1740
atgctgatca tcttcctctt cttcttcgtg gtagaggtca gtcaggagct gacctacagc  1800
atctgggacc ctgctacgga ggaatttccc aaatcccaga gatctcctca ccgaactgg   1860
gtgtatgtgg tggtggtgat tgtggctgga gtgccctccc tcaccatccc tggctatgcc  1920
atctacaagc tcatcaggaa ccactgccag aagccagggg accatcaggg gctggtgagc  1980
acactgtcca cagcctccat gaacgggggac ctgaagtact ga                    2022
```

<210> SEQ ID NO 10
<211> LENGTH: 672
<212> TYPE: PRT
<213> ORGANISM: Homo sapiens

<400> SEQUENCE: 10

Met Val Arg Leu Val Leu Pro Asn Pro Gly Leu Asp Ala Arg Ile Pro
1               5                   10                  15

-continued

```
Ser Leu Ala Glu Leu Glu Thr Ile Glu Gln Glu Ala Ser Ser Arg
            20              25              30

Pro Lys Trp Asp Asn Lys Ala Gln Tyr Met Leu Thr Cys Leu Gly Phe
        35              40              45

Cys Val Gly Leu Gly Asn Val Trp Arg Phe Pro Tyr Leu Cys Gln Ser
50              55              60

His Gly Gly Gly Ala Phe Met Ile Pro Phe Leu Ile Leu Val Leu
65              70              75              80

Glu Gly Ile Pro Leu Leu Tyr Leu Glu Phe Ala Ile Gly Gln Arg Leu
            85              90              95

Arg Arg Gly Ser Leu Gly Val Trp Ser Ser Ile His Pro Ala Leu Lys
            100             105             110

Gly Leu Gly Leu Ala Ser Met Leu Thr Ser Phe Met Val Gly Leu Tyr
            115             120             125

Tyr Asn Thr Ile Ile Ser Trp Ile Met Trp Tyr Leu Phe Asn Ser Phe
130             135             140

Gln Glu Pro Leu Pro Trp Ser Asp Cys Pro Leu Asn Glu Asn Gln Thr
145             150             155             160

Gly Tyr Val Asp Glu Cys Ala Arg Ser Ser Pro Val Asp Tyr Phe Trp
            165             170             175

Tyr Arg Glu Thr Leu Asn Ile Ser Thr Ser Ile Ser Asp Ser Gly Ser
            180             185             190

Ile Gln Trp Trp Met Leu Leu Cys Leu Ala Cys Ala Trp Ser Val Leu
            195             200             205

Tyr Met Cys Thr Ile Arg Gly Ile Glu Thr Thr Gly Lys Ala Val Tyr
210             215             220

Ile Thr Ser Thr Leu Pro Tyr Val Val Leu Thr Ile Phe Leu Ile Arg
225             230             235             240

Gly Leu Thr Leu Lys Gly Ala Thr Asn Gly Ile Val Phe Leu Phe Thr
            245             250             255

Pro Asn Val Thr Glu Leu Ala Gln Pro Asp Thr Trp Leu Asp Ala Gly
            260             265             270

Ala Gln Val Phe Phe Ser Phe Ser Leu Ala Phe Gly Gly Leu Ile Ser
            275             280             285

Phe Ser Ser Tyr Asn Ser Val His Gly Ser Ala Ser His Ser Trp Gly
290             295             300

Trp Arg Ser Gly Arg Asp Ala Asp Ala Ala Leu Gly Cys Val Leu Thr
305             310             315             320

Trp Asp Leu Ile Ala Ser Arg His Asp Thr Gly Leu Val Cys Ser Asn
            325             330             335

Asn Cys Glu Lys Asp Ser Val Ile Val Ser Ile Asn Gly Phe Thr
            340             345             350

Ser Val Tyr Val Ala Ile Val Tyr Ser Val Ile Gly Phe Arg Ala
            355             360             365

Thr Gln Arg Tyr Asp Asp Cys Phe Ser Thr Asn Ile Leu Thr Leu Ile
            370             375             380

Asn Gly Phe Asp Leu Pro Glu Gly Asn Val Thr Gln Glu Asn Phe Val
385             390             395             400

Asp Met Gln Gln Arg Cys Asn Ala Ser Asp Pro Ala Ala Tyr Ala Gln
            405             410             415

Leu Val Phe Gln Thr Cys Asp Ile Asn Ala Phe Leu Ser Glu Ala Val
            420             425             430

Glu Gly Thr Gly Leu Ala Phe Ile Val Phe Thr Glu Ala Ile Thr Lys
```

-continued

```
                435                 440                 445
Met Pro Leu Ser Pro Leu Trp Ser Val Leu Phe Phe Ile Met Leu Phe
450                 455                 460

Cys Leu Gly Leu Ser Ser Met Phe Gly Asn Met Glu Gly Val Val Val
465                 470                 475                 480

Pro Leu Gln Asp Leu Arg Val Ile Pro Pro Lys Trp Pro Lys Glu Val
            485                 490                 495

Leu Thr Gly Leu Ile Cys Leu Gly Thr Phe Leu Ile Gly Phe Ile Phe
                500                 505                 510

Thr Leu Asn Ser Gly Gln Tyr Trp Leu Ser Leu Leu Asp Ser Tyr Ala
            515                 520                 525

Gly Ser Ile Pro Leu Leu Ile Ile Ala Phe Cys Glu Met Phe Ser Val
530                 535                 540

Val Tyr Val Tyr Gly Val Asp Arg Phe Asn Lys Asp Ile Glu Phe Met
545                 550                 555                 560

Ile Gly His Lys Pro Asn Ile Phe Trp Gln Val Thr Trp Arg Val Val
            565                 570                 575

Ser Pro Leu Leu Met Leu Ile Ile Phe Leu Phe Phe Val Val Glu
                580                 585                 590

Val Ser Gln Glu Leu Thr Tyr Ser Ile Trp Asp Pro Gly Tyr Glu Glu
            595                 600                 605

Phe Pro Lys Ser Gln Lys Ile Ser Tyr Pro Asn Trp Val Tyr Val Val
610                 615                 620

Val Val Ile Val Ala Gly Val Pro Ser Leu Thr Ile Pro Gly Tyr Ala
625                 630                 635                 640

Ile Tyr Lys Leu Ile Arg Asn His Cys Gln Lys Pro Gly Asp His Gln
            645                 650                 655

Gly Leu Val Ser Thr Leu Ser Thr Ala Ser Met Asn Gly Asp Leu Lys
                660                 665                 670
```

<210> SEQ ID NO 11
<211> LENGTH: 3252
<212> TYPE: DNA
<213> ORGANISM: Homo sapiens

<400> SEQUENCE: 11

```
gcggcccagg cccgcaacct tccctggtcg tgcgccctat gtaaggccag ccgcggcagg      60
accaaggcgg cggtgtcagc tcgcgagcct accctccgcg gacggtcttg ggtcgcctgc     120
tgcctggctt gcctggtcgg cggcgggtgc ccgcgcgca cgcgcaaagc cgccgcgtt      180 ccccgacccc aggccgcgct ctgtgggcct ctgagggcgg catgcgggac tacgacgagg     240
tgaccgcctt cctgggcgag tggggcccct tccagcgcct catcttcttc ctgctcagcg     300
ccagcatcat ccccaatggc ttcaccggcc tgtcctccgt gttcctgata gcgacccgg     360 agcaccgctg ccgggtgccg gacgccgcga acctgagcag cgcctggcgc aaccacactg     420
tcccactgcg gctgcgggac ggccgcgagg tgccccacag ctgccgccgc taccggctcg     480
ccaccatcgc caacttctcg gcgcttgggc tggagccggg gcgcgacgtg gacctggggc     540
agctggagca ggagagctgt ctggatggct gggagttcag tcaggacgtc tacctgtcca     600
ccattgtgac cgagtggaac ctggtgtgtg aggacgactg gaaggcccca ctcacaatct     660
ccttgttctt cgtgggtgtg ctgttgggct ccttcatttc agggcagctg tcagacaggt     720
ttggccggaa gaatgctgc ttcgtgacca tgggcatgca gacaggcttc agcttcctgc     780
agatcttctc gaagaatttt gagatgtttg tcgtgctgtt tgtccttgta ggcatggggcc     840
```

-continued

```
agatctccaa ctatgtggca gcatttgtcc tggggacaga aattcttggc aagtcagttc    900
gtataatatt ctctacgtta ggagtgtgca tattttatgc atttggctac atggtgctgc    960
cactgtttgc ttacttcatc cgagactggc ggatgctgct ggtggcgctg acgatgccgg   1020
gggtgctatg cgtggcactc tggtggttca tccctgagtc cccccgatgg ctcatctctc   1080
agggacgatt tgaagaggca gaggtgatca tccgcaaggc tgccaaagcc aatgggattg   1140
ttgtgccttc cactatcttt gacccgagtg agttacaaga cctaagttcc aagaagcagc   1200
agtcccacaa cattctggat ctgcttcgaa cctggaatat ccggatggtc accatcatgt   1260
ccataatgct gtggatgacc atatcagtgg gctattttgg gctttcgctt gatactccta   1320
acttgcatgg ggacatcttt gtgaactgct cctttcagc gatggttgaa gtcccagcat   1380
atgtgttggc ctgctgctg ctgcaatatt tgccccggcg ctattccatg ccactgccc   1440
tcttcctggg tggcagtgtc cttctcttca tgcagctggt accccagac ttgtattatt   1500
tggctacagt cctggtgatg gtgggcaagt ttggagtcac ggctgccttt tccatggtct   1560
acgtgtacac agccgagctg tatcccacag tggtgagaaa catgggtgtg ggagtcagct   1620
ccacagcatc ccgcctgggc agcatcctgt ctccctactt cgtttaccTT ggtgcctacg   1680
accgcttcct gccctacatt tcatgggaa gtctgaccat cctgacagcc atcctcacct   1740
tgtttctccc agagagcttc ggtacccac tcccagacac cattgaccag atgctaagag   1800
tcaaaggaat gaaacacaga aaaactccaa gtcacacaag gatgttaaaa gatggtcaag   1860
aaaggcccac aatccttaaa agcacagcct tctaacatcg cttccagtaa gggagaaact   1920
gaagaggaaa gactgtcttg ccagaaatgg ccagcttgtg cagactccga gtccttcagt   1980
gacaaaggcc tttgctgttt gtcctcttga cctgtgtctg acttgctcct ggatgggcac   2040
ccacactcag aggctacata tggccctaga gcaccacctt cctctaggga cactggggct   2100
acctacagac aacttcatct aagtcctaac tattacaatg atggactcag cacctccaaa   2160
gcagttaatt tttcactaga accagtgaga tctggaggaa tgtgagaagc atatgctaaa   2220
tgtacatttt aattttagac tacttgaaaa ggcccctaat aaggctagag gtctaagtcc   2280
cccaccccTT tccccactcc cctctagtgg tgaactttag aggaaaagga agtaattgca   2340
caaggagttt gattcttacc ttttctcagt tacagaggac attaactgga tcattgcttc   2400
cccagggcag gagagcgcag agctagggaa agtgaaaggt aatgaagatg gagcagaatg   2460
agcagatgca gatcaccagc aaagtgcact gatgtgtgag ctcttaagac cactcagcat   2520
gacgactgag tagacttgtt tacatctgat caaagcactg ggcttgtcca ggctcataat   2580
aaatgctcca ttgaatctac tattcttgtt ttccactgct gtggaaacct ccttgctact   2640
atagcgtctt atgtatggtt taaaggaaat ttatcaggtg agagagatga gcaacgttgt   2700
cttttctctc aaagctgtaa tgtgggtttt gttttattgt ttatttgttt gttgttgtat   2760
cctttctcc ttgttatttg cccttcagaa tgcacttggg aaaggctggt tccttagcct   2820
cctggtttgt gtcttttttt ttttttttt aaacacagaa tcactctggc aattgtctgc   2880
agctgccact ggtgcaaggc cttaccagcc ctagcctcta gcacttctct aagtgccaaa   2940
aacagtgtca ttgtgtgtgt tccttttcttg atacttagtc atgggaggat attacaaaaa   3000
agaaatttaa attgtgttca tagtctttca gagtagctca ctttagtcct gtaactttat   3060
tgggtgatat tttgtgttca gtgtaattgt cttctctttg ctgattatgt taccatggta   3120
ctcctaaagc atatgcctca cctggttaaa aaagaacaaa catgttttg tgaaagctac   3180
```

```
tgaagtgcct tgggaaatga gaaagtttta ataagtaaaa tgattttta aatatcaaaa    3240 aaaaaaaaaa aa                                                       3252
```

<210> SEQ ID NO 12
<211> LENGTH: 557
<212> TYPE: PRT
<213> ORGANISM: Homo sapiens

<400> SEQUENCE: 12

```
Met Arg Asp Tyr Asp Glu Val Thr Ala Phe Leu Gly Glu Trp Gly Pro
1               5                   10                  15

Phe Gln Arg Leu Ile Phe Phe Leu Leu Ser Ala Ser Ile Ile Pro Asn
            20                  25                  30

Gly Phe Thr Gly Leu Ser Ser Val Phe Leu Ile Ala Thr Pro Glu His
        35                  40                  45

Arg Cys Arg Val Pro Asp Ala Ala Asn Leu Ser Ser Ala Trp Arg Asn
    50                  55                  60

His Thr Val Pro Leu Arg Leu Arg Asp Gly Arg Glu Val Pro His Ser
65                  70                  75                  80

Cys Arg Arg Tyr Arg Leu Ala Thr Ile Ala Asn Phe Ser Ala Leu Gly
                85                  90                  95

Leu Glu Pro Gly Arg Asp Val Asp Leu Gly Gln Leu Glu Gln Glu Ser
            100                 105                 110

Cys Leu Asp Gly Trp Glu Phe Ser Gln Asp Val Tyr Leu Ser Thr Ile
        115                 120                 125

Val Thr Glu Trp Asn Leu Val Cys Glu Asp Asp Trp Lys Ala Pro Leu
130                 135                 140

Thr Ile Ser Leu Phe Phe Val Gly Val Leu Leu Gly Ser Phe Ile Ser
145                 150                 155                 160

Gly Gln Leu Ser Asp Arg Phe Gly Arg Lys Asn Val Leu Phe Val Thr
                165                 170                 175

Met Gly Met Gln Thr Gly Phe Ser Phe Leu Gln Ile Phe Ser Lys Asn
            180                 185                 190

Phe Glu Met Phe Val Val Leu Phe Val Leu Val Gly Met Gly Gln Ile
        195                 200                 205

Ser Asn Tyr Val Ala Ala Phe Val Leu Gly Thr Glu Ile Leu Gly Lys
    210                 215                 220

Ser Val Arg Ile Ile Phe Ser Thr Leu Gly Val Cys Ile Phe Tyr Ala
225                 230                 235                 240

Phe Gly Tyr Met Val Leu Pro Leu Phe Ala Tyr Phe Ile Arg Asp Trp
                245                 250                 255

Arg Met Leu Leu Val Ala Leu Thr Met Pro Gly Val Leu Cys Val Ala
            260                 265                 270

Leu Trp Trp Phe Ile Pro Glu Ser Pro Arg Trp Leu Ile Ser Gln Gly
        275                 280                 285

Arg Phe Glu Glu Ala Glu Val Ile Ile Arg Lys Ala Ala Lys Ala Asn
    290                 295                 300

Gly Ile Val Val Pro Ser Thr Ile Phe Asp Pro Ser Glu Leu Gln Asp
305                 310                 315                 320

Leu Ser Ser Lys Lys Gln Gln Ser His Asn Ile Leu Asp Leu Leu Arg
                325                 330                 335

Thr Trp Asn Ile Arg Met Val Thr Ile Met Ser Ile Met Leu Trp Met
            340                 345                 350

Thr Ile Ser Val Gly Tyr Phe Gly Leu Ser Leu Asp Thr Pro Asn Leu
```

```
                     355                 360                 365
His Gly Asp Ile Phe Val Asn Cys Phe Leu Ser Ala Met Val Glu Val
    370                 375                 380

Pro Ala Tyr Val Leu Ala Trp Leu Leu Leu Gln Tyr Leu Pro Arg Arg
385                 390                 395                 400

Tyr Ser Met Ala Thr Ala Leu Phe Leu Gly Gly Ser Val Leu Leu Phe
                405                 410                 415

Met Gln Leu Val Pro Pro Asp Leu Tyr Tyr Leu Ala Thr Val Leu Val
                420                 425                 430

Met Val Gly Lys Phe Gly Val Thr Ala Ala Phe Ser Met Val Tyr Val
                435                 440                 445

Tyr Thr Ala Glu Leu Tyr Pro Thr Val Val Arg Asn Met Gly Val Gly
    450                 455                 460

Val Ser Ser Thr Ala Ser Arg Leu Gly Ser Ile Leu Ser Pro Tyr Phe
465                 470                 475                 480

Val Tyr Leu Gly Ala Tyr Asp Arg Phe Leu Pro Tyr Ile Leu Met Gly
                485                 490                 495

Ser Leu Thr Ile Leu Thr Ala Ile Leu Thr Leu Phe Leu Pro Glu Ser
                500                 505                 510

Phe Gly Thr Pro Leu Pro Asp Thr Ile Asp Gln Met Leu Arg Val Lys
                515                 520                 525

Gly Met Lys His Arg Lys Thr Pro Ser His Thr Arg Met Leu Lys Asp
                530                 535                 540

Gly Gln Glu Arg Pro Thr Ile Leu Lys Ser Thr Ala Phe
545                 550                 555

<210> SEQ ID NO 13
<211> LENGTH: 1983
<212> TYPE: DNA
<213> ORGANISM: Homo sapiens

<400> SEQUENCE: 13
ggggcggggc gcgctacccg cagcccccgg agctcggcta actcggcgcc cagtgcacgg      60
ccgcaccatg gggtcccgcc acttcgaggg gatttatgac cacgtggggc acttcggcag     120
attccagaga gtcctctatt tcatatgtgc cttccagaac atctcttgtg gtattcacta     180
cttggcttct gtgttcatgg gagtcacccc tcatcatgtc tgcaggcccc caggcaatgt     240
gagtcaggtt gttttccata atcactctaa ttggagtttg gaggacaccg gggccctgtt     300
gtcttcaggc cagaaagatt atgttacggt gcagttgcag aatggtgaga tctgggagct     360
ctcaaggtgt agcaggaata agagggagaa cacatcgagt ttgggctatg aatacactgg     420
cagtaagaaa gagtttcctt gtgtggatgg ctacatatat gaccagaaca catggaaaag     480
cactgcggtg acccagtgga acctggtctg tgaccgaaaa tggcttgcaa tgctgatcca     540
gccctatttt atgtttggag tcctactggg atcggtgact tttggctact ttctgacagc     600
gctaggacgc cgggtggtct tgtgggccac aagcagtagc atgttttttgt ttggaatagc     660 agcggcgttt gcagttgatt attacacctt catggctgct cgcttttttc ttgccatggt     720
tgcaagtggc tatcttgtgg tgggtttgt ctatgtgatg gaattcattg gcatgaagtc     780
tcggacatgg gcgtctgtcc atttgcattc cttttttgca gttggaaccc tgctggtggc     840
tttgacagga tacttggtca ggacctggtg gctttaccag atgatcctct ccacagtgac     900
tgtccccttt atcctgtgct gttgggtgct cccagagaca cctttttggc ttctctcaga     960
gggacgatat gaagaagcac aaaaaatagt tgacatcatg gccaagtgga caggggcaag    1020
```

-continued

```
ctcctgtaaa ctgtcagaac ttttatcact ggacctacaa ggtcctgtta gtaatagccc      1080
cactgaagtt cagaagcaca acctatcata tctgttttat aactggagca ttacgaaaag      1140
gacacttacc gtttggctaa tctggttcac tggaagtttg ggattctact cgttttcctt      1200
gaattctgtt aacttaggag gcaatgaata cttaaacctc ttcctcctgg gtgtagtgga      1260
aattcccgcc tacaccttcg tgtgcatcgc catggacaag gtcggggagga gaacagtcct      1320 ggcctactct cttttctgca gtgcactggc ctgtggtgtc gttatggtga tcccccagaa      1380
acattatatt ttgggtgtgg tgacagctat ggttggaaaa tttgccatcg ggcagcatt       1440 tggcctcatt tatctttata cagctgagct gtatccaacc attgtaagat cgctggctgt      1500
gggaagcggc agcatggtgt gtcgcctggc cagcatcctg cgccgttct ctgtggacct       1560 cagcagcatt tggatcttca taccacagtt gtttgttggg actatggccc tcctgagtgg      1620
agtgttaaca ctaaagcttc cagaaaccct tgggaaacgg ctagcaacta cttgggagga     1680
ggctgcaaaa ctggagtcag agaatgaaag caagtcaagc aaattacttc tcacaactaa      1740
taatagtggg ctgaaaaaaa cggaagcgat taccccagg gattctggtc ttggtgaata       1800
aatgtgccat gcctgctgtc tagcacctga aatattattt accctaatgc ctttgtatta     1860
gaggaatctt attctcatct cccatatgtt gtttgtatgt cttttttaata aattttgtaa     1920 gaaaatttta aagcaaatat gttataaaag aaataaaaac taagatgaaa aaaaaaaaaaa    1980 aaa                                                                  1983
```

<210> SEQ ID NO 14
<211> LENGTH: 577
<212> TYPE: PRT
<213> ORGANISM: Homo sapiens

<400> SEQUENCE: 14

```
Met Gly Ser Arg His Phe Glu Gly Ile Tyr Asp His Val Gly His Phe
1               5                   10                  15

Gly Arg Phe Gln Arg Val Leu Tyr Phe Ile Cys Ala Phe Gln Asn Ile
            20                  25                  30

Ser Cys Gly Ile His Tyr Leu Ala Ser Val Phe Met Gly Val Thr Pro
        35                  40                  45

His His Val Cys Arg Pro Pro Gly Asn Val Ser Gln Val Phe His
    50                  55                  60

Asn His Ser Asn Trp Ser Leu Glu Asp Thr Gly Ala Leu Leu Ser Ser
65                  70                  75                  80

Gly Gln Lys Asp Tyr Val Thr Val Gln Leu Gln Asn Gly Glu Ile Trp
                85                  90                  95

Glu Leu Ser Arg Cys Ser Arg Asn Lys Arg Glu Asn Thr Ser Ser Leu
            100                 105                 110

Gly Tyr Glu Tyr Thr Gly Ser Lys Lys Glu Phe Pro Cys Val Asp Gly
        115                 120                 125

Tyr Ile Tyr Asp Gln Asn Thr Trp Lys Ser Thr Ala Val Thr Gln Trp
    130                 135                 140

Asn Leu Val Cys Asp Arg Lys Trp Leu Ala Met Leu Ile Gln Pro Leu
145                 150                 155                 160

Phe Met Phe Gly Val Leu Leu Gly Ser Val Thr Phe Gly Tyr Phe Ser
                165                 170                 175

Asp Arg Leu Gly Arg Arg Val Val Leu Trp Ala Thr Ser Ser Ser Met
            180                 185                 190
```

Phe Leu Phe Gly Ile Ala Ala Ala Phe Ala Val Asp Tyr Tyr Thr Phe
            195                 200                 205

Met Ala Ala Arg Phe Phe Leu Ala Met Val Ala Ser Gly Tyr Leu Val
        210                 215                 220

Val Gly Phe Val Tyr Val Met Glu Phe Ile Gly Met Lys Ser Arg Thr
225                 230                 235                 240

Trp Ala Ser Val His Leu His Ser Phe Ala Val Gly Thr Leu Leu
                245                 250                 255

Val Ala Leu Thr Gly Tyr Leu Val Arg Thr Trp Leu Tyr Gln Met
                260                 265                 270

Ile Leu Ser Thr Val Thr Val Pro Phe Ile Leu Cys Cys Trp Val Leu
        275                 280                 285

Pro Glu Thr Pro Phe Trp Leu Leu Ser Glu Gly Arg Tyr Glu Glu Ala
        290                 295                 300

Gln Lys Ile Val Asp Ile Met Ala Lys Trp Asn Arg Ala Ser Ser Cys
305                 310                 315                 320

Lys Leu Ser Glu Leu Leu Ser Leu Asp Leu Gln Gly Pro Val Ser Asn
                325                 330                 335

Ser Pro Thr Glu Val Gln Lys His Asn Leu Ser Tyr Leu Phe Tyr Asn
            340                 345                 350

Trp Ser Ile Thr Lys Arg Thr Leu Thr Val Trp Leu Ile Trp Phe Thr
        355                 360                 365

Gly Ser Leu Gly Phe Tyr Ser Phe Ser Leu Asn Ser Val Asn Leu Gly
    370                 375                 380

Gly Asn Glu Tyr Leu Asn Leu Phe Leu Leu Gly Val Val Glu Ile Pro
385                 390                 395                 400

Ala Tyr Thr Phe Val Cys Ile Ala Met Asp Lys Val Gly Arg Arg Thr
            405                 410                 415

Val Leu Ala Tyr Ser Leu Phe Cys Ser Ala Leu Ala Cys Gly Val Val
                420                 425                 430

Met Val Ile Pro Gln Lys His Tyr Ile Leu Gly Val Val Thr Ala Met
        435                 440                 445

Val Gly Lys Phe Ala Ile Gly Ala Ala Phe Gly Leu Ile Tyr Leu Tyr
    450                 455                 460

Thr Ala Glu Leu Tyr Pro Thr Ile Val Arg Ser Leu Ala Val Gly Ser
465                 470                 475                 480

Gly Ser Met Val Cys Arg Leu Ala Ser Ile Leu Ala Pro Phe Ser Val
                485                 490                 495

Asp Leu Ser Ser Ile Trp Ile Phe Ile Pro Gln Leu Phe Val Gly Thr
            500                 505                 510

Met Ala Leu Leu Ser Gly Val Leu Thr Leu Lys Leu Pro Glu Thr Leu
        515                 520                 525

Gly Lys Arg Leu Ala Thr Thr Trp Glu Glu Ala Lys Leu Glu Ser
    530                 535                 540

Glu Asn Glu Ser Lys Ser Ser Lys Leu Leu Leu Thr Thr Asn Asn Ser
545                 550                 555                 560

Gly Leu Glu Lys Thr Glu Ala Ile Thr Pro Arg Asp Ser Gly Leu Gly
                565                 570                 575

Glu

<210> SEQ ID NO 15
<211> LENGTH: 5175
<212> TYPE: DNA
<213> ORGANISM: Homo sapiens

<400> SEQUENCE: 15

```
agcttctgcc ctgcctgctg tgtgcggagc cgtccagcga ccaccatggt gaggctcgtg      60
ctgcccaacc ccggcctaga cgcccggatc ccgtccctgg ctgagctgga gaccatcgag     120
caggaggagg ccagctcccg gccgaagtgg gacaacaagg cgcagtacat gctcacctgc     180
ctgggcttct gcgtgggcct cggcaacgtg tggcgcttcc cctacctgtg tcagagccac     240
ggaggaggag ccttcatgat cccgttcctc atcctgctgg tcctggaggg catcccctg     300
ctgtacctgg agttcgccat cgggcagcgg ctgcggcggg cagcctgggt gtgtggagc     360
tccatccacc cggccctgaa gggcctaggc ctggcctcca tgctcacgtc cttcatggtg     420
ggactgtatt acaacaccat catctcctgg atcatgtggt acttattcaa ctccttccag     480
gagcctctgc cctggagcga ctgcccgctc aacgagaacc agacagggta tgtggacgag     540
tgcgccagga gctcccctgt ggactacttc tggtaccgag agacgctcaa catctccacg     600
tccatcagcg actcgggctc catccagtgg tggatgctgc tgtgcctggc ctgcgcatgg     660
agcgtcctgt acatgtgcac catccgcggc atcgagacca ccgggaaggc cgtgtacatc     720
acctccacgc tgcccctatgt cgtcctgacc atcttcctca tccgaggcct gacgctgaag     780
ggcgccacca atggcatcgt cttcctcttc acgcccaacg tcacggagct ggcccagccg     840
gacacctggc tggacgcggg cgcacaggtc ttcttctcct ctcccctggc cttcgggggc     900
ctcatctcct ctccagcta caactctgtg cacaacaact gcgagaagga ctcggtgatt     960
gtgtccatca tcaacggctt cacatcgtg tatgtgccac tcgtggtcta ctccgtcatt    1020
gggttccgcg ccacgcagcg ctacgacgac tgcttcagca cgaacatcct gaccctcatc    1080
aacgggttcg acctgcctga aggcaacgtg acccaggaga ctttgtgga catgcagcag    1140
cggtgcaacg cctccgaccc cgcggcctac gcgcagctgg tgttccagac ctgcgacatc    1200
aacgccttcc tctcagaggc cgtggagggc acaggcctgg ccttcatcgt cttcaccgag    1260
gccatcacca agatgccgtt gtccccactg tggtctgtgc tcttcttcat tatgctcttc    1320
tgcctggggc tgtcatctat gtttgggaac atggagggcg tcgttgtgcc cctgcaggac    1380
ctcagagtca tcccccgaa gtggcccaag gaggtgctca caggcctcat ctgcctgggg    1440
acattcctca ttggcttcat cttcacgctg aactccggcc agtactggct ctccctgctg    1500
gacagctatg ccggctccat tccctgctc atcatcgcct tctgcgagat gttctctgtg    1560
gtctacgtgt acggtgtgga caggttcaat aaggacatcg agttcatgat cggccacaag    1620
cccaacatct tctggcaagt cacgtggcgc gtggtcagcc ccctgctcat gctgatcatc    1680
ttcctcttct tcttcgtggt agaggtcagt caggagctga cctacagcat ctgggaccct    1740
ggctacgagg aatttcccaa atcccagaag atctcctacc cgaactgggt gtatgtggtg    1800
gtggtgattg tggctggagt gcccctccctc accatccctg ctatgccat ctacaagctc    1860
atcaggaacc actgccagaa gccagggggac catcaggggc tggtgagcac actgtccaca    1920
gcctccatga cggggaccct gaagtactga gaaggcccat cccacggcgt gccatacact    1980
ggtgtcaggg aaggaggaac cagcaagacc tgtggggtgg gggccgggct gcacctgcat    2040
gtgtgtaagc gtgagtgtat gctcgtgtgt gagtgtgtgt attgtacacg catgtgccat    2100
gtgtgcagat atgtatcgtg tgtgcatgta catgcatggg cactgtgagt gtgcacgtgt    2160
atgcacacat atacatgtgt gtgggtgtgt gtattgtatg tgcatgtgcc atgtgtgcag    2220
atgtgtcatg ttgtgtgtgt gcatgtacat gtatggacat tgtgtgagtg tgcaagtgtg    2280
```

```
catgcatata catgtgtgcg atatttgctg cccgtgtgtg tgcatgtata tatagacata    2340
catgcctatg ttgtgtgtgg tgtgcatatg tgtgaacaca cacgtgtata catgcatgca    2400
catgtgctcg tacaatgggt gtccacatgc acgtgtatat gtatatctgt gagtgtatat    2460
acatgcatgc aattgtgtgt atgtgtgttc tgtgtgtgcg tttgcaagta tatatgcaca    2520
tgtgtatatg tacatgtatg cctgtgtgac gtgtgtatat gtgagcatgt gtacgtgtgt    2580
gtatacgtgt gttgtgtata tgtgtgtgtc tgtacctgtt tgtgtatatg tgtgtgatgt    2640
gtgctcgtgt gtgtgcatat tcaggcaggt gtgcatttgt gcatcccagt gtgtatgtat    2700
gtgcgcatat ggacacgcat ggacacgcat atggacacat atggacacac atatggacac    2760
gtgtggatat gtgtgcgtac acgtcgctgg gacacatgcc tgccactcgg ggcccagctg    2820
accctctgtg tttgtccttg ccacagtcac ggggtgcatg tgcagagggg agcagaccac    2880
tggggacgtg ctgtgccctg cacgtgcccg ggggaagcgg aagctgcagc tggggtgggg    2940
gcagcaccte tatgcttcat ctctgtgggt ggcaggagac aaaagcacag ggtactatct    3000
tggctcctgg gagcgactct tgctacccac ccccacccat cccccttccc ttggtgttga    3060
cctttgacct gggggttccc agagccctgt agccctcgac ccggagcagc ctctcggaag    3120
ccggagtggg cagttgctgg cgattctgag aaaacttggc cgcatccacc ggggccctgc    3180
ctccagtcgg ccgctgccga gtctctgcgt tctggccgct tcccggctta atgaatgcca    3240
gccatttaat cattgctcct gccaccacaa atagatgagc agttaaataa aactcaactt    3300
ggcataattc aaggcaaata ccactctgtg cattttctta agaggacatg agctgtgtga    3360
attttttagcc agcctttgga aaagatgggt tacagggtaa ctcaaccctg gctgccatcc    3420
ttgggcactg tgtgtgtcca gggcaccttg gaggaccgtg cagcccccag aagcttccag    3480
ctcccgcacc actcagtgaa gcccagcctg gcgcctgccc tgccccgtc acgggatggg    3540
cccccattgg ggttcaacat tccatcgcag ccaaaggcag tcggcacttg ggacatctgc    3600
ttccacggac aggtcacctc cgctttgcac ggaagaatct ggatgcttac attaaactga    3660
tgttctgaga gttcctacgg acaggtcacc tccgctttgc atggaagaat ctggatgctt    3720
acattaaact ggtgttctga gagttcctac ggacaggtca cctccgcttt ccatagaaga    3780
atctggacgc ttacattaaa ctgatgttct gagaattcct acaggcagga ctgaaagcct    3840
ggtgtgtgcc agtatgatgt tccacccacg gaaacctggt cacaatcgtc ccttccagca    3900
ccccatccag cagtgactgc acacactgag cccctacca gcccctttca ccctgctgac    3960
tgtcactggg ccctgggatg tgcaagactc cacagcagca gaggtggggg gacatatcac    4020
agcctctgcc cccggctgtg atgccaccga ggggctcgcc tgctgatggc ttcaacaggg    4080
tctcacctca tcttttcctg ctctttggcc ctggatcgag aaaatttcca tcagtgcccc    4140
attaatatgc tgccctgtgg catctgccca ggaggccctg ccaggcgtgc acaggtgtgc    4200
attggtgtac cctggcatgc acaggtgtgc actgatgtgc cctggcatcc attggtgtac    4260
cctggtgtgc ctgccatagg accctgggcg ggagctccca tctcatctac atctcctgat    4320
tcatgcgttg tttcataggt ttcaatgtct ctgtaaatgt ggtagaaatg caggctttat    4380
gggcataaag tgtacatttc taaataaatc ccttctattt agtatgctca ccctagaagt    4440
tactgttgtc cagacgtaga gggatgagtg agccagtgac ctcagacggg atggtgggga    4500
cggcaggtcc agctcctgcc tcctcctggg gggtctggct ttgggggctt gctccgaaga    4560
ggccatggcc caggcctgtg gcctcacaat ggggaccaac cagctcttct catcttcttc    4620
cctcacactt cctctcactc aaataagaac cttccaaaaa tgtgtccacc tgggcccctg    4680
```

```
ccctgggact catggatttg gagttgtggc cacacggttg aggggtgcag tgtccagtgg   4740 aatgggcaa ttgcgggcct gggggccctt ggcctgtccg tggcgggagc atctgcaagg    4800
aggagcccca gagtccaggg agcactgtgg ggagctcctt agagctgaac tcacccggcg   4860
tcaactcatc aaccctccac ccatggacag gggtgccccc agcacaggag aggactcagc   4920
cctctgcccc cacgcacggt gggtgcctgt caccctgtcc tgcccagcgg cccgagggca   4980
gcagtgggtg tgagggcagc ccccggcctc ccaagagcag ctgagaggat ccctgcggga   5040
atccgggctt cgggtgcatg cgatctgatc tgagttgttt ctgacagtga cagagtgaca   5100
atctataagt atctcaagat caaatggtta aataaaacat aagaaattta aaacgattaa   5160
aaaaaaaaaa aaaaa                                                   5175
```

METHOD OF SCREENING FOR A CARNITINE TRANSPORTER AGONIST OR ANTAGONIST AND ITS USES

The present invention is directed to a method of screening for a carnitine transporter agonist or for a carnitine transporter antagonist, to a kit for carrying out the method for screening for a carnitine transporter agonist or for a carnitine transporter antagonist, to a method for the manufacture of a medicament for the treatment of a carnitine transporter deficiency, to methods of diagnosis of a carnitine transporter deficiency, to the use of a protein for the manufacture of an antibody reacting with a carnitine transporter, to an oligonucleotide and to methods of treatment of a carnitine transporter deficiency.

Carnitine deficiency in humans leads to a variety of severe symptoms (Rodriguez P. R. et al, 1988, Eur. J. Pediatr., 148, 193-197). Among the most severe symptoms are cardiomyopathia, cronical amyasthenia and coma, which are caused by hypoglycaemia, or by failure of ketogenesis upon fasting, which are consequences of low serum levels of carnitine in the tissues, in particular in the liver, the kidneys, the heart, in muscles and in the intestine.

The symptoms of carnitine deficiency have been assumed to be a consequence of a deficiency of carnitine transport in the kidneys and in the intestine (Rodriguez P. R. et al, 1988). Disturbance of the carnitine transport system in the kidneys and in the intestine may lead to disturbances in the transport and in the degradation of fatty acids, which leads to a variety of severe symptoms, in particular to progressive amyasthenia, which can be diagnosed through a lipidmyopathy and a low muscular carnitine level, and to cardiomyopathia and respiratory disturbance, hypotension, respiratory insufficiency, hypoglycemia, hepatomegaly, liver failure, arrhythmia, loss of consciousness, hypertrophic or dilatative cardiomyopathia, cot death, coma, liver function disturbance, rhabdomyolysis, peripheral neuropathy, retinopathy, hepatopathy, congenital dysmorphism with midfacial hypoplasia, renal cysts, dystonia, neonatal cardiomyopathia, microcephaly, dysmorphism. Systemic carnitine deficiency is a hereditary disease and its symptoms often occur already in new borns and in small children.

So far, only a mechanism contributing to a rare autosomal recessive form of hereditary carnitine deficiency is known, wherein mutations in the carnitine transporter hOCTN2 contribute to a reduced carnitine level (Nezu J. I. et al. 1999, Nature Genet. 21:91-94). hOCTN2, whose amino acid sequence is available in the NCBI database under the accession number NP_003051, corresponding to SEQ ID NO: 12 herein, is however not synthesized in a tissue-specific way in the intestine or in the kidneys, but it is synthesized ubiquitously in the human body. Thus, the major mechanisms mediating carnitine uptake from the diet and carnitine homeostasis in the kidneys by recovery of carnitine from the renal filtrate (Rodriguez P. R. et al, 1988) are still unknown.

In addition, OCTN2 is not sufficient to mediate carnitine uptake in the intestine and in the kidneys, since it has been detected only on the luminal side of the intestinal and kidney epithelium, but not on the distal side where carnitine needs to be transported to the blood vessels (Lahjouji K et al. 2002, Biochim Biophys Acta 1558: 82-93). Intriguingly, there are reports about patients suffering from systemic carnitine deficiency which can only be treated by intravenous administration of carnitine, but not by dietary carnitine administration (Rodriguez P. R. et al. 1988, Eur. J. Pediatr. 148: 193-197).

Hence, a deficiency of hOCTN2 is not a suitable marker for the majority of carnitine deficiency syndromes.

Further, the protein CT2, whose amino acid sequence is available under the accession number NP_149116 in the NCBI database (National Center for Biotechnology Information USA), corresponding to SEQ ID NO: 14 herein, is a human carnitine transporter formed in testes only. Hence, its deficiency could not account for the symptoms of systemic carnitine deficiency.

WO 2001077174 discloses a protein corresponding to SEQ ID NO: 1 herein, however, no information about a function of the protein as a carnitine transporter has been provided. An amino acid sequence available under the accession number XM_291120 in the NCBI database, corresponding to SEQ ID NO: 10 herein, comprises the entire amino acid sequence of SEQ ID NO: 1 and an additional sequence comprising 39 amino acids (corresponding to amino acids 297 to 335 in SEQ ID NO: 10) between amino acids 296 and 297 of SEQ ID NO: 1 and is therefore a splice variant of SEQ ID NO: 1. U.S. Pat. No. 5,559,021 discloses the rat protein AAW07635 (rB21a) which shares 47% amino acid sequence identity with SEQ ID NO: 1 herein, however, no information about a function of the protein as a carnitine transporter has been provided. A human sequence corresponding to AAW07635 can be found in the NCBI database under the Accession Number AJ276207, which shares 46% amino acid sequence identity to SEQ ID NO: 1 herein, however, it has been supposed to be a neurotransmitter transporter. CN 1287170 discloses the protein AAG64193, which shares 47% amino acid sequence identity with SEQ ID NO: 1 herein, however it has been supposed to be a human nerve mass-transferring protein. EP 881290 discloses the AAW73376 protein, namely human HPDDV78, which shares 46% amino acid sequence identity with SEQ ID NO: 1 herein, however it has been supposed to be a neurotransmitter transporter. The mouse and the rat amino acid sequences SEQ ID NO: 2 and SEQ ID NO: 3 comprised herein form part of sequences available in public data bases, which however have not been annotated and have not been supposed to comprise a carnitine transporter.

From the above, no tissue-specifically synthesized carnitine transporter of the intestine or of the kidneys and hence no enzyme whose deficiency could account for the majority of carnitine deficiency syndromes known.

Therefore, there are at present no diagnostic ways to detect the majority of carnitine deficiency syndromes at the level of the carnitine transporter, but the detection of the relevant enzymes has to be awaited. Further, there are at present no therapeutic ways for the treatment of systemic carnitine deficiency at the level of the relevant disturbed enzymatic activity. At present the only available therapeutic way is the administration of carnitine, which has often the problem of a reduced or even missing uptake of carnitine from the intestine.

In view of the above there is a need to provide new ways to diagnose and treat carnitine deficiency. Therefore, it is an object of the present invention to provide new ways for the diagnosis of carnitine deficiency. A further object of the present invention refers to new therapeutic ways to treat carnitine deficiency. Still further objects of the present invention refer to new ways for the diagnosis of diseases associated with carnitine deficiency and to new therapeutic ways to treat diseases associated with carnitine deficiency.

The present invention provides favorable uses of a carnitine transporter which is formed in a tissue-specific way in the intestine and kidneys, in particular of humans, mice and rats. The human carnitine transporter detected in the invention comprises the amino acid sequence SEQ ID NO: 1, the closely related murine carnitine transporter comprises the amino acid sequence SEQ ID NO: 2, and the closely related rat carnitine transporter comprises the amino acid sequence SEQ ID NO: 3. The invention refers in particular to methods for the development of drugs which influence the activity of carnitine transporters and to related test kits, to methods for the manufacture of medicaments for the treatment of carnitine deficiency, to the manufacture of antibodies against carnitine transporters, to diagnostic methods for carnitine deficiency, to oligonucleotides for detecting nucleic acids coding for carnitine transporters, and to therapeutic methods for the treatment of carnitine deficiency.

A first preferred embodiment of the present invention refers to a method of screening for a carnitine transporter agonist or antagonist, wherein the method comprises the steps of: (a) providing a carnitine transporter, (b) providing a test compound, and (c) measuring the activity of the carnitine transporter.

Preferably, the method of screening for a carnitine transporter agonist or antagonist involves (a) providing a cell, tissue sample or organism comprising a nucleic acid molecule coding for a carnitine transporter, (b) providing a test compound to said cell, tissue sample or organism, and (c) measuring the activity of the carnitine transporter. Preferably, measuring the activity of the carnitine transporter involves determining the expression of the nucleic acid molecule coding for the carnitine transporter, and/or providing a substrate for the carnitine transporter to said cell, tissue sample or organism and measuring the transport of the substrate by the carnitine transporter across a lipid membrane of said cell, tissue sample or organism. Determining of the expression of the nucleic acid molecule coding for the carnitine transporter preferably involves determining the transcriptional activity of the nucleic acid molecule and/or determining the amount of the carnitine transporter protein.

Alternatively, the method of screening for a carnitine transporter agonist or antagonist preferably involves (a) providing a carnitine transporter comprised in a lipid membrane separating two volumes comprising an aqueous medium, (b) providing a test compound to at least one of said volumes, and (c) measuring the activity of the carnitine transporter, wherein measuring the activity of the carnitine transporter involves providing a substrate for the carnitine transporter to at least one of said volumes and measuring the transport of the substrate across said lipid membrane.

The test compound is preferably tested for an agonist or antagonist activity on the carnitine transporter. Preferably, a multitude of test compounds are screened for a carnitine transporter agonist or antagonist. Preferably a suitable substrate for the carnitine transporter is carnitine, noradrenaline, methylphenylpyridinium, creatine or serotonin.

The activity of the carnitine transporter is preferably measured by determining the rate of transport of the substrate by the carnitine transporter. Preferably, the rate of transport of the substrate across the lipid membrane is determined. Preferably, the rate of transport of the substrate from one volume to the other is determined. Preferably, the lipid membrane separates two chambers of an experimental setting or is closed to form a membrane of a lipid vesicle or to form the plasma membrane of a living or a reconstituted cell. Preferably, the lipid membrane comprises the carnitine transporter in an orientation that allows transport of a substrate from one chamber to the other chamber or across the membrane of the lipid vesicle or across the plasma membrane. Preferably, determining the rate of transport of the substrate across the lipid membrane comprises measuring the amount of the substrate transported across the lipid membrane.

Preferably, the agonist or antagonist activity of the test compound on the activity of the carnitine transporter is determined by measuring the rate of transport of the substrate by the carnitine transporter in the presence of the test compound and comparing it to the rate of transport of the substrate by the carnitine transporter in the absence of the test compound. Preferably, the method involves control measurements, wherein transport of the substrate over the lipid membrane without the carnitine transporter is measured.

In any embodiment of the present invention, the substrate of the carnitine transporter is any substrate transported by a carnitine transporter, preferably transported by a plant or animal carnitine transporter, preferably transported by a mammalian carnitine transporter, preferably transported by a human, mouse or rat carnitine transporter, in particular by a human, mouse, or rat carnitine transporter of the kidneys or the intestine. Preferably the substrate is any substrate transported by a carnitine transporter comprising the amino acid sequence SEQ ID NO: 1, SEQ ID NO: 2, or SEQ ID NO: 3, or encoded by a nucleic acid molecule comprising SEQ ID NO: 4, or by a carnitine transporter disclosed in any embodiment of the present invention. Preferably, the substrate is carnitine, noradrenaline, methylphenylpyridinium, creatine and/or serotonin. More preferably, the substrate is carnitine.

In the embodiments of the present invention, carnitine preferably comprises L-carnitine and/or D-carnitine, preferably L-carnitine. Preferably, carnitine comprises carnitine derivatives and/or carnitine analogues. Preferably, carnitine derivatives comprise carnitine metabolites and carnitine conjugates. Preferably, carnitine metabolites comprise physiological carnitine metabolites which are formed by chemical alteration of L-carnitine or D-carnitine in vivo, such as acetylcarnitine. Preferably, carnitine conjugates comprise L-carnitine, D-carnitine or a carnitine analogue which is coupled to an effector molecule. Preferably, the effector molecule is a chemical compound that shall be cotransported over a lipid membrane together with carnitine by a carnitine transporter. Preferably, the effector molecule is a drug. Preferably, the coupling is any chemical bond, preferably a covalent bond, ionic bond or Van-der-Vaals bond. Preferably, a carnitine analogue is a chemical compound which possesses an analogous chemical structure to carnitine which allows its transport by a carnitine transporter.

The method of the invention of screening for a carnitine transporter agonist or antagonist preferably involves testing of a test compound for an agonist action enhancing the activity of a carnitine transporter. In alternative, it involves testing of a test compound for an antagonist action inhibiting the activity of a carnitine transporter. Preferably, the method of the invention of screening for a carnitine transporter agonist or antagonist is adapted to the screening of a large number of test compounds, wherein the testing of an individual test compound requires a short time, and preferably the testing of an individual test compound is economical and requires small amounts of reagents, in particular of the test compound.

A test compound tested in the method of the invention of screening for a carnitine transporter agonist or antagonist is preferably a small molecule, preferably a candidate for an effector compound binding to a protein or to an enzyme cofactor. Preferably the test compound is a candidate for an effector compound which can bind to a protein comprising the amino acid sequence SEQ ID NO: 1, SEQ ID NO: 2, or SEQ ID NO: 3 or to any carnitine transporter disclosed in an embodiment of the present invention.

Preferably, a test compound is a candidate for an effector compound which can bind to a protein or to an enzyme cofactor, wherein said protein or enzyme cofactor binds to or is a candidate for a compound binding to a protein comprising the amino acid sequence SEQ ID NO: 1, SEQ ID NO: 2, or SEQ ID NO: 3, or to any carnitine transporter disclosed in an embodiment of the present invention.

Preferably, a test compound is a candidate for an effector compound which can bind to a transcription factor or to a translation factor, preferably wherein the transcription factor or the translation factor increases or decreases the synthesis of a protein comprising the amino acid sequence SEQ ID NO: 1, SEQ ID NO: 2, or SEQ ID NO: 3 or increases or decreases the synthesis of any carnitine transporter disclosed in an embodiment of the present invention.

Preferably, a test compound is a candidate for an effector compound which can directly or indirectly increase or decrease the synthesis or the activity of a transcription factor or of a translation factor, preferably wherein the transcription factor or the translation factor increases or decreases the synthesis of a protein comprising the amino acid sequence SEQ ID NO: 1, SEQ ID NO: 2, or SEQ ID NO: 3 or increases or decreases the synthesis of any carnitine transporter disclosed in an embodiment of the present invention.

Preferably the test compound is any chemical compound, such as a naturally occurring compound, or a chemically synthesized compound that is identical or similar to a naturally occurring compound, or any chemically synthesized compound that does not occur in nature.

A naturally occurring compound is preferably a compound that can be detected in or isolated from a multicellular or single cell organism, in particular a compound that can be detected in or isolated from an animal, a plant, a fungus, a yeast, bacterium, or any other cell-containing organism or in a virus. A chemically synthesized compound that does not occur in nature is preferably synthesized by combinatorial chemistry. Preferably, it comprises a lead structure derived from a naturally occurring compound, preferably from a candidate for an effector molecule which can bind to a protein or to an enzyme cofactor.

Preferably, a carnitine transporter agonist or antagonist identified according to the invention or used in an embodiment of the invention enhances, or inhibits respectively, the activity of a kidney or intestinal carnitine transporter of an individual, preferably of a healthy individual. Preferably the carnitine transporter agonist enhances the activity of a carnitine transporter of an individual suffering from a carnitine transporter deficiency. Preferably, the carnitine transporter agonist enhances the activity of a carnitine transporter in an individual having a reduced amount of a carnitine transporter.

Preferably, the carnitine transporter agonist or antagonist enhances, or decreases respectively, the activity of a genetic variant of a carnitine transporter in an individual. Preferably, the carnitine transporter agonist enhances the activity of a genetic variant of the carnitine transporter associated with carnitine deficiency. Preferably, the carnitine transporter antagonist decreases the activity of a carnitine transporter, preferably of a kidney or intestinal carnitine transporter, in an individual having an increased activity or an increased amount of a carnitine transporter. Preferably, the activity of a carnitine transporter as mentioned herein refers to the transport rate of the carnitine transporter for a substrate, to the amount of the carnitine transporter, and/or to the strength of expression of a nucleic acid molecule coding for the carnitine transporter.

Preferably, the carnitine transporter provided in the method of the invention of screening for a carnitine transporter agonist or antagonist can also be used in any other embodiment of the present invention. The carnitine transporter is preferably a plant or animal carnitine transporter, preferably a mammalian carnitine transporter, preferably a human, mouse, or rat carnitine transporter, preferably a kidney or intestinal carnitine transporter, preferably an intestinal carnitine transporter.

Preferably, the carnitine transporter comprises the amino acid sequence SEQ ID NO: 1, SEQ ID NO: 2, or SEQ ID NO: 3 of the invention. Preferably, the carnitine transporter is a high affinity carnitine transporter produced in the kidneys and in the intestine of a healthy individual. Preferably, the carnitine transporter comprises the amino acid sequence SEQ ID NO: 1 of the high affinity carnitine transporter of the human kidneys and intestine. Preferably, the carnitine transporter comprises the amino acid sequence SEQ ID NO: 10, a functional splice variant of SEQ ID NO: 1 which comprises an additional sequence comprising 39 amino acids (corresponding to amino acids 297 to 335 in SEQ ID NO: 10) between the amino acids 296 and 297 of SEQ ID NO: 1.

Preferably, the carnitine transporter is the orthologous mouse or rat high affinity carnitine transporter produced in the kidneys and in the intestine of healthy animals. Preferably, the carnitine transporter comprises the amino acid sequence SEQ ID NO: 2 or SEQ ID NO: 3, respectively, of the mouse or rat kidney and intestinal high affinity carnitine transporter.

Preferably, the carnitine transporter is a related carnitine transporter comprising a related amino acid sequences to SEQ ID NO: 1, SEQ ID NO: 2, or SEQ ID NO: 3. Preferably, the carnitine transporter comprises a related amino acid sequence to SEQ ID NO: 1. Preferably, the carnitine transporter comprises a related amino acid sequence to SEQ ID NO: 10.

Preferably, the related carnitine transporter comprises an amino acid sequence comprising at least 30% sequence identity to at least one of SEQ ID NO: 1, SEQ ID NO: 2, SEQ ID NO: 3, or SEQ ID NO: 10 and at least 10%, preferably at least 30%, more preferably at least 50%, still more preferably at least 70% of the substrate transport activity for at least one substrate, preferably for carnitine, preferably for L-carnitine, of the carnitine transporter comprising the amino acid sequence SEQ ID NO: 1 or SEQ ID NO: 10, preferably SEQ ID NO: 1.

Preferably, the related carnitine transporter comprises the amino acid sequence of the rat protein AAW07635 (rB21a), available under the accession number AJ276207, of the protein AAG64193 disclosed in CN 1287170, or of the protein AAW73376, namely human HPDDV78 disclosed in EP 881290.

Preferably, the related carnitine transporter comprises an amino acid sequence comprising at least 60% sequence identity to at least one of SEQ ID NO: 1, SEQ ID NO: 2, SEQ ID NO: 3, or SEQ ID NO: 10 and at least 10%, preferably at least 30%, more preferably at least 50%, more preferably at least 70%, still more preferably at least 80% or at least 90% of the substrate transport activity for at least one substrate, preferably for carnitine, preferably for L-carnitine, of the carnitine transporter comprising the amino acid sequence SEQ ID NO: 1 or SEQ ID NO: 10, preferably SEQ ID NO: 1.

Preferably, the carnitine transporter comprises an amino acid sequence comprising at least 85%, preferably at least 86%, preferably at least 86.5% sequence identity to at least one of SEQ ID NO: 1, SEQ ID NO: 2, SEQ ID NO: 3, or SEQ ID NO: 10, and at least 10%, preferably at least 30%, more preferably at least 50%, more preferably at least 70%, still more preferably at least 80% or at least 90% of the substrate transport activity for at least one substrate, preferably for carnitine, preferably for L-carnitine, of the carnitine transporter comprising the amino acid sequence SEQ ID NO: 1 or SEQ ID NO: 10, preferably SEQ ID NO: 1.

Preferably, the carnitine transporter comprises at least 95%, preferably at least 95.4% sequence identity to at least one of SEQ ID NO: 1, SEQ ID NO: 2, SEQ ID NO: 3, or SEQ ID NO: 10, and at least 10%, preferably at least 30%, more preferably at least 50%, more preferably at least 70%, still more preferably at least 80% or at least 90% of the substrate transport activity for at least one substrate, preferably for L-carnitine, preferably for L-carnitine, of the carnitine transporter comprising the amino acid sequence SEQ ID NO: 1, SEQ ID NO: 2, SEQ ID NO: 3, or SEQ ID NO: 10.

Preferably, the amino acid sequence of the carnitine transporter differs from the amino acid sequence according to SEQ ID NO: 1, SEQ ID NO: 2, SEQ ID NO: 3, or SEQ ID NO: 10 by so-called conservative amino acid substitutions which are known to the skilled person and are supposed to have little or no influence on the activity of a protein and hence on the activity of the carnitine transporter. Preferably, the carnitine transporter differs from SEQ ID NO: 1, SEQ ID NO: 2, SEQ ID NO: 3, and/or SEQ ID NO: 10 by amino acid substitutions which are supposed to have little or no influence on the activity of the carnitine transporter by the skilled person who considers the amino acid sequence alignment between SEQ ID NO: 1, SEQ ID NO: 2, and SEQ ID NO: 3, disclosed herein in FIG. 3 below.

Preferably, the carnitine transporter used in any embodiment of the present invention is encoded by a nucleic acid molecule coding for a human carnitine transporter produced in the kidneys and/or in the intestine. Preferably, the nucleic acid molecule is tissue-specifically expressed in the kidneys and/or in the intestine. Preferably, the nucleic acid molecule codes for the human or the mouse or rat carnitine transporter comprising the amino acid sequence SEQ ID NO: 1, SEQ ID NO: 2, SEQ ID NO: 3, or SEQ ID NO: 10.

Preferably, the nucleic acid molecule comprises SEQ ID NO: 4, which codes for the human kidney and intestinal carnitine transporter comprising the amino acid sequence SEQ ID NO: 1. Preferably, the nucleic acid molecule comprises SEQ ID NO: 5, which codes for the orthologous murine kidney and intestinal carnitine transporter comprising the amino acid sequence SEQ ID NO: 2. Preferably, the nucleic acid molecule comprises SEQ ID NO: 8, which codes for the orthologous rat kidney and intestinal carnitine transporter comprising the amino acid sequence SEQ ID NO: 3.

Preferably, the nucleic acid molecule comprises SEQ ID NO: 9, which is a functional splice variant of SEQ ID NO: 4, coding for the amino acid sequence SEQ ID NO: 10. SEQ ID NO: 9 comprises an additional sequence comprising 117 nucleotides (corresponding to nucleotides 888 to 1004 in SEQ ID NO: 9) which are inserted between nucleotides 887 and 888 of SEQ ID NO: 4.

Preferably, the carnitine transporter is encoded by the mRNA comprising SEQ ID NO: 15 for the human kidney and intestinal carnitine transporter. SEQ ID NO: 15 comprises the open reading frame according to SEQ ID NO: 4 and additional non-translated 5' and 3' flanking sequences. The present invention provides for the first time the complete mRNA comprising SEQ ID NO: 15, which codes for the carnitine transporter comprising the amino acid sequence SEQ ID NO: 1. SEQ ID NO: 15 comprises the open reading frame according to SEQ ID NO: 4 which codes for SEQ ID NO: 1, the 5' flanking region comprising nucleotides 1 to 45 of SEQ ID NO: 15, and the 3' flanking region comprising nucleotides 1951 to 5175 of SEQ ID NO: 15.

Preferably, the carnitine transporter is encoded by a nucleic acid molecule which is detectable by a skilled person who uses routine experiments to detect carnitine transporters which are encoded by nucleic acid molecules comprising similar sequences to SEQ ID NO: 4, SEQ ID NO: 5, SEQ ID NO: 8, SEQ ID NO: 9, or SEQ ID NO: 15. Preferably, the carnitine transporter is encoded by a nucleic acid sequence which is similar to SEQ ID NO: 4. Preferably, the nucleic acid molecule is similar to SEQ ID NO: 9. Preferably, the nucleic acid molecule is similar to SEQ ID NO: 15.

Preferably, the nucleic acid molecule coding for the carnitine transporter is detectable by routine experiments for the detection of nucleic acid molecules comprising a known sequence. Preferably, the nucleic acid molecule coding for the carnitine transporter is detectable by routine experiments for the detection of nucleic acid molecules comprising a sequence similar to a known sequence, preferably related to a known nucleic acid sequence, preferably homologous to a known nucleic acid sequence.

Preferably, the carnitine transporter is encoded by a nucleic acid sequence which is similar to a nucleic acid molecules coding for the amino acid sequence SEQ ID NO: 1, SEQ ID NO: 2, or SEQ ID NO: 3.

Preferably, a nucleic acid molecule is similar to a nucleic acid molecule coding for a carnitine transporter of any embodiment of the present invention, if it comprises a sequence having a detectable degree of sequence homology which is readily appreciated by the skilled person, preferably having a detectable degree of sequence identity. Preferably, a nucleic acid molecule is similar to a nucleic acid molecule coding for a carnitine transporter of any embodiment of the invention if it codes for a protein comprising an amino acid sequence having a detectable degree of sequence homology as readily appreciated by the skilled person, preferably having a detectable degree of sequence identity, to the carnitine transporter usable in the invention. Preferably, sequence identities and sequence homologies between nucleic acid molecules can be detected without undue burden in hybridization experiments, wherein complementary base pairing is allowed under stringent or under non-stringent conditions.

Preferably, a nucleic acid molecule is similar to a nucleic acid molecule coding for a carnitine transporter of an embodiment of the invention if it hybridizes to a nucleic acid molecule comprising SEQ ID NO: 4, SEQ ID NO: 5, SEQ ID NO: 8, or SEQ ID NO: 9, SEQ ID NO: 15, or to a complementary sequence thereof or if it hybridizes to a fragment thereof or to a complementary sequence thereof comprising at least 18 nucleotides, preferably at least 25 nucleotides, preferably at least 50 nucleotides. Preferably, non-stringent conditions are used, more preferably stringent conditions are used. The similarity of nucleic acid molecules coding for the amino acid sequences SEQ ID NO: 1, SEQ ID NO: 2, SEQ ID NO: 3, or SEQ ID NO: 10 is determined in an analogous way.

Preferably, a nucleic acid molecule coding for a carnitine transporter according to an embodiment of the invention is detectable by the skilled person who uses for the detection the 5' flanking region of SEQ ID NO: 15 or the 3' flanking region of SEQ ID NO: 15, preferably the 3' flanking region. Preferably a fragment of the 3' region of SEQ ID NO: 15 is used, preferably comprising at least 18 nucleotides, preferably at least 25 nucleotides, preferably at least 50 nucleotides. Preferably, non-stringent conditions are used, more preferably stringent conditions are used. Preferably the detection involves a hybridization assay or a PCR analysis, either of which bases on the well-known concept of complementary base pairing.

Non-stringent conditions and stringent conditions of hybridization are known to the skilled person. Preferably, non-stringent conditions comprise 3×SSC, 0.5% Sodium N-lauryl sarcosine and 60° C. Preferably, stringent conditions comprise 1×SSC, 0.1% Sodium dodecylsulfate (SDS) and 65° C. Preferably 20×SSC comprises 3M NaCl, 0.3M tri-Sodium citrate, pH 7.0.

In the method of the invention of screening for a carnitine transporter agonist or antagonist which involves providing a carnitine transporter comprised in a lipid membrane, the carnitine transporter is preferably comprised in a cellular membrane, preferably in an inner mitochondrial membrane or in a plasma membrane. Suitable membrane lipids are either naturally occurring membrane lipids of cellular membranes, and/or membrane-forming lipids which are not known in nature but which are known to the chemist.

Preferably, the lipid membrane comprises lipids forming a membrane, which can comprise the carnitine transporter. Such lipids are known to the skilled person. Preferably the lipids can be used to form a liposome. Preferably, the lipids are components of or are derived from a cellular membrane, preferably a plasma membrane or an inner mitochondrial membrane. Preferably, the lipids are identical or have a similar chemical structure as lipids of biological membranes and are capable of forming a lipid bilayer or a lipid monolayer having two hydrophilic surfaces in an aqueous medium.

Preferably, the lipid membrane comprising the carnitine transporter separates two volumes comprising aqueous media. Preferably the two volumes are two buffer tanks of an experimental setting.

The lipid membrane comprising the carnitine transporter comprises preferably a reconstituted cellular membrane. The reconstituted cellular membrane is preferably derived from a living cell. The methods of forming a reconstituted cellular membrane are known to the skilled person.

Preferably the carnitine transporter is comprised in a lipid vesicle membrane. Preferably a lipid vesicle comprises a liposome or a closed reconstituted cellular membrane. The liposome or the reconstituted cellular membrane is formed by any suitable method. Preferably, the liposome or reconstituted membrane vesicle is formed by exposing a mixture comprising at least one type of membrane lipid and the carnitine transporter to ultrasonic waves or by leading the mixture through a small-diameter outlet, in particular a syringe, into a buffer solution. Preferably, the reconstituted cell is made by opening a living cell, providing the carnitine transporter and resealing the plasma membrane. During the opening and resealing of the cell components of the cytoplasm may or may not be lost, and consequently the reconstituted plasma membrane comprising the carnitine transporter may belong to a living cell or be a so-called membrane ghost.

In a preferred embodiment, the carnitine transporter is comprised in the plasma membrane of a test cell. Preferably, the test cell expresses a nucleic acid molecule coding for a carnitine transporter, preferably a plant or animal carnitine transporter, preferably a mammalian, preferably a mouse or rat carnitine transporter, preferably a human carnitine transporter, preferably a kidney or intestinal carnitine transporter, preferably a human, mouse, or rat kidney or intestinal carnitine transporter.

Preferably the test cell expresses a nucleic acid molecule coding for a carnitine transporter comprising the amino acid sequence SEQ ID NO: 1, SEQ ID NO: 2, SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, preferably the test cell expresses a nucleic acid coding for SEQ ID NO: 1, SEQ ID NO: 2, SEQ ID NO: 3, or SEQ ID NO: 10, preferably SEQ ID NO: 1 or SEQ ID NO: 10, preferably SEQ ID NO: 1. Preferably, the test cell expresses a nucleic acid molecule comprising SEQ ID NO: 4, SEQ ID NO: 5, SEQ ID NO: 8, SEQ ID NO: 9, or SEQ ID NO: 15, preferably SEQ ID NO: 4, SEQ ID NO: 9 or SEQ ID NO: 15, preferably SEQ ID NO: 4 or SEQ ID NO: 15. Preferably, the test cell comprises any of said nucleic acid molecules operably linked to a transcriptional activator sequence, preferably SEQ ID NO: 4, SEQ ID NO: 9, or SEQ ID NO: 15, preferably SEQ ID NO: 4 or SEQ ID NO: 15 operably linked to a transcriptional activator sequence. Preferably, the test cell comprises a translatable RNA molecule comprising a sequence corresponding to SEQ ID NO: 4, SEQ ID NO: 9, or SEQ ID NO: 15, preferably SEQ ID NO: 4 or SEQ ID NO: 15. Preferably, the test cell comprises a microinjected cRNA molecule comprising a sequence corresponding to SEQ ID NO: 4, SEQ ID NO: 9 or SEQ ID NO: 15, preferably SEQ ID NO: 4 or SEQ ID NO: 15.

Preferably, the test cell comprises a functional carnitine transporter in its plasma membrane. Preferably, the carnitine transporter transports a substrate selected from carnitine, noradrenaline, methylphenylpyridinium, creatine, and/or serotonin across the plasma membrane. Preferably, the carnitine transporter transports the substrate into the test cell. Preferably, the test cell is a bacterial or a eukaryotic cell, in particular a yeast cell. Preferably, the test cell belongs to a primary cell line or to a permanent cell line. Preferably, the test cell is a *Xenopus laevis* oocyte. Preferably, the *Xenopus laevis* oocyte comprises an injected cRNA comprising SEQ ID NO: 4, SEQ ID NO: 9 or SEQ ID NO: 15, preferably SEQ ID NO: 4 or SEQ ID NO: 15.

Preferably, a detectable substrate for the carnitine transporter is used. Preferably the detectable substrate allows its detection inside in the test cell. Preferably, the detectable substrate allows for the quantification of small amounts of the detectable substrate which are accumulated inside the test cell.

The method of the invention of screening of test compounds for agonist or antagonist activity of a carnitine transporter preferably comprises measuring the amount of a detectable substrate which is transported by the carnitine transporter across a lipid membrane, in particular across a plasma membrane into a test cell, wherein the amount of the substrate transported across a lipid membrane is indicative of the activity of the carnitine transporter.

Preferably, the detectable carnitine transporter substrate is a radioactively labeled substrate, a streptavidin-labeled or biotinylated substrate, or a substrate reacting with an antibody.

Preferably, the test compounds screened for having an agonist or an antagonist activity on the carnitine transporter are provided in the form of a chemical compound library. According to the invention, the term "chemical compound library" refers to a plurality of chemical compounds that have been assembled from any of multiple sources, including chemically synthesized molecules and natural products, or that have been generated by combinatorial chemistry techniques.

Preferably, the method of the invention for screening for a carnitine transporter agonist or antagonist is automated, preferably it is carried out in a robotics system.

A second preferred embodiment of the invention refers to a kit for carrying out the method of the invention of screening for a carnitine transporter agonist or antagonist comprising a lipid membrane, which comprises a carnitine transporter, and a detectable substrate for the carnitine transporter. The kit of the invention preferably allows the screening of test compounds comprised in a group of test compounds, in particular in a chemical compound library.

Preferably, the carnitine transporter provided in the kit of the invention is a human, mouse, or rat carnitine transporter. Preferably the carnitine transporter comprises the amino acid sequence SEQ ID NO: 1, SEQ ID NO: 2, SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, preferably SEQ ID NO: 1, SEQ ID NO: 2, SEQ ID NO: 3, or SEQ ID NO: 10, preferably SEQ ID NO: 1 or SEQ ID NO: 10, preferably SEQ ID NO: 1. Preferably, the carnitine transporter is encoded by a nucleic acid molecule comprising SEQ ID NO: 4, SEQ ID NO: 5, SEQ ID NO: 9, SEQ ID NO: 15, preferably SEQ ID NO: 4 or SEQ ID NO: 15, or by a nucleic acid coding for at least one of said proteins. Preferably, the lipid membrane separates two volumes of an experimental setting, in particular two buffer tanks, or is closed to form a lipid vesicle, or to form the plasma membrane of a living or a reconstituted cell. Preferably, the carnitine transporter is comprised in a lipid vesicle membrane. Preferably, the carnitine transporter is comprised in the plasma membrane of a test cell.

Preferably, the kit of the invention comprises a detectable substrate for the carnitine transporter, in particular a radioactive, streptavidin-labeled or biotinylated substrate, or a substrate detectable with an antibody. Preferably, the kit comprises an antibody reacting with the substrate. Preferably, the substrate is carnitine, noradrenaline, methylphenylpyridinium, creatine, and/or serotonin. Preferably, the substrate is carnitine.

In any embodiment of the present invention, the expression "antibody" comprises any monoclonal antibody, antiserum, in particular polyvalent antiserum, antiserum fraction, antibody fragment, recombinantly produced antibody or antibody fragment, comprising the reactivity with its antigen indicated herein.

Preferably, the kit of the invention comprises any component or feature of the method of the invention for screening of a carnitine transporter agonist or antagonist.

A third preferred embodiment of the invention refers to a method for the manufacture of a medicament for the treatment of a carnitine transporter deficiency, wherein the method comprises the steps of: (a) identifying an agonist of a carnitine transporter using the method of the invention of screening for an agonist or antagonist of a carnitine transporter, (b) providing a sufficient amount of the agonist, and (c) formulating the agonist with one or more pharmaceutically acceptable carriers or auxiliary substances.

Preferably, the method refers to the manufacture of a medicament for the treatment of a carnitine transporter deficiency of the kidney or intestinal carnitine transporter. Preferably, the method refers to the manufacture of a medicament for the treatment of systemic carnitine deficiency.

Preferably, the method refers to the manufacture of a medicament for the treatment of a deficiency of carnitine, noradrenaline, methylphenylpyridinium, creatine, and/or serotonin transport. Preferably, the method refers to the manufacture of a medicament for the treatment of any deficiency of a substrate transported by a human or animal carnitine transporter of the invention comprising the amino acid sequence SEQ ID NO: 1, SEQ ID NO: 2, SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, preferably SEQ ID NO: 1, SEQ ID NO: 2, SEQ ID NO: 3, or SEQ ID NO: 10, preferably SEQ ID NO: 1 or SEQ ID NO: 10, preferably SEQ ID NO: 1 or encoded by a nucleic acid molecule comprising SEQ ID NO: 4, SEQ ID NO: 5, SEQ ID NO: 9, SEQ ID NO: 15, preferably SEQ ID NO: 4 or SEQ ID NO: 15, or by a nucleic acid coding for at least one of said proteins. Preferably, the method refers to the manufacture of a medicament for the treatment of any deficiency of a substrate transported by any carnitine transporter having a similar amino acid sequence to the carnitine transporter of the invention, which is detectable as disclosed herein or which is detectable by the skilled person basing on the disclosure herein without undue experimental burden.

Preferably, any aspect of the method of the invention of screening for a carnitine transporter agonist refers also to the step of identifying an agonist of a carnitine transporter of the method of the invention for the manufacture of a medicament for the treatment of a carnitine transporter deficiency.

In the method for the manufacture of a medicament, a sufficient amount of the agonist is preferably a therapeutically effective amount, preferably a therapeutically effective amount of a unit dose of administration of the medicament. Preferably, the a therapeutically effective amount is therapeutically sufficient for the treatment of a carnitine transporter deficiency caused by a decreased amount of a functional carnitine transporter in a patient, or caused by a variant of a carnitine transporter having a decreased activity in a patient.

The specific therapeutically effective dose level for any particular patient will depend upon a variety of factors including the activity of the identified carnitine transporter agonist, the dosage form, the age, body weight and sex of the patient, the duration of the treatment and like factors well known in the medical arts. Preferably, the unit dose is therapeutically sufficient for the treatment of an adult, a child, a small child, a new born, or for the treatment of an unborn child during pregnancy.

The total daily dose of the carnitine transporter agonist of the invention administered to a human or other mammal in single or in divided doses can be in amounts, for example, from about 0.01 to about 50 mg/kg body weight or more preferably from about 0.1 to about 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the carnitine transporter agonist of the present invention per day in single or multiple doses.

Preferably, a combination of more than one carnitine transporter agonist is used for the manufacture of the medicament. Still preferably, the medicament comprises in addition carnitine. Preferably, the amount of carnitine comprised in a unit dose medicament is adjusted to the activity of the carnitine transporter mediated by the carnitine transporter agonist comprised in the unit dose medicament.

For the production of the medicament the carnitine transporter agonist of the present invention is preferably formulated with one or more pharmaceutically acceptable additives or auxiliary substances, such as physiological buffer solution, e.g. sodium chloride solution, demineralized water, stabilizers, such as protease or nuclease inhibitors, preferably aprotinin, ε-aminocaproic acid or pepstatin A or sequestering agents such as EDTA, gel formulations, such as white vaseline, low-viscosity paraffin and/or yellow wax, etc. depending on the kind of administration.

Suitable further additives are, for example, detergents, such as, for example, Triton X-100 or sodium deoxycholate, but also polyols, such as, for example, polyethylene glycol or glycerol, sugars, such as, for example, sucrose or glucose, zwitterionic compounds, such as, for example, amino acids such as glycine or in particular taurine or betaine and/or a protein, such as, for example, bovine or human serum albumin. Detergents, polyols and/or zwitterionic compounds are preferred.

The physiological buffer solution preferably has a pH of approx. 6.0-8.0, especially a pH of approx. 6.8-7.8, in particular a pH of approx. 7.4, and/or an osmolarity of approx. 200-400 milliosmol/liter, preferably of approx. 290-310 milliosmol/liter. The pH of the pharmaceutical composition is in general adjusted using a suitable organic or inorganic buffer, such as, for example, preferably using a phosphate buffer, tris buffer (tris(hydroxymethyl)aminomethane), HEPES buffer ([4-(2-hydroxyethyl)piperazino]ethanesulphonic acid) or MOPS buffer (3-morpholino-1-propanesulphonic acid). The choice of the respective buffer in general depends on the desired buffer molarity. Phosphate buffer is suitable, for example, for injection and infusion solutions.

The pharmaceutical composition can be administered in a conventional manner, e.g. by means of oral dosage forms, such as, for example, tablets or capsules, by means of the mucous membranes, for example the nose or the oral cavity, in the form of dispositories implanted under the skin, by means of injections, infusions or gels which contain the pharmaceutical compositions according to the invention. It is further possible to administer the pharmaceutical composition topically and locally, if appropriate, in the form of liposome complexes. Furthermore, the treatment can be carried out by means of a transdermal therapeutic system (TTS), which makes possible a temporally controlled release of the pharmaceutical compositions. TTS are known for example, from EP 0 944 398 A1, EP 0 916 336 A1, EP 0 889 723 A1 or EP 0 852 493 A1.

Injection solutions are in general used if only relatively small amounts of a solution or suspension, for example about 1 to about 20 ml, are to be administered to the body. Infusion solutions are in general used if a larger amount of a solution or suspension, for example one or more liters, are to be administered. Since, in contrast to the infusion solution, only a few milliliters are administered in the case of injection solutions, small differences from the pH and from the osmotic pressure of the blood or the tissue fluid in the injection do not make themselves noticeable or only make themselves noticeable to an insignificant extent with respect to pain sensation. Dilution of the formulation according to the invention before use is therefore in general not necessary. In the case of the administration of relatively large amounts, however, the formulation according to the invention should be diluted briefly before administration to such an extent that an at least approximately isotonic solution is obtained. An example of an isotonic solution is a 0.9% strength sodium chloride solution. In the case of infusion, the dilution can be carried out, for example, using sterile water while the administration can be carried out, for example, via a so-called bypass.

The pharmaceutical composition can be manufactured for oral, nasal, rectal, parenteral, vaginal, topic or vaginal administration. Parental administration includes subcutaneous, intracutaneous, intramuscular, intravenous or intraperitoneal administration.

In addition, the invention also refers to agonists and antagonists of a carnitine transporter, which are identifiable using the method of the invention of screening for an agonist or antagonist of a carnitine transporter.

A fourth preferred embodiment of the invention refers to a method of diagnosis of a carnitine transporter deficiency in an animal, preferably in a human patient. Preferably, the method comprises determining the amount of a carnitine transporter comprising the amino acid sequence SEQ ID NO: 1, SEQ ID NO: 2, SEQ ID NO: 3, SEQ ID NO: 10, the rat protein AAW07635 (rB21a), available under the accession number AJ276207, the protein MG64193 disclosed in CN 1287170, or the protein AAW73376, namely human HPDDV78 disclosed in EP 881290, preferably comprising SEQ ID NO: 1, SEQ ID NO: 2, SEQ ID NO: 3, or SEQ ID NO: 10, preferably SEQ ID NO: 1 or SEQ ID NO: 10, preferably SEQ ID NO: 1, in a tissue sample obtained from the animal or human patient.

Preferably, an antibody reacting with the carnitine transporter is used in the method of diagnosis. Preferably, an antibody of the invention is used. Preferably, the absence or the presence of a protein reacting with the antibody is determined and is indicative of the absence or the presence of the carnitine transporter in the tissue sample.

In a preferred embodiment, an antibody reacting with a variant of the carnitine transporter associated with the carnitine transporter deficiency is used. The diagnostic method of the invention, wherein the amount of a carnitine transporter or a variant thereof is determined using an antibody, involves any immunological method of the art or which will become available in the future, wherein an antibody is used for determining the amount of its antigen.

Preferably, the invention refers to the use of an ELISA assay known in the art for determining the absence or presence of the carnitine transporter or its variant in the tissue sample. Preferably, the ELISA assays is used to determine the relative amount of the carnitine transporter in the tissue sample obtained from the patient as compared to a healthy individual. Preferably, the invention refers to the use of a Western analysis known in the art, wherein the amount and in addition the size of the carnitine transporter or its variant in the tissue sample can be determined.

In a preferred embodiment, the method of diagnosis is an in vitro diagnostic method which is executed using a tissue sample which has been obtained from an animal or human patient prior to the method of diagnosis of the invention.

In a further preferred embodiment, the method of diagnosis involves an additional initial step, wherein a tissue sample is obtained from an animal or human patient. Preferably, the method of diagnosis comprises at least one step which is executed within the animal or human patient's body.

A fifth preferred embodiment of the invention refers to the use of a protein comprising the amino acid sequence SEQ ID NO: 1, SEQ ID NO: 2, SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, preferably SEQ ID NO: 1 or SEQ ID NO: 10, preferably SEQ ID NO: 1, or a fragment thereof for the manufacture of an antibody reacting with a carnitine transporter comprising the amino acid sequence SEQ ID NO: 1, SEQ ID NO: 2, SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, respectively, preferably SEQ ID NO: 1 or SEQ ID NO: 10, preferably SEQ ID NO: 1. Preferably, a variant of the carnitine transporter associated with a carnitine transporter deficiency is used.

The manufacture of an antibody of the invention refers to any method for the manufacture of an antibody which is available in the art, or which will become available in the future. The manufacture of an antibody of the invention refers to any meaning of the expression "antibody" mentioned herein.

Preferably, a variant of a carnitine transporter associated with a carnitine deficiency in an animal or a human patient is used for the manufacture of the antibody. A variant of a carnitine transporter associated with a carnitine deficiency is preferably a carnitine transporter comprised in a tissue sample of an animal or preferably of a human patient suffering from a carnitine deficiency, preferably systemic carnitine deficiency. The variant of the carnitine transporter is preferably comprised in a tissue sample from the kidneys or from the intestine.

A sixth preferred embodiment of the invention refers to a method of determining a variant of a carnitine transporter associated with a carnitine transporter deficiency, wherein the method comprises the steps of: (a) determining a nucleic acid sequence coding for a variant of SEQ ID NO: 1, SEQ ID NO: 2, or SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, preferably SEQ ID NO: 1 or SEQ ID NO: 10, preferably SEQ ID NO: 1 associated with said carnitine transporter deficiency, and (b) deducing the amino acid sequence of said variant of said carnitine transporter.

The nucleic acid sequence is preferably determined using an animal tissue sample or a human tissue sample comprising the variant of the carnitine transporter. Preferably, the nucleic acid sequence of a nucleic acid molecule comprised in the tissue sample is determined. Preferably the nucleic acid sequence corresponds to SEQ ID NO: 4, SEQ ID NO: 5, SEQ ID NO: 8, or SEQ ID NO: 15, preferably SEQ ID NO: 4 or SEQ ID NO: 15, or codes for a variant of the carnitine transporter comprising the amino acid sequence SEQ ID NO: 1, SEQ ID NO: 2, SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, preferably SEQ ID NO: 1 or SEQ ID NO: 10, preferably SEQ ID NO: 1, preferably SEQ ID NO: 1 or SEQ ID NO: 10, preferably SEQ ID NO: 1.

The determination of the nucleic acid sequence is preferably executed using any of the methods of the art for determining nucleic acid sequences, in particular using a DNA sequencing protocol, or any method for determining nucleic acid sequences which will become available in the future.

The deduction of the amino acid sequence of the carnitine transporter variant from the nucleic acid sequence coding for the carnitine transporter variant is preferably executed using the unambiguous so-called genetic code known in the art, which assigns an individual amino acid to any nucleotide base triplet in an open reading frame of a nucleotide sequence coding for a protein.

A seventh preferred embodiment of the invention refers to a method of diagnosis of a carnitine transporter deficiency, wherein the method comprises a step of determining the amount of a nucleic acid molecule coding for a carnitine transporter comprising the amino acid sequence SEQ ID NO: 1, SEQ ID NO: 2, SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, preferably SEQ ID NO: 1 or SEQ ID NO: 10, preferably SEQ ID NO: 1, preferably SEQ ID NO: 1 or SEQ ID NO: 10, preferably SEQ ID NO: 1 in a tissue sample. Preferably, the amount of a nucleic acid comprising SEQ ID NO: 4, SEQ ID NO: 5, SEQ ID NO: 8, or SEQ ID NO: 15, preferably SEQ ID NO: 4 or SEQ ID NO: 15, is determined.

Preferably, the amount of a DNA molecule is determined. Preferably, the amount of a RNA molecule is determined. Preferably, the amount of a DNA molecule comprising SEQ ID NO: 4, SEQ ID NO: 5, SEQ ID NO: 8, or SEQ ID NO: 15, preferably SEQ ID NO: 4 or SEQ ID NO: 15, or the amount of a corresponding RNA molecule is determined. Preferably, the amount of a DNA molecule coding for the amino acid sequence SEQ ID NO: 1, SEQ ID NO: 2, SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, preferably SEQ ID NO: 1 or SEQ ID NO: 10, preferably SEQ ID NO: 1, preferably SEQ ID NO: 1 or SEQ ID NO: 10, preferably SEQ ID NO: 1, or the amount of a corresponding RNA molecule is determined.

Preferably, the method of diagnosis involves the use of any method known in the art or which shall become available in the future for determining the amount of a nucleic acid molecule comprising a known sequence or having a detectable similarity to a known nucleic acid sequence. Preferably, the method of diagnosis comprises a step of complementary base pairing between the nucleic acid molecule coding for the carnitine transporter and a complementary nucleic acid probe of the invention.

Preferably, a nucleic acid probe of the invention comprises a nucleic acid molecule comprising a complementary sequence to the nucleic acid molecule coding for the carnitine transporter. Preferably, the nucleic acid probe comprises a complementary sequence to SEQ ID NO: 4, SEQ ID NO: 5, SEQ ID NO: 8, or SEQ ID NO: 15, preferably SEQ ID NO: 4 or SEQ ID NO: 15. Preferably, the nucleic acid probe hybridizes to the nucleic acid molecule coding for the carnitine transporter under non-stringent conditions, preferably under stringent conditions. Preferably, the nucleic acid probe comprises an oligonucleotide comprising at least 18 nucleotides.

Preferably, the nucleic acid probe of the invention hybridizes to a variant of the nucleic acid molecule coding for a variant of the carnitine transporter associated with the carnitine transporter deficiency. Preferably, the variant of the nucleic acid molecule comprises a variant of SEQ ID NO: 4, SEQ ID NO: 5, SEQ ID NO: 8, or SEQ ID NO: 15, preferably SEQ ID NO: 4 or SEQ ID NO: 15.

Preferably, complementary base pairing does not only refer to base pairing between a nucleic acid molecule coding for a carnitine transporter and a nucleic acid probe comprising a complementary sequence, but also refers to base pairing between a variant of the nucleic acid molecule and the nucleic acid probe, wherein the nucleic acid probe is only in part complementary to the variant of the nucleic acid molecule. Preferably, complementary base pairing allows for the detection of any nucleic acid molecule coding for a variant of a carnitine transporter with a detectable similarity to a nucleic acid molecule coding for a carnitine transporter of a healthy individual.

Preferably, any embodiment of the invention that refers to nucleic acid molecules or to carnitine transporters encoded by nucleic acid molecules or to any variant thereof, in particular any variant associated with a carnitine transporter deficiency, or any orthologous or homologous variant thereof, refers also to nucleic acid molecules comprising similar sequences, in particular as described herein. Preferably, similar sequences hybridize in complementary base pairing. Preferably similar sequences hybridize under non-stringent conditions, preferably under stringent conditions.

Preferably, the method of diagnosis involves hybridization methods of the art for nucleic acid molecules, in particular a Southern Hybridization method of the art for the detection of a DNA molecule coding for a carnitine transporter in a tissue sample, or a Northern Hybridization method of the art for the detection of a RNA molecule coding for a carnitine transporter in a tissue sample. Preferably, the nucleic acid probe of the invention hybridizing with the DNA molecule or the RNA molecule in the tissue sample is a component of a DNA chip. Preferably, the method of diagnosis comprises a step of extraction of the DNA molecule or the RNA molecule from the tissue sample, which is executed prior to the hybridization with the nucleic acid probe of the invention.

Preferably, the method of diagnosis involves a step of amplification of a nucleic acid molecule coding for a carnitine transporter comprised in a tissue sample. Preferably, the method involves a polymerase chain reaction (PCR) known in the art for the amplification of the nucleic acid molecule. Preferably, a DNA molecule comprised in the tissue sample is amplified. Alternatively, an RNA molecule comprised in the tissue sample is amplified after an additional initial step of reverse transcribing the RNA molecule into a DNA molecule.

An eighth preferred embodiment of the invention refers to an oligonucleotide comprising SEQ ID NO: 6 or comprising the complementary sequence to SEQ ID NO: 7. Advantageously, the oligonucleotides of the invention allow to isolate the gene for a human high affinity carnitine transporter of the kidneys and the intestine.

Preferably, the oligonucleotide comprising SEQ ID NO: 6 or the complementary sequence to SEQ ID NO: 7 is used in the method of the invention of diagnosis of a carnitine transporter deficiency. Preferably, said oligonucleotide is used as a primer in a polymerase chain reaction (PCR). Preferably, said oligonucleotide is used as a component of a DNA array.

A ninth preferred embodiment of the present invention refers to a method of determining a variant of a nucleic acid molecule coding for a variant of a carnitine transporter associated with a carnitine transporter deficiency, wherein the method comprises the steps of: (a) isolating a nucleic acid molecule coding for the variant of the carnitine transporter from a tissue sample using the method of diagnosis of a carnitine transporter deficiency according to the seventh preferred embodiment of the invention, and (b) determining the nucleic acid sequence of said nucleic acid molecule.

A tenth preferred embodiment of the invention refers to a method of treatment of a carnitine transporter deficiency, wherein the method comprises introducing a nucleic acid molecule coding for a carnitine transporter comprising the amino acid sequence SEQ ID NO: 1, SEQ ID NO: 2, SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, preferably SEQ ID NO: 1 or SEQ ID NO: 10, preferably SEQ ID NO: 1, into a cell. Preferably, a DNA molecule comprising SEQ ID NO: 4, SEQ ID NO: 5, SEQ ID NO: 8, or SEQ ID NO: 15, preferably SEQ ID NO: 4 or SEQ ID NO: 15, is introduced into the cell. Preferably, said DNA sequence comprises a transcriptional promoter sequence which is operably linked to SEQ ID NO: 4, SEQ ID NO: 5, SEQ ID NO: 8, or SEQ ID NO: 15, preferably SEQ ID NO: 4 or SEQ ID NO: 15.

A eleventh preferred embodiment of the invention refers to a method of treatment of a carnitine transporter deficiency, wherein the method comprises enhancing the transcriptional activity of a nucleic acid molecule coding for a carnitine transporter comprising the amino acid sequence SEQ ID NO: 1, SEQ ID NO: 2, SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, preferably SEQ ID NO: 1 or SEQ ID NO: 10, preferably SEQ ID NO: 1, in a cell. Preferably, the transcriptional activity of a cellular gene comprising SEQ ID NO: 4, SEQ ID NO: 5, SEQ ID NO: 8, or SEQ ID NO: 15, preferably SEQ ID NO: 4 or SEQ ID NO: 15, is enhanced.

In the methods of treatment of a carnitine transporter deficiency of the invention the cell wherein a nucleic acid molecule is introduced or wherein the transcriptional activity of a nucleic acid molecule coding for a carnitine transporter is enhanced, preferably is a kidney cell, an intestine cell, a intestine cell, a liver cell, a heart cell, and/or a muscle cell.

Preferably, the methods of treatment of a carnitine transporter deficiency of the invention refer to the treatment of a deficiency of carnitine, noradrenaline, methylphenylpyridinium, creatine, and/or serotonin transport, or of any substrate accepted by the proteins comprising the amino acid sequence SEQ ID NO: 1, SEQ ID NO: 2, SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, preferably SEQ ID NO: 1 or SEQ ID NO: 10, preferably SEQ ID NO: 1. Preferably, they refer to the treatment of systemic deficiency of carnitine.

Preferably, the methods of treatment of a carnitine transporter deficiency of the invention are in vitro methods, wherein cells are treated in vitro. Preferably, the cells were isolated from a patient previously to the steps of the methods of treatment of the invention.

Further preferred embodiments of the methods of treatment of the invention refer to the introduction of a nucleic acid molecule coding for a carnitine transporter according to SEQ ID NO: 1, SEQ ID NO: 2, SEQ ID NO: 3, SEQ ID NO: 10, the rat protein AAW07635 (rB21a), available under the accession number AJ276207, the protein AAG64193 disclosed in CN 1287170, or the protein AAW73376, namely human HPDDV78 disclosed in EP 881290, preferably SEQ ID NO: 1 or SEQ ID NO: 10, preferably SEQ ID NO: 1, into a cell comprised in the human body, preferably in the kidneys or the intestine. In alternative, a cell is first manipulated in vitro and subsequently transferred into the human body.

Preferably, the cells used in the methods of treatment of the invention are obtained from the kidneys or from the intestine, in particular from the intestine.

The nucleic acid molecules comprising SEQ ID NO. 4, SEQ ID NO: 5, SEQ ID NO: 8, or SEQ ID NO: 15, preferably SEQ ID NO: 4 or SEQ ID NO: 15, can be introduced into test cells of the screening method of the invention or into human cells used in the methods of treatment of the invention in naked form, in the form of gene transfer vectors or complexed with liposomes or gold particles.

Examples of gene transfer vectors are viral vectors, for example adenoviral vectors or retroviral vectors (Lindemann et al. (1997), Mol. Med., 3, 466-76; Springer et al. (1988) Mol. Cell., 2, 549-58). Complexes with liposomes usually achieve a very high efficiency of transfection, in particular of skin cells (Alexander and Akhurst, 1995, Hum. Mol. Genet. 4:2279-85). In lipofection, small, unilamellar vesicles composed of cationic lipids are prepared by ultrasonicating the liposome suspension. The DNA is bound ionically on the surface of the liposomes in a ratio which is such that a positive net charge remains and all the plasmid DNA is complexed by the liposomes. In addition to the DOTMA (1,2-dioleyloxypropyl-3-trimethylammonium bromide) and DOPE (dioleoylphosphatidylethanolamine) lipid mixtures employed by Felgner, P. L. et al. (1987), Proc. Natl. Acad. Sci. USA, 84, 7413-7414, a large number of lipid formulations have by now been synthesized and tested for their efficiency in transfecting a variety of cell lines (Behr et al. (1989) Proc. Natl. Acad. Sci. USA, 86, 6982-6986; Gao and Huang (1991), Biochim. Biophys. Acta, 1189, 195-203; Felgner et al. (1994) J. Biol. Chem., 269, 2550-2561). Examples of the lipid formulations are DOTAP N-[1-(2,3-dioleoyloxy)propyl]-N,N,N-trimethylammonium methyl sulphate or DOGS (dioctadecylamidoglycylspermine).

Auxiliary substances which increase the transfer of nucleic acids into the cell can, for example, be proteins or peptides which are bound to the DNA or synthetic peptide-DNA molecules which enable the nucleic acid to be transported into the nucleus of the cell (Schwartz et al. (1999) Gene Therapy 6:282; Brandén et al. (1999) Nature Biotech., 17, 784). Auxiliary substances also include molecules which enable nucleic acids to be released into the cytoplasm of the cell (Planck et al. (1994) J. Biol. Chem., 269, 12918; Kichler et al. (1997) Bioconj. Chem., 8, 213) or, for example liposomes (Uhlmann and Peyman (1990), supra).

Another, particularly suitable form can be obtained by applying the above-described nucleic acids to gold particles and firing these particles into tissue or cells using what is termed a "gene gun" (Wang et al. (1999) J. Invest. Dermatol. 112: 775-81, Tuting et al. (1998) J. Invest. Dermatol. 111: 183-8).

In the following figures, sequences and examples, some preferred embodiments of the invention are described in more detail with reference to the FIGS. 1 and 2 and in the examples. Yet, no limitation of the invention is intended by the details of the preferred embodiments. In contrast, the invention pertains to any embodiment which comprises details which are not explicitly mentioned in the embodiments herein, but which the skilled person finds without undue effort.

DESCRIPTION OF THE FIGURES

FIG. 1 shows an example of a determination of the activity of the carnitine transporter comprising the amino acid sequence SEQ ID NO: 1 with the substrates L-carnitine (column 1), noradrenaline (column 2), methylphenylpyridinium (column 3), and serotonin (column 4). In FIG. 1, the left columns (1) to (4) indicate the transport rate in pmol hour$^{-1}$ oocyte$^{-1}$ of the carnitine transporter for the respective substrate. The right columns (1) to (4) indicate the transport rate of suitable controls not comprising the carnitine transporter.

Figure 1:
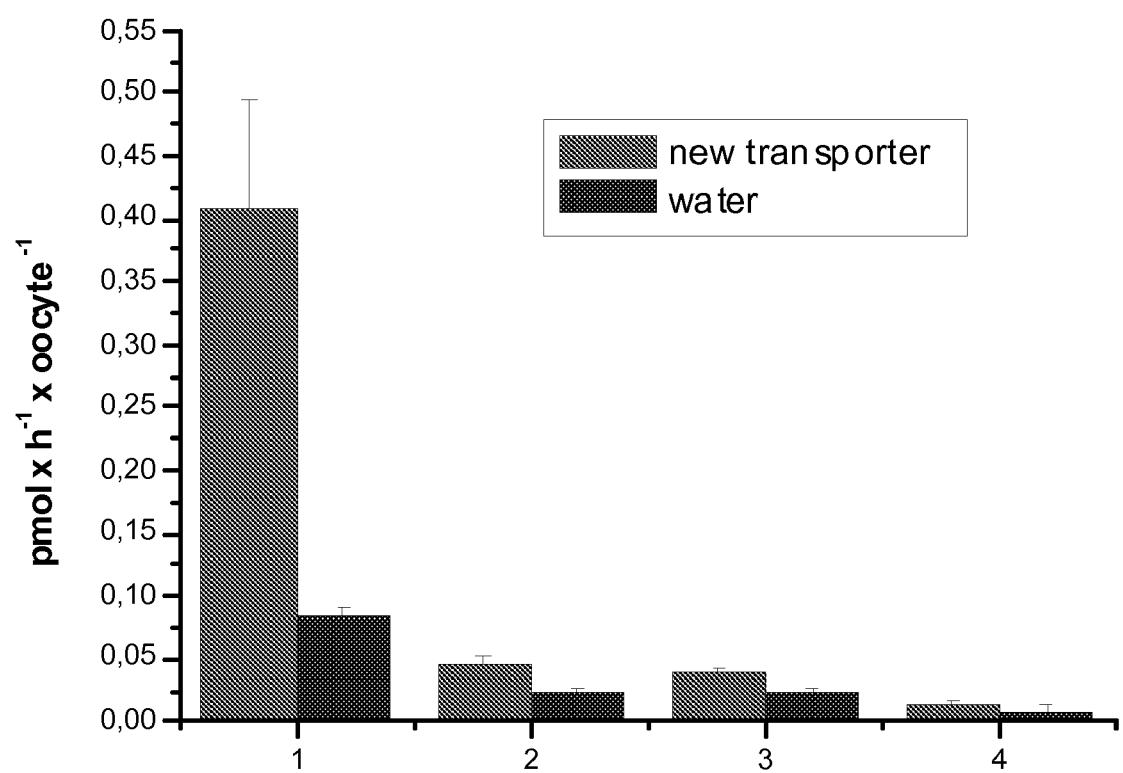
FIG. 1 shows a histogram illustrating the activity of the carnitine transporter involved in the methods of the invention with different substrates.

The carnitine transporters comprising the amino acid sequence SEQ ID NO: 2 or SEQ ID NO: 3 possess comparable activities as shown for the carnitine transporter comprising the amino acid sequence SEQ ID NO: 1 in FIG. 1. The carnitine transporters comprising SEQ ID NO: 1, SEQ ID NO: 2 or SEQ ID NO: 3 transport in addition creatine.

FIG. 1 shows the results obtained with *Xenopus laevis* oocytes injected with a cRNA comprising SEQ ID NO: 4 and with the radioactively labeled substrates L-carnitine (column 1), noradrenaline (column 2), methylphenylpyridinium (column 3), and serotonin (column 4). The controls, which are depicted at the right half of each column comprise control experiments carried through for each substrate with *Xenopus laevis* injected with water instead of the cRNA.

Figure 2:
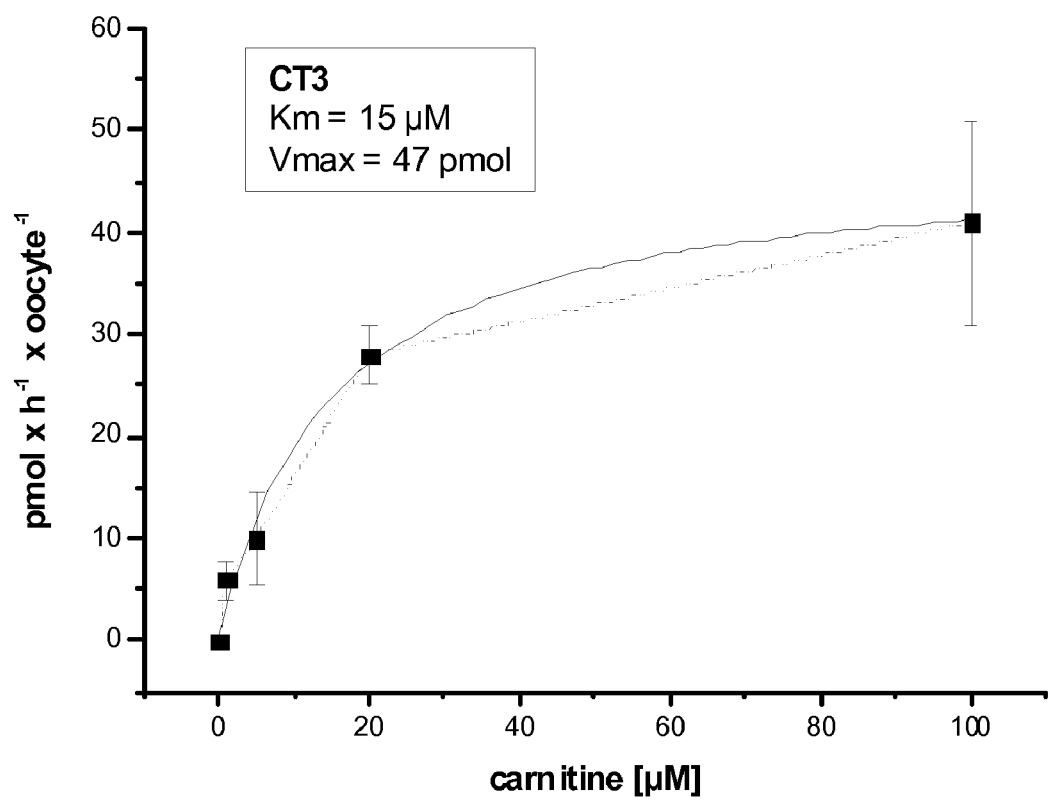

FIG. 2 shows a diagram illustrating the kinetics of the carnitine transporter involved in the methods of the invention. FIG. 2 shows an example of a determination of the kinetics of the carnitine transporter comprising the amino acid sequence SEQ ID NO: 1 with the substrate L-carnitine. The carnitine transporter shows comparable kinetics with the substrates noradrenaline, methylphenylpyridinium, serotonin, and creatine. The carnitine transporter comprising the amino acid sequence SEQ ID NO: 2 or SEQ ID NO: 3 shows comparable kinetics as in FIG. 2. In FIG. 2, the x-axis of the diagram indicates the carnitine concentration in pmol liter$^{-1}$ and the y-axis indicates the transport rate in pmol hour$^{-1}$ oocyte$^{-1}$ of the carnitine transporter.

As shown in FIG. 2, determinations of the concentration dependency of the L-carnitine transport by the carnitine transporter show a saturation of the carnitine transport which can be adapted via Michaelis-Menten kinetics. In the example illustrated in FIG. 2, a $K_M$-value of 15 µM is obtained. Thus, the carnitine transporter used in the methods of the invention, in particular the carnitine transporter comprising the amino acid sequence SEQ ID NO: 1, SEQ ID NO: 2, or SEQ ID NO:3, or encoded by SEQ ID NO: 4 is a high affinity carnitine transporter, such as has been described for the carnitine transport in the kidneys and the intestine (Lahjouji K, Malo C, Mitchell G A, Qureshi I A, 2002, Biochim Biophys Acta, 1558, 82-93).

FIG. 3 shows an amino acid sequence alignment comprising the closely related murine, rat and human kidney and intestinal carnitine transporters comprising SEQ ID NO: 2 with SEQ ID NO: 3, and SEQ ID NO: 1, respectively, each of which comprises 634 amino acids. Corresponding amino acid positions of the individual carnitine transporters are arranged below each other in FIG. 3, and amino acid substitutions occurring at a given positions either in one sequence or at a given position in all three sequences are marked, in order to allow for the observation of so-called conserved regions in the related proteins and for the observation of more variable regions.

It can readily be taken from the sequence identities in FIG. 3 that all three proteins are closely related, yet the mouse and rat proteins are more closely related to each other than to the human carnitine transporter. Further, the skilled person takes without undue burden from FIG. 3 that the relatedness of the shown sequences goes beyond sequence identities and comprises so-called conserved amino acid substitutions at corresponding positions in the sequences. As is well-known in the art, conserved amino acid substitutions comprise substitutions of an amino acid at a given sequence position to a functionally similar amino acid, wherein the function of an amino acid is related to the chemical properties of its side group, in particular to the electrical charge, acid property or base property, hydrophilicity, hydrophobicity, sulfur-content, aromatic property, or size, in particular small size, of its side group.

In addition, the skilled person takes from FIG. 3 without undue burden a variety of sequence motives comprising an arbitrary number of amino acids, which are characteristic for a group comprising either two or three of SEQ ID NO: 1, SEQ ID NO: 2, and/or SEQ ID NO: 3, or which are characteristic for an individual carnitine transporter, preferably for SEQ ID NO: 1. Preferably, a characteristic sequence motif comprises at least one, preferably a group of amino acids comprising at least two, amino acids which do less frequently occur in proteins. The skilled person is used to identify characteristic sequence motifs comprising unusual amino acids with undue burden.

Further, the skilled person considers the additional information about amino acid substitutions between similar amino acids and between closely similar amino acids provided in FIGS. 4, 5, and 6 herein, showing amino acid sequence alignments between SEQ ID NO: 1 and SEQ ID NO: 2, between SEQ ID NO: 1 and SEQ ID NO: 3, and respectively, between SEQ ID NO: 2 and SEQ ID NO: 3.

Preferably, a carnitine transporter used in any embodiment of the present invention is a carnitine transporter which comprises an amino acid sequence motif which is either characteristic for all three carnitine transporters comprising the amino acid SEQ ID NO: 1, SEQ ID NO: 2, or SEQ ID NO: 3, or which is characteristic for an arbitrary group comprising two of said carnitine transporters, or which is characteristic for a single of said carnitine transporter, preferably for SEQ ID NO: 1. Preferably, the carnitine transporter comprises an amino acid motif which can be identified without undue burden due to its similarity to a sequence motif which is either characteristic for all three carnitine transporters shown in FIG. 3, or which is characteristic for an arbitrary group comprising two carnitine transporters, or which is characteristic for a single carnitine transporter, preferably for SEQ ID NO: 1.

FIG. 4 shows an amino acid sequence alignment comprising the closely related human and murine kidney and intestinal carnitine transporters comprising SEQ ID NO: 1 and SEQ ID NO: 2, respectively, which share 86.9% amino acid sequence identity. Identical amino acids are indicated by a bar, similar amino acids which are functionally similar are indicated by a single dot, closely similar amino acids which are almost functionally and/or structurally identical are indicated by a double dot.

FIG. 5 shows an amino acid sequence alignment comprising the closely related human and rat kidney and intestinal carnitine transporters comprising SEQ ID NO: 1 and SEQ ID NO: 3, respectively, which share 86.7% amino acid sequence identity. Identical amino acids are indicated by a bar, similar amino acids which are functionally similar are indicated by a single dot, closely similar amino acids which are almost functionally and/or structurally identical are indicated by a double dot.

FIG. 6 shows an amino acid alignment comprising the closely related murine and rat kidney and intestinal carnitine transporters comprising SEQ ID NO: 2 and SEQ ID NO: 3, respectively, which share 95.4% amino acid sequence identity. Identical amino acids are indicated by a bar, similar amino acids which are functionally similar are indicated by a single dot, closely similar amino acids which are almost functionally and/or structurally identical are indicated by a double dot.

FIG. 7 shows an amino acid sequence alignment comprising SEQ ID NO: 1 and SEQ ID NO: 10. SEQ ID NO: 1 comprises the amino acid sequence of the human kidney and intestinal carnitine transporter, whereas SEQ ID NO: 10 comprises the amino acid sequence of a functional splice variant of SEQ ID NO: 1. SEQ ID NO: 10 comprises the complete and identical amino acid sequence of SEQ ID NO: 1 and an additional amino acid sequence comprising 39 amino acids (corresponding to amino acids 297 to 335 of SEQ ID NO: 10), which are inserted at the position corresponding to a position between amino acids 296 and 297 in SEQ ID NO: 1.

FIG. 8 shows a nucleic acid sequence alignment comprising SEQ ID NO: 4 and SEQ ID NO: 9. SEQ ID NO: 4 codes for the amino acid sequence of the human kidney and intestinal carnitine transporter according to SEQ ID NO: 1, whereas SEQ ID NO: 9 codes for the amino acid sequence of a functional splice variant of SEQ ID NO: 1, namely for the amino acid sequence according to SEQ ID NO: 10. SEQ ID NO: 9 comprises the complete and identical nucleic acid sequence of SEQ ID NO: 4 and an additional nucleic acid sequence comprising 117 nucleotides (corresponding to nucleotides 888 to 1004 of SEQ ID NO: 9), which are inserted at the position corresponding to a position between nucleotides 887 and 888 in SEQ ID NO: 4.

FIG. 9 shows SEQ ID NO: 5.
FIG. 10 shows SEQ IDs NO: 6 and 7.
FIG. 11 shows SEQ ID NO: 8.
FIG. 12 shows SEQ ID NO: 11 (NM_003060).
FIG. 13 shows SEQ ID NO: 12 (NP_003051).
FIG. 14 shows SEQ ID NO: 13 (NM_0033125).
FIG. 15 shows SEQ ID NO: 14 (NPL149116).
FIG. 16 shows SEQ ID NO: 15.

DESCRIPTION OF THE SEQUENCES

SEQ ID NO: 1 comprises the amino acid sequence of the human kidney and intestinal carnitine transporter.

SEQ ID NO: 2 comprises the amino acid sequence of the mouse kidney and intestinal carnitine transporter, which is orthologous to SEQ ID NO: 1.

SEQ ID NO: 3 comprises the amino acid sequence of the rat kidney and intestinal carnitine transporter, which is orthologous to SEQ ID NO: 1.

SEQ ID NO: 4 comprises the open reading frame DNA sequence coding for the human kidney and intestinal carnitine transporter comprising the amino acid sequence SEQ ID NO: 1.

SEQ ID NO: 5 comprises the open reading frame DNA sequence coding for the mouse kidney and intestinal carnitine transporter comprising the amino acid sequence SEQ ID NO: 2.

SEQ ID NO: 6 shows the oligonucleotide of the invention from the start of SEQ ID NO:4, which has been used for cloning SEQ ID NO: 4 (forward cloning primer).

SEQ ID NO: 7 shows the oligonucleotide of the invention downstream from the end of SEQ ID NO: 4, which has been used as a reverse primer for the cloning of SEQ ID NO:4.

SEQ ID NO: 8 comprises the open reading frame DNA sequence coding for the rat kidney and intestinal carnitine transporter comprising the amino acid sequence SEQ ID NO: 3.

SEQ ID NO: 9 comprises SEQ ID NO: 4 and an additional sequence comprising 117 nucleotides inserted between nucleotides 887 and 888 of SEQ ID NO: 4. SEQ ID NO: 9 is available at the NCBI database (National Center for Biotechnology Information U.S.A.) under the accession number XM_291120.

SEQ ID NO: 10 comprises the amino acid sequence encoded by SEQ ID NO: 9, comprising SEQ ID NO: 1 and an additional sequence comprising 39 amino acids inserted between the amino acids 296 and 297 of SEQ ID NO: 9. SEQ ID NO: 10 is available at the NCBI database under the accession number XP_291120.

SEQ ID NO: 11 comprises the DNA sequence coding for the human carnitine transporter OCTN2, which is ubiquitously expressed within the human body. SEQ ID NO: 11 is available at the NCBI database under the accession number NM_003060.

SEQ ID NO: 12 comprises the amino acid sequence encoded by SEQ ID NO: 11, which is available at the NCBI database under the accession number NP_003051.

SEQ ID NO: 13 comprises the DNA sequence coding for the human carnitine transporter CT", which is expressed in human testes only. SEQ ID NO: 13 is available at the NCBI database under the accession number NM_0033125.

SEQ ID NO: 14 comprises the amino acid sequence encoded by SEQ ID NO: 13, which is available at the NCBI database under the accession number NP_149116.

SEQ ID NO: 15 comprises the DNA sequence corresponding to the mRNA for the human kidney and intestinal carnitine transporter, comprising SEQ ID NO: 4, an additional 5'-flanking sequence and an additional 3'-flanking sequence.

DESCRIPTION OF THE EXAMPLES

Identification and Cloning of the Gene of the Kidney and Intestinal Carntine Transporter Surprisingly, it has been found that a nucleic acid molecule comprising SEQ ID NO: 4 is strongly expressed in the human kidneys and in the human intestine in a tissue-specific way. SEQ ID NO: 4 codes for a carnitine transporter comprising the amino acid sequence SEQ ID NO: 1.

A DNA molecule comprising SEQ ID NO: 4 was amplified in a polymerase chain reaction (PCR) using a cDNA from the human kidney as template and oligonucleotide primers comprising SEQ ID NO: 6 and the complementary sequence to SEQ ID NO: 7, which were derived from a DNA sequence publicly available in a data base under the Accession number AK09054.

Transport Measurements using Oocytes

The transport measurements of radioactively labeled compounds were executed using *Xenopus laevis* oocytes in the so-called "tracer flux method", wherein the transport rate of substrates across the oocyte membrane into the cytosol is determined.

Injection of Oocytes of the Clawed Frog *Xenopus laevis*

A *Xenopus laevis* oocyte was injected with a cRNA molecule comprising SEQ ID NO: 4.

The oocytes which were to be injected were aligned in a Sylgard groove. The injection was carried through using glass capillaries made from borosilicate (Hildenberg, Malsfeld; inner diameter: 0.5 mm; outer diameter 1.0 mm), which had been finely stretched within an incandescent spiral-wound filament. For sucking in and pressing out sample solutions a microinjection pump obtained from the company Drummond was used. A capillary was filled without air bubbles with mineral oil (Sigma 400-5 heavy white oil, $\square$=0.88 g/ml) and mounted to a micropump provided with a manipulator.

The still fused tip of the injection capillary was carefully broken open using forceps, in order to allow for the pumping out of the oil and the sucking in of the desired volume of RNA. The sucking in of the RNA into the injection capillary was carried through under a film of sterile mineral oil, in order to avoid an increase of the concentration of the RNA and its degradation by contaminations. The injection capillary was placed on the surface of the oocyte with an angle of 90° and punched into the oocyte under slight pressure. The tip should not penetrate into the cytoplasm deeper than 100-200 µm. The volume of the injectates never exceeded 50 nl (approximately 5% of the oocyte volume of about 0.9 µl). The injection capillary was left within the oocyte for 5-10 seconds after the application of the desired volume, in order to allow for pressure compensation and to avoid leaking out of the injectate through the open punching channel.

An additional provision in order to avoid the leaking out was the "preshrinking" of the oocytes for at least 10 minutes prior to the injection in ORi comprising 130 instead of 10 mM NaCl, i.e. in hypertonic solution. Oocytes which might have lost a substantial amount of yolk and thus possibly a part of the injection solution, were sorted out.

Injected oocytes were kept in the culture medium ORi comprising gentamycin (50 mg/L) at 18° C. until the measurement of substrate uptake. Injured, acutely altered or later heavily damaged cells were discarded.

After 72 hours the oocyte was used for screening for a carnitine transporter agonist or antagonist.

Culture Medium ORi Solution

The standard buffer was a oocyte-Ringer solution ORi comprising 110 mM NaCl, 3 mM KCl, 2 mM $CaCl_2$, 1 mM $MgCl_2$, and 5 mM MOPS.

If required, Gentamycin was added at 50 mg/l,

Determination of the Substrate Uptake

Polysterene wells treated with oocyte homogenate were filled with 200 µl substrate solution. The oocytes were first washed two times with ORi solution, before use in the determination. 8 to 10 oocytes were used in a reaction mixture, in order to enable statistical evaluations. After the addition of the oocytes into the substrate solution the reaction mixture was softly mixed and incubated. The incubation was carried through at 22° C. for 1 hour. In order to stop the reaction, 1 ml of ice cold ORi was added.

The oocytes were washed four times in 15 ml ice cold ORi. Subsequently the oocytes were individually transferred into a 6 ml counter vial. The oocyte plasma membrane was disrupted by adding 100 µl 5 § SDS solution. The vials were slightly agitated to disrupt the plasma membrane. The plasma membrane was completely disrupted by agitation for 30 to 45 minutes. The lysates were mixed with 2 ml of a scintillation cocktail. The radioactivity of the lysates was determined in a liquid scintillation counter comprising a correction for the luminescence and an external standard. Each vial was counted for 5 minutes.

In order to determine the substrate concentration after the dropping in of the oocytes, 2×10 µl solution were removed from the reaction mixture, 100 µl 5% SDS solution was added and evaluations with the counter were carried out. The obtained values were considered in the calculation of the transport rates.

Determination of the $K_M$-Value

For the determination of concentration-dependent substrate uptake serial dilutions of the investigated substrate were prepared and the radioactivity was distributed, such that in each reaction mixture between 10000 and 20000 cpm were counted in the supernatant. For the $K_M$ determination the substrate uptake was measured for 1 hour. In addition, the measurement was carried through using $H_2O$-injected oocytes, in order to determine the background, i.e. the unspecific substrate uptake, for example mediated by diffusion or by endogenous transport proteins. The transport rates were calculated and graphically plotted against the substrate concentration and adapted mathematically according to the Michaelis-Menten equation.

The invention claimed is:

1. A method of screening for a carnitine transporter agonist or antagonist, wherein the method comprises:
   (a) providing a mammalian carnitine transporter selected from the group consisting of SEQ ID NO: 1, SEQ ID NO: 2, and SEQ ID NO: 3;
   (b) providing a test compound; and
   (c) measuring the rate of transport of carnitine across a lipid membrane by said mammalian carnitine transporter; and
   (d) comparing said measured rate of transport to the rate of transport of carnitine by said mammalian carnitine transporter in the absence of the test compound, where increased transport indicates that the test compound is an agonist and decreased transport indicates that the test compound is an antagonist.

2. The method according to claim 1, wherein the carnitine transporter is in a lipid vesicle membrane.

3. The method according to claim 1, wherein the carnitine transporter is in the plasma membrane of a test cell.

4. The method according to claim 3, wherein the test cell expresses a nucleic acid molecule coding for said carnitine transporter.

5. The method according to claim 4, wherein the test cell comprises a DNA sequence selected from the group consisting of SEQ ID NO: 4, SEQ ID NO: 5, and SEQ ID NO: 8.

6. The method according to claim 3, wherein the test cell is a Xenopous laevis oocyte injected with cRNA that is translated to provide said mammalian carnitine transporter.

7. The method according to claim 1, wherein the carnitine is detectably labeled, said label selected from the group consisting of a radioactive label, a streptavidin label, and a biotin label, or the carnitine is measured by reacting with an antibody.

8. The method according to claim 1, wherein the test compound is from a chemical library.

* * * * *

UNITED STATES PATENT AND TRADEMARK OFFICE
CERTIFICATE OF CORRECTION

PATENT NO. : 7,879,563 B2
APPLICATION NO. : 11/573744
DATED : February 1, 2011
INVENTOR(S) : Petra Arndt et al.

Page 1 of 1

It is certified that error appears in the above-identified patent and that said Letters Patent is hereby corrected as shown below:

In column 14, line 2, delete "MG64193" and insert -- AAG64193 --, therefor.

In column 22, line 10, delete "(NPL149116)." and insert -- (NP_149116). --, therefor.

In column 41, line 37, delete "672" and insert -- 673 --, therefor.

In column 45, line 31, above "<210> SEQ ID NO 11" insert -- Tyr --.

In column 62, line 28, in claim 6, delete "Xenopous" and insert -- Xenopus --, therefor.

Signed and Sealed this
Twelfth Day of July, 2011

David J. Kappos
*Director of the United States Patent and Trademark Office*